United States Patent
Altschuler et al.

(10) Patent No.: US 11,007,304 B2
(45) Date of Patent: May 18, 2021

(54) OPTIMIZED SOLID SUBSTRATES, TOOLS FOR USE WITH SAME AND USES THEREOF FOR PROMOTING CELL AND TISSUE GROWTH

(71) Applicant: CARTIHEAL (2009) LTD, Kfar Saba (IL)

(72) Inventors: Nir Altschuler, Tsur Yitskhak (IL); Amir Goren, Yehud (IL)

(73) Assignee: CARTIHEAL (2009) LTD, Kfar Saba (IL)

( * ) Notice: Subject to any disclaimer, the term of this patent is extended or adjusted under 35 U.S.C. 154(b) by 0 days.

(21) Appl. No.: 15/569,000

(22) PCT Filed: May 4, 2016

(86) PCT No.: PCT/IL2016/050469
§ 371 (c)(1),
(2) Date: Oct. 24, 2017

(87) PCT Pub. No.: WO2016/178226
PCT Pub. Date: Nov. 10, 2016

(65) Prior Publication Data
US 2018/0154041 A1    Jun. 7, 2018

Related U.S. Application Data

(60) Provisional application No. 62/157,485, filed on May 6, 2015, provisional application No. 62/331,471, filed on May 4, 2016.

(51) Int. Cl.
*A61B 17/16* (2006.01)
*A61L 27/36* (2006.01)
(Continued)

(52) U.S. Cl.
CPC ...... *A61L 27/3604* (2013.01); *A61B 17/1604* (2013.01); *A61B 17/1615* (2013.01);
(Continued)

(58) Field of Classification Search
CPC ............... A61F 2/447; A61F 2/4611; A61F 2002/30332; A61F 2002/30538;
(Continued)

(56) References Cited

U.S. PATENT DOCUMENTS 5,490,852 A   2/1996 Azer et al.
5,976,147 A   11/1999 LaSalle et al.
(Continued)

FOREIGN PATENT DOCUMENTS

| WO | WO-2013171736 A1 * | 11/2013 | ............. A61L 27/20 |
| WO | WO 2016/178226 A9 | 11/2016 | |
| WO | WO 2019/135216 A1 | 7/2019 | |

OTHER PUBLICATIONS

International Search Report (ISR) for PCT/IL2016/050469; I.A. fd May 4, 2016, dated Oct. 10, 2016, from the European Patent Office, Rijswijk, Netherlands.
(Continued)

*Primary Examiner* — Ann Schillinger
(74) *Attorney, Agent, or Firm* — Sterne, Kessler, Goldstein & Fox P.L.L.C.

(57) ABSTRACT

This invention provides optimized solid substrates for promoting cell or tissue growth or restored function, which solid substrate comprises aragonite and is characterized by a specific fluid uptake capacity value of at least 75%, or a contact angle value of less than 60 degrees when in contact with a fluid and which is further characterized by tapered sides and tools for implantation of optimized solid substrates.

53 Claims, 27 Drawing Sheets

(51) Int. Cl.
- *A61F 2/30* (2006.01)
- *A61F 2/46* (2006.01)
- *A61F 2/28* (2006.01)
- *A61B 17/17* (2006.01)
- *A61L 27/20* (2006.01)
- *A61L 27/54* (2006.01)
- *A61L 27/56* (2006.01)
- *A61B 17/92* (2006.01)

(52) U.S. Cl.
CPC ...... *A61B 17/1633* (2013.01); *A61B 17/1675* (2013.01); *A61B 17/17* (2013.01); *A61B 17/1764* (2013.01); *A61F 2/28* (2013.01); *A61F 2/30756* (2013.01); *A61F 2/4618* (2013.01); *A61L 27/20* (2013.01); *A61L 27/54* (2013.01); *A61L 27/56* (2013.01); *A61B 2017/922* (2013.01); *A61F 2002/2835* (2013.01); *A61F 2002/2839* (2013.01); *A61F 2002/3021* (2013.01); *A61F 2002/3093* (2013.01); *A61F 2002/30276* (2013.01); *A61F 2002/30807* (2013.01); *A61F 2310/00341* (2013.01); *A61L 2300/414* (2013.01); *A61L 2430/02* (2013.01)

(58) Field of Classification Search
CPC ........ A61F 2002/30556; A61F 2/30767; A61F 2002/2835; A61F 2002/30014; A61F 2002/30604; A61F 2002/4475; A61F 2002/3006; A61F 2002/30067; A61F 2002/30125; A61F 2002/30126; A61F 2002/30146; A61F 2002/30159
See application file for complete search history.

(56) References Cited

U.S. PATENT DOCUMENTS

| | | | |
|---|---|---|---|
| 7,166,133 | B2 | 1/2007 | Evans et al. |
| 7,758,643 | B2 | 7/2010 | Stone et al. |
| 7,887,598 | B2 * | 2/2011 | Evans ................ A61L 27/12 623/23.51 |
| 9,668,754 | B2 | 6/2017 | Pfeiffer et al. |
| 10,080,570 | B2 | 9/2018 | Pfeiffer et al. |
| 2003/0135217 | A1 | 7/2003 | Buttermann et al. |
| 2003/0236573 | A1 | 12/2003 | Evans et al. |
| 2008/0249632 | A1 | 10/2008 | Stone et al. |
| 2009/0024174 | A1 * | 1/2009 | Stark ................ A61B 17/8625 606/321 |
| 2009/0110710 | A1 | 4/2009 | Evans et al. |
| 2013/0006248 | A1 | 1/2013 | Ellis |
| 2014/0065573 | A1 | 3/2014 | Wang |
| 2014/0180414 | A1 | 6/2014 | Pfeiffer et al. |
| 2017/0281198 | A1 | 10/2017 | Pfeiffer et al. |

OTHER PUBLICATIONS

International Preliminary Report on Patentability (Chapter II of the Patent Cooperation Treaty) for PCT/IL2016/050469; I.A. fd May 4, 2016, completed Apr. 11, 2017, by the European Patent Office, Munich, Germany.

Kon, E. et al., "A novel aragonite-based scaffold for osteochondral regeneration: early experience on human implants and technical developments," Injury (International journal of the care of the injured). Dec. 2016;47 Suppl 6:S27-S32. doi: 10.1016/S0020-1383(16)30836-1, Elsevier, Amsterdam, Netherlands.

Excerpted file history of U.S. Appl. No. 14/978,510, Altschuler et al., through Aug. 2, 2019.

* cited by examiner $\tau$ 2.00°

$\tau$ 2.00°

2.00°

Fig.8
A
B
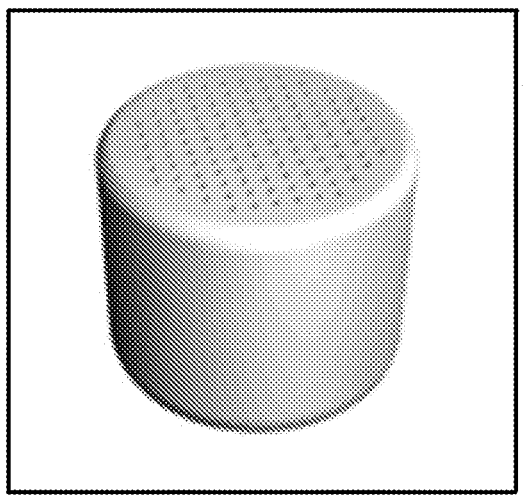
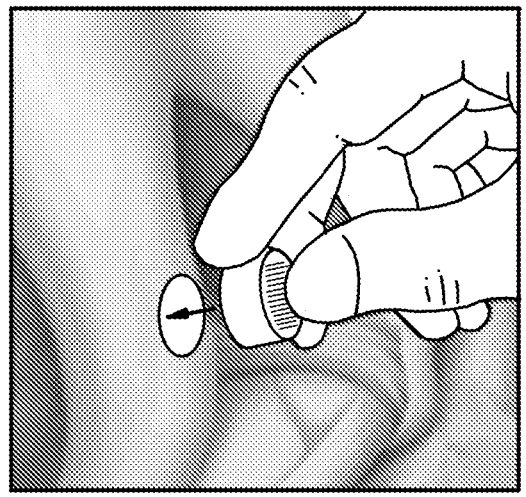
C
D
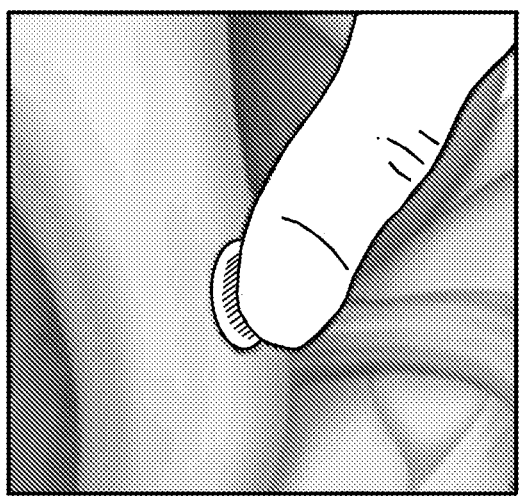
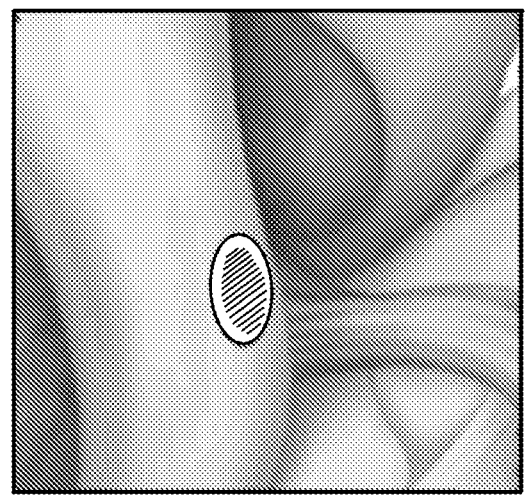

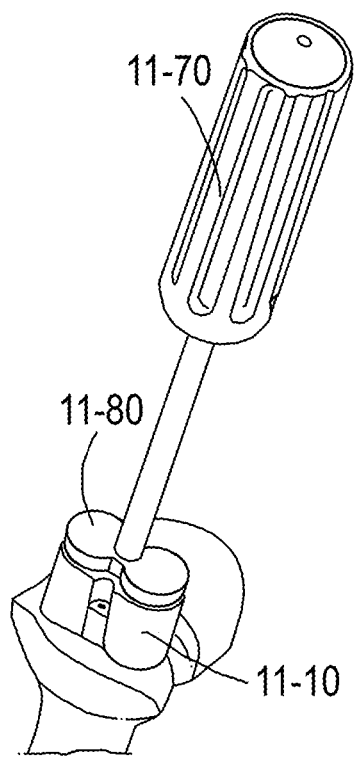
Fig.11K
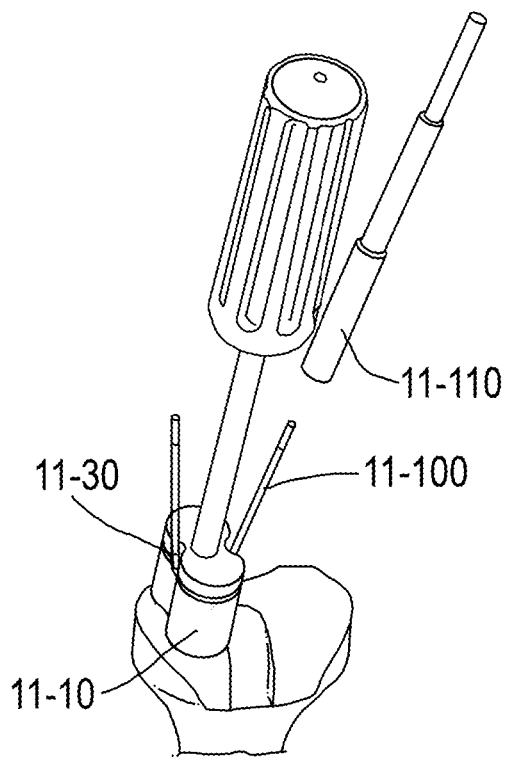
Fig.11L
Fig.11N
Fig.11M
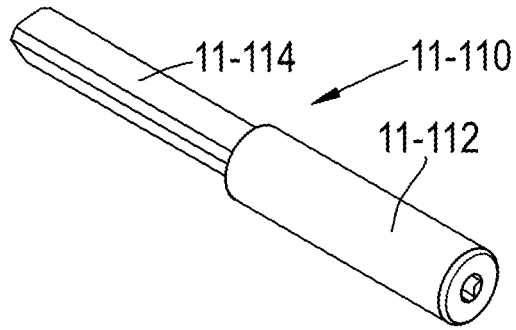
Fig.11O
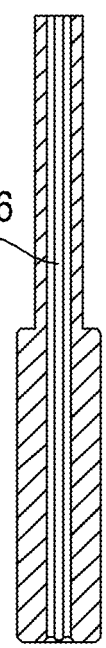

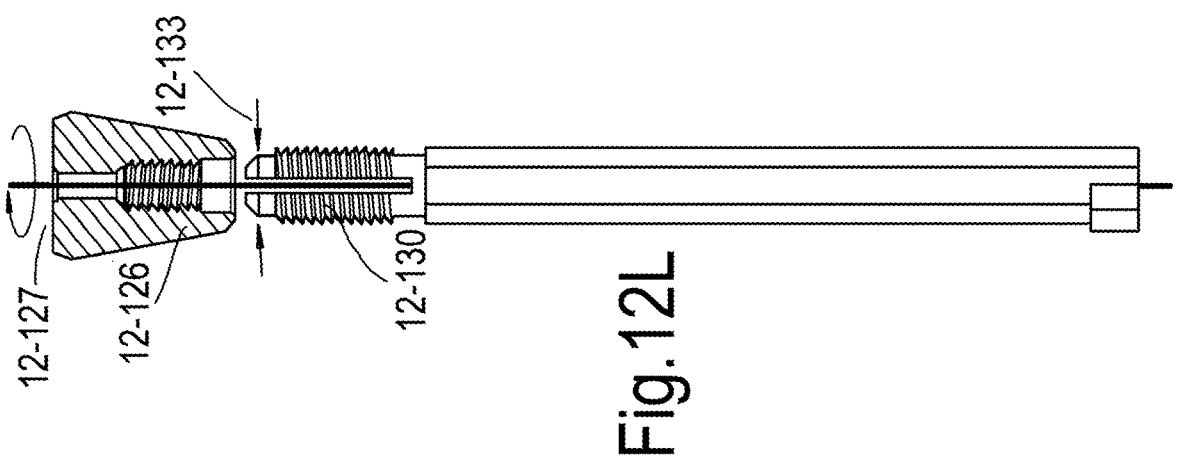
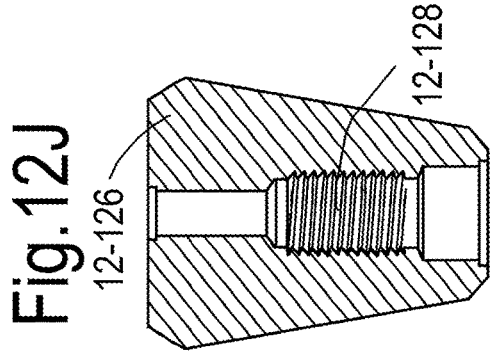
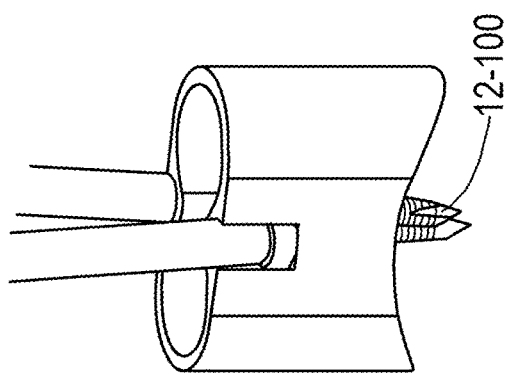
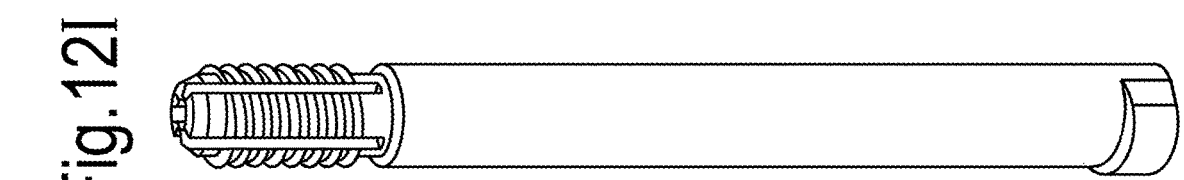
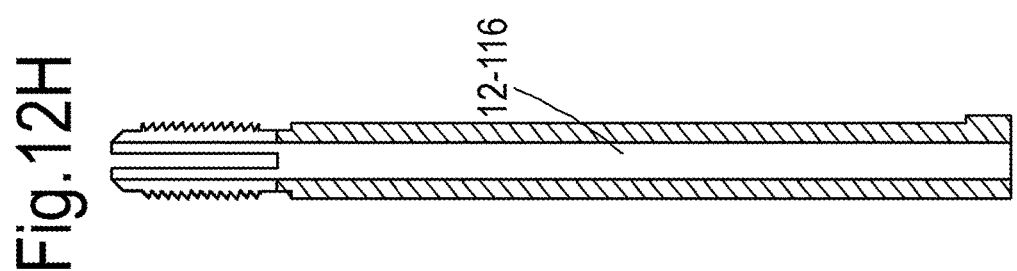
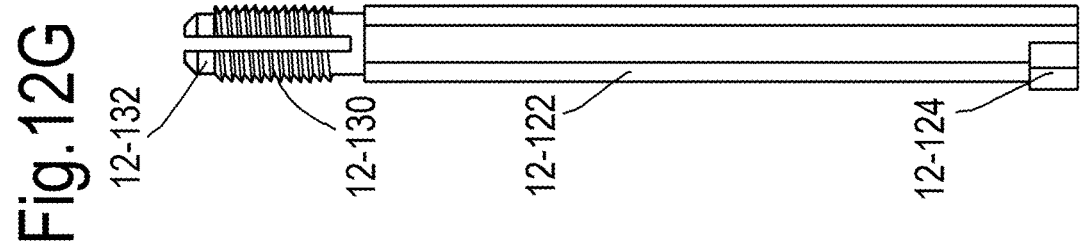

Fig.13A
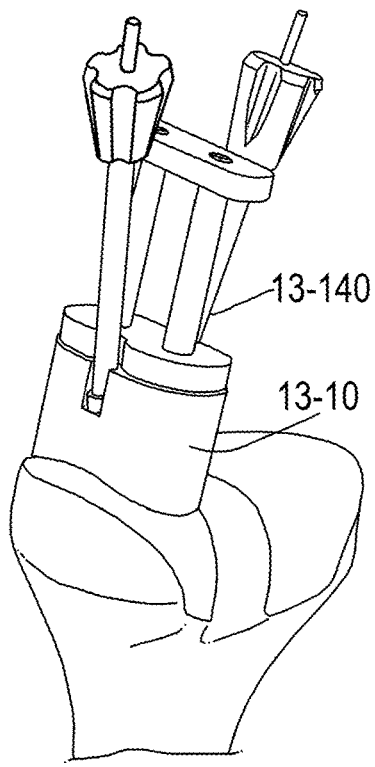
Fig.13B
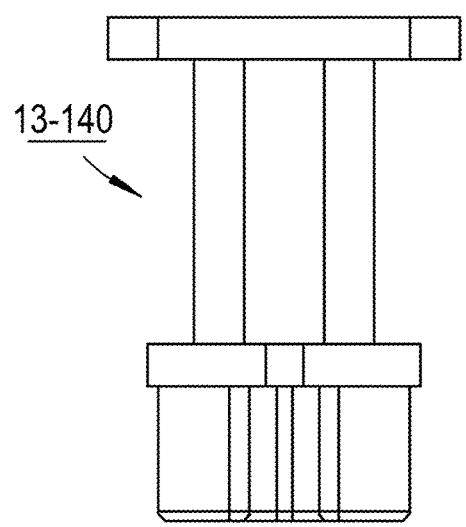
Fig.13C
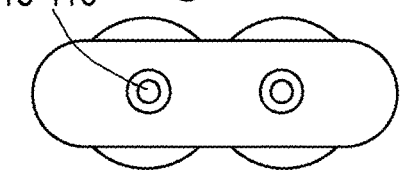
Fig.13D
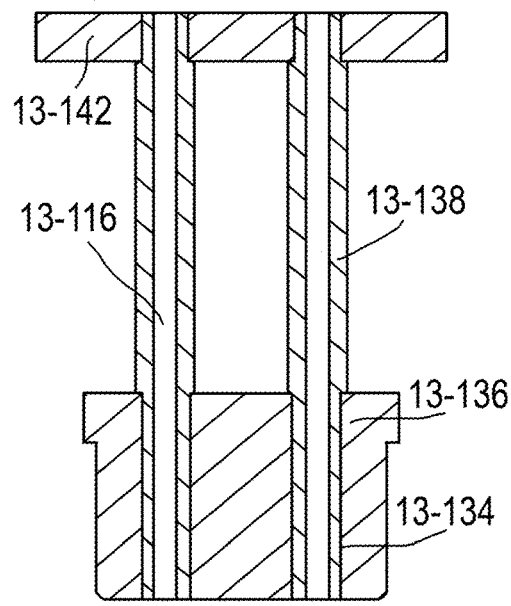
Fig.13-E
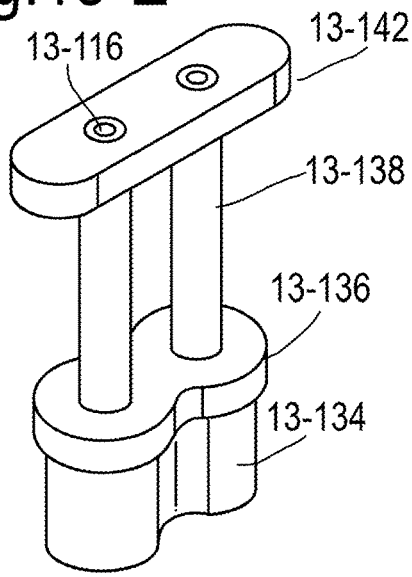

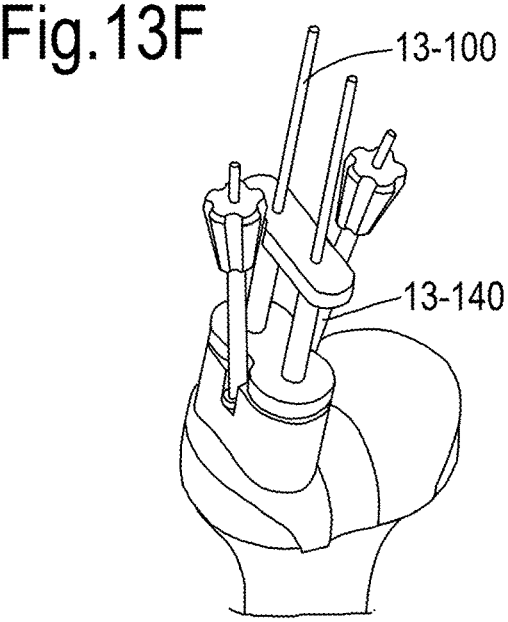
Fig.13F
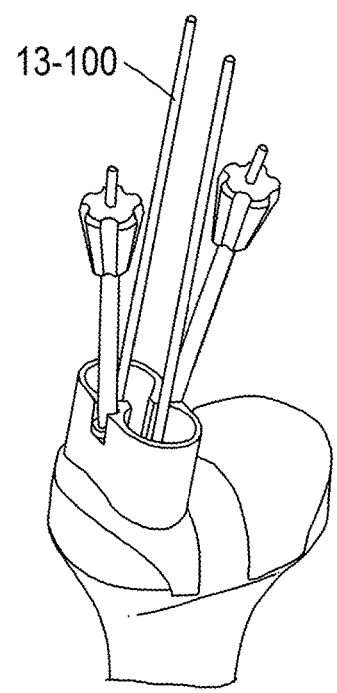
Fig.13G
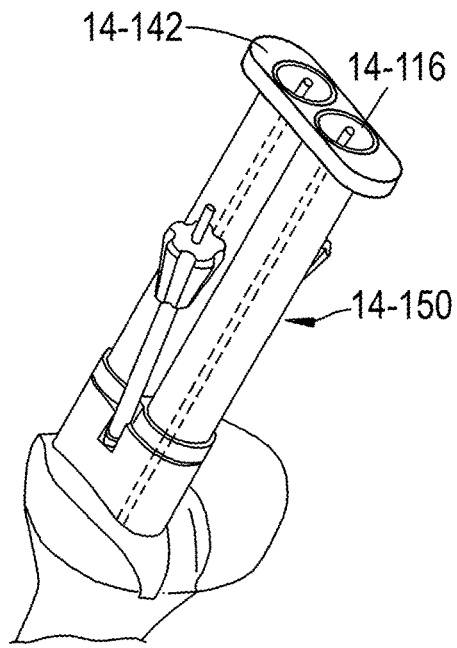
Fig.14A
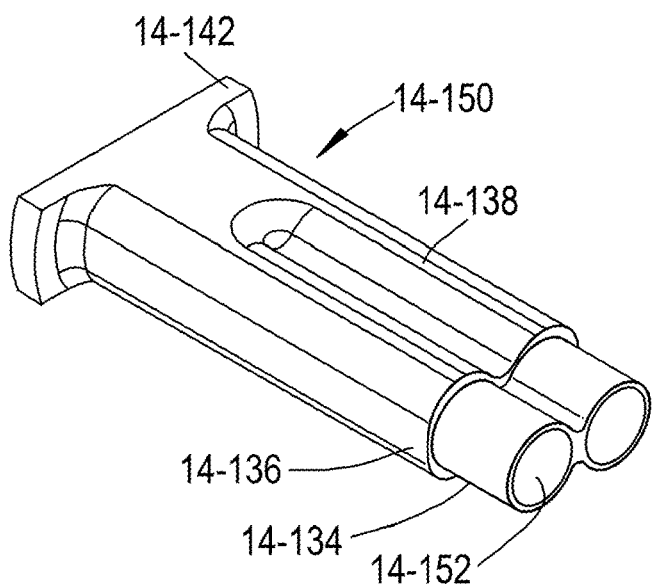
Fig.14.B

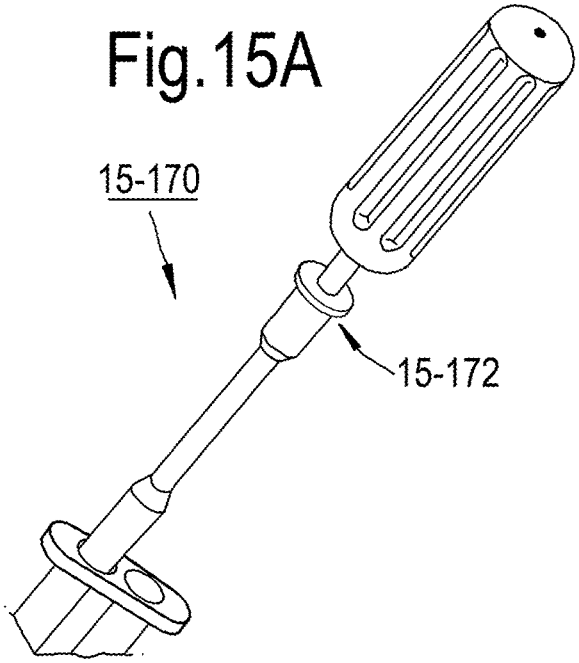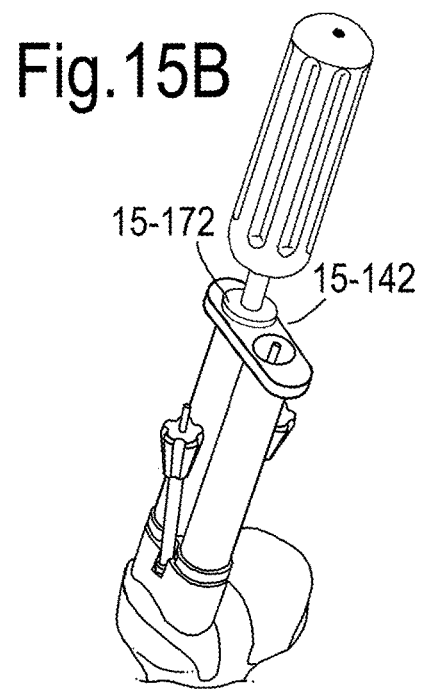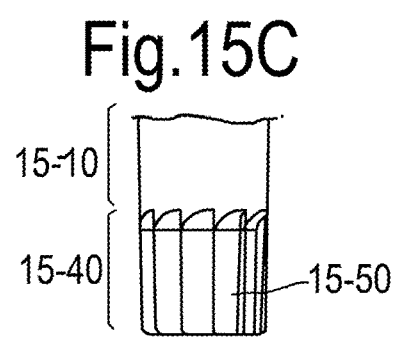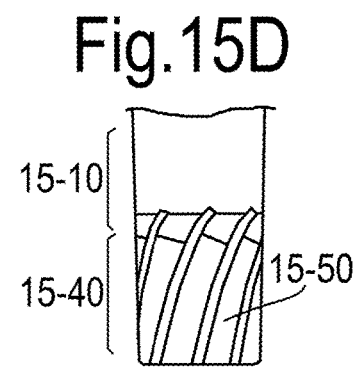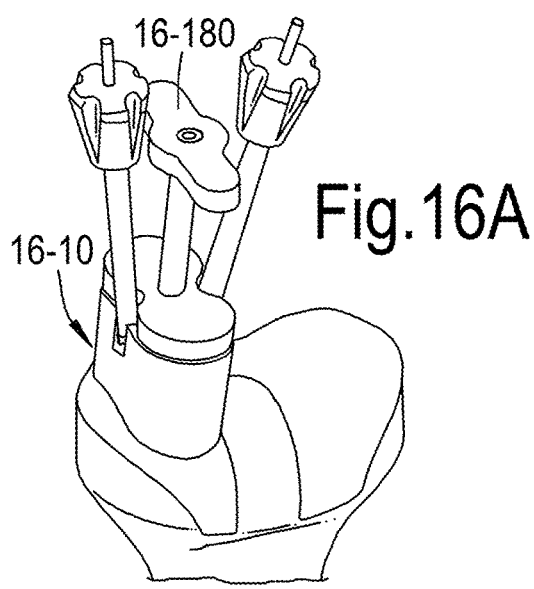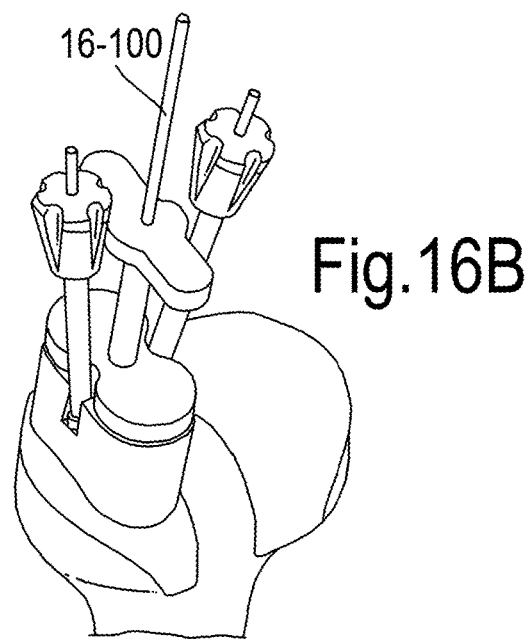

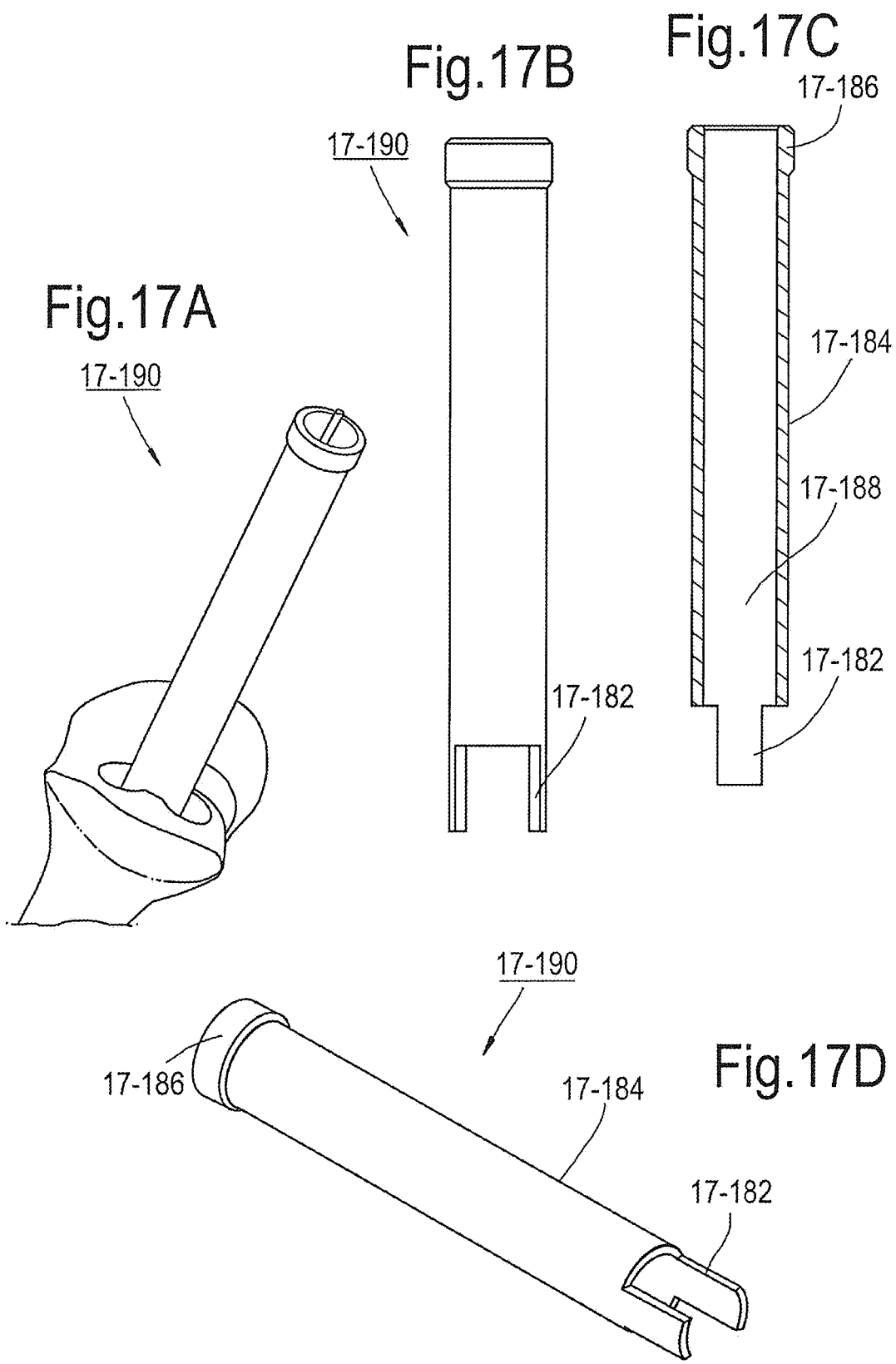

Fig.19.C
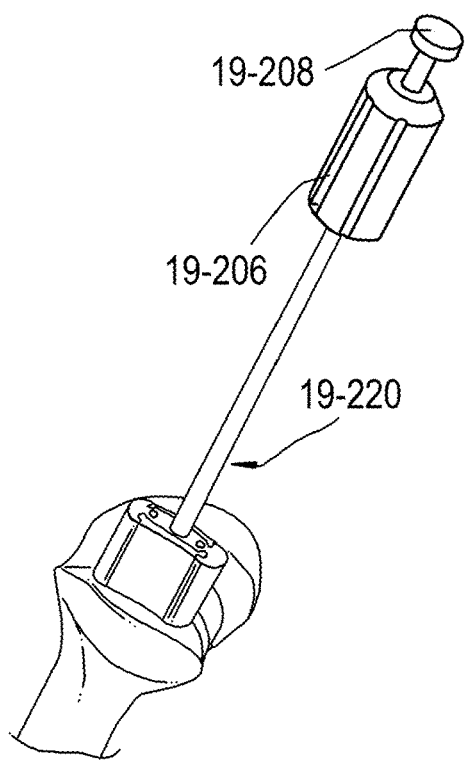
Fig.19D
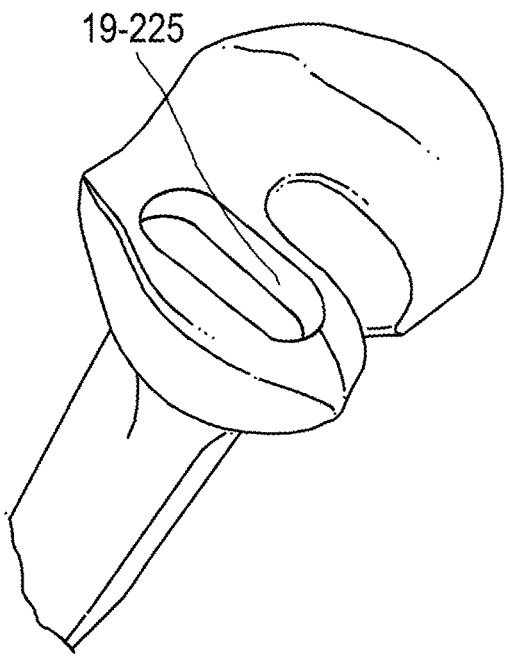
Fig.20A
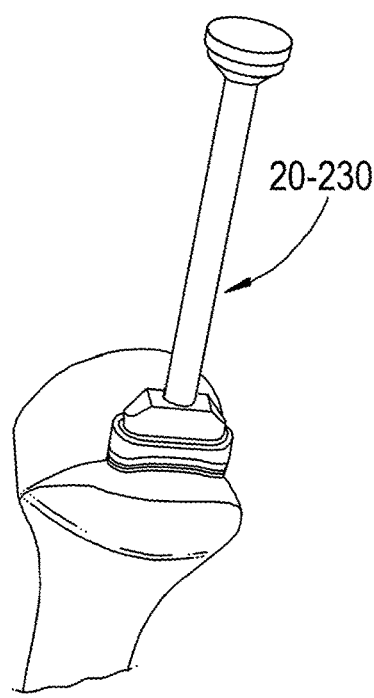
Fig.20B
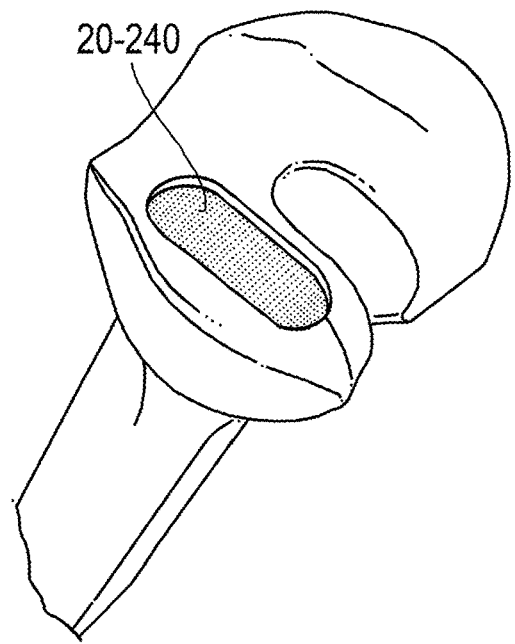

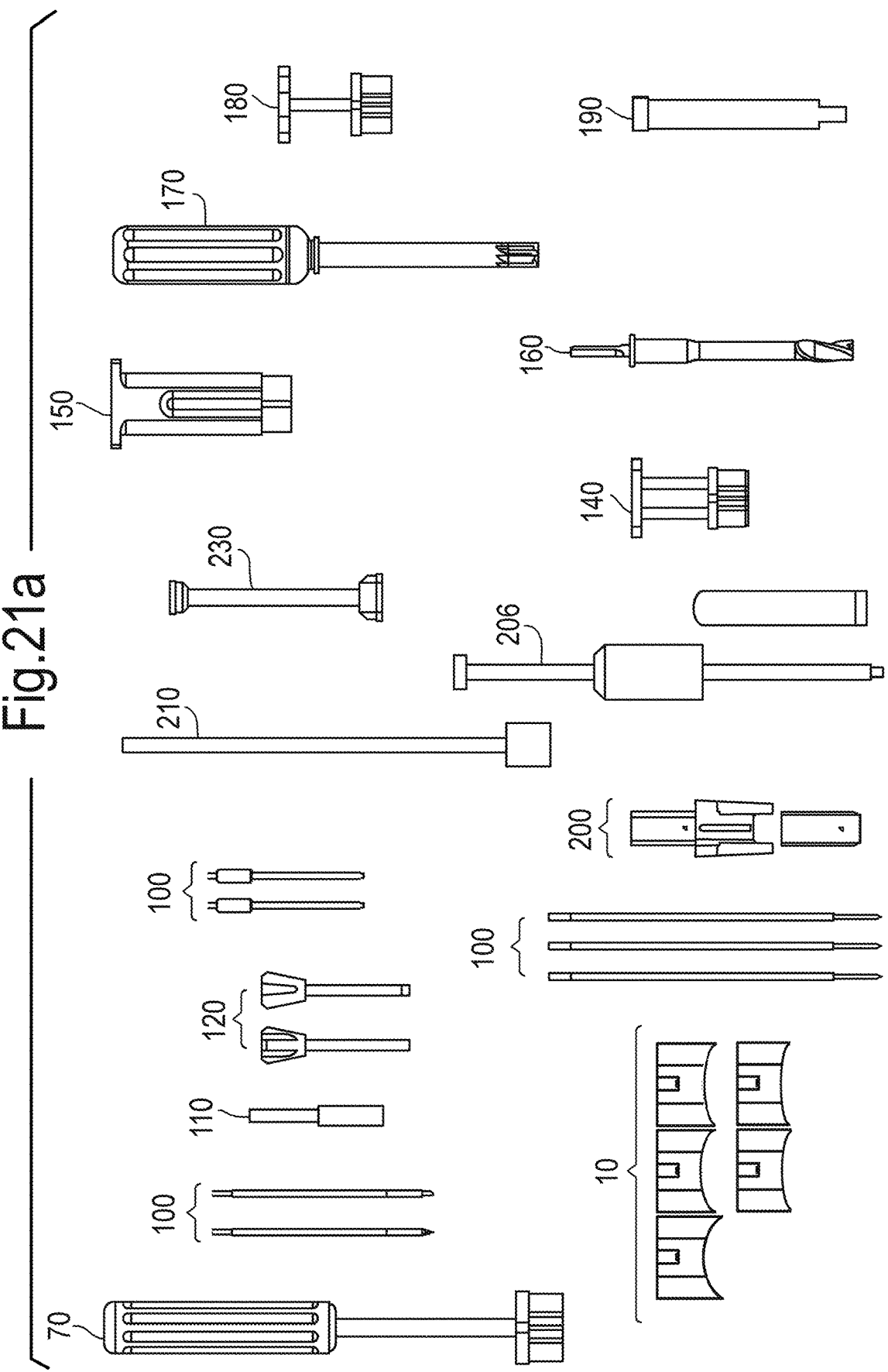

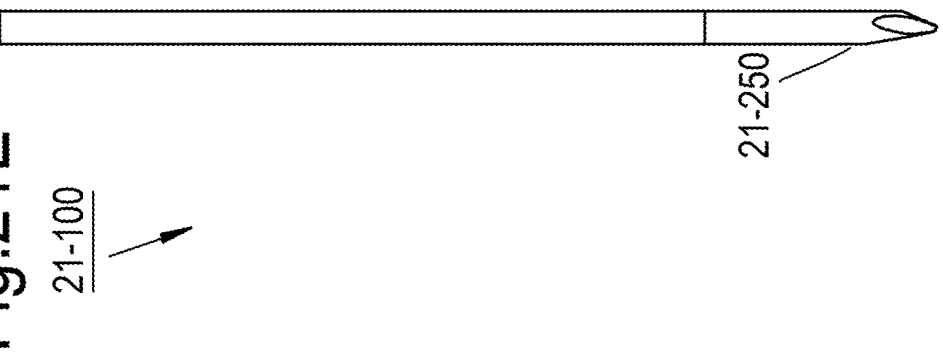
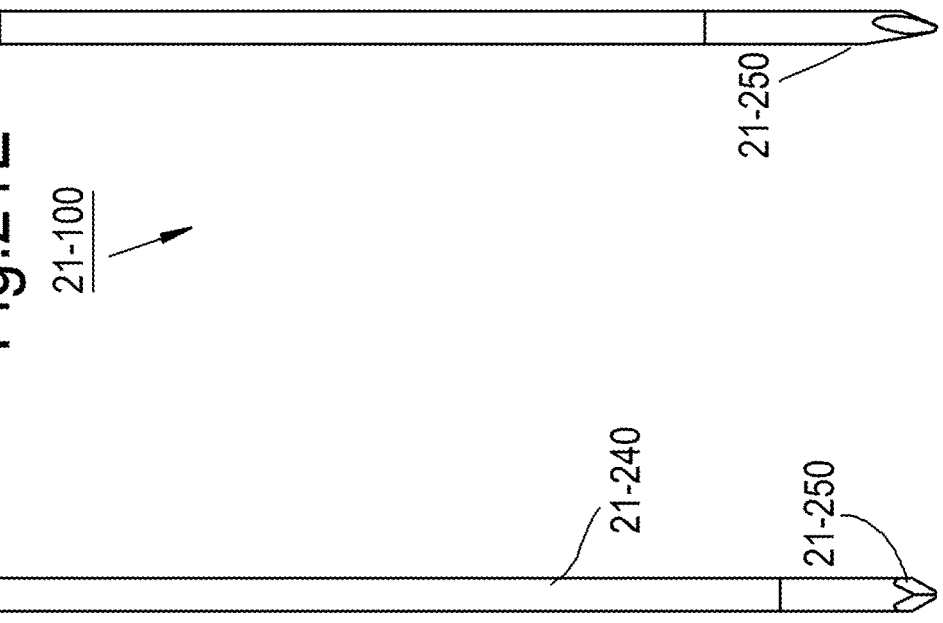

OPTIMIZED SOLID SUBSTRATES, TOOLS FOR USE WITH SAME AND USES THEREOF FOR PROMOTING CELL AND TISSUE GROWTH

CROSS-REFERENCE TO RELATED APPLICATIONS

This application claims the benefit of U.S. Provisional Application Ser. No. 62/157,485, filed May 6, 2015, and U.S. Provisional Application Ser. No. 62/331,471, filed May 4, 2016, each of which is fully incorporated herein by reference in its entirety.

BACKGROUND OF THE INVENTION

Tissue growth, regeneration and repair are often necessary to restore function and reconstruct the morphology of the tissue, for example, as a result of exposure to trauma, neoplasia, abnormal tissue growth, aging, and others.

Synthetic materials have also used as a substrate for promoting ex-vivo tissue assembly and repair, and similarly for restoring and reconstructing different tissues, for example for bone, for many years, with mixed success. Another possibility is autologous tissue grafting, although the supply of autologous tissue is limited and its collection may be painful, with the risk of infection, hemorrhage, cosmetic disability, nerve damage, and loss of function. In addition, significant morbidity is associated with autograft harvest sites. These problems may be overcome by engineering tissue using solid substrates made of synthetic or natural biomaterials that promote the adhesion, migration, proliferation, and differentiation of stem cells, for example, mesenchymal stem cells (MSCs).

Many diseases and conditions whose treatment is sought would benefit from the ability to promote cell and tissue growth in a site-specific manner, promoting growth and incorporation of new tissue within a damaged or diseased site.

In bone and cartilage applications, the immediate microenvironment and the three-dimensional (3D) organization are important factors in differentiation in general and particularly in chondrogenic and osteogenic differentiation.

Some bone tissue engineering scaffolds consists of natural polymers, such as collagen, alginate, hyaluronic acid, and chitosan. Natural materials offer the advantages of specific cell interaction, easy seeding of cells because of their hydrophilic interactions, low toxicity and low chronic inflammatory response. However, these scaffolds often are mechanically unstable and do not readily contribute to the creation of tissue structures with a specific predefined shape for transplantation. To obtain mechanical strength, chemical modification is required, which may lead to toxicity.

Defects and degeneration of the articular cartilage surfaces of joints causes pain and stiffness. Damage to cartilage which protects joints can result from either physical injury as a result of trauma, sports or repetitive stresses (e.g., osteochondral fracture, secondary damage due to cruciate ligament injury) or from disease (e.g. osteoarthritis, rheumatoid arthritis, aseptic necrosis, osteochondritis dissecans).

Osteoarthritis (OA) results from general wear and tear of joints, most notably hip and knee joints. Osteoarthritis is common in the elderly but, in fact, by age 40 most individuals have some osteoarthritic changes in their weight bearing joints. Another emerging trend increasing the prevalence of osteoarthritis is the rise in obesity. The CDC estimates that 30% of American adults (or 60 million people) are obese. Obese adults are 4 times more likely to develop knee OA than normal weight adults Rheumatoid arthritis is an inflammatory condition which results in the destruction of cartilage. It is thought to be, at least in part, an autoimmune disease with sufferers having a genetic predisposition to the disease.

Orthopedic prevention and repair of damaged joints is a significant burden on the medical profession both in terms of expense and time spent treating patients. In part, this is because cartilage does not possess the capacity for self-repair. Attempts to re-grow hyaline cartilage for repair of cartilage defects remain unsuccessful. Orthopedic surgery is available in order to repair defects and prevent articular damage in an effort to forestall serious degenerative changes in a joint. The use of surgical techniques often requires the removal and donation of healthy tissue to replace the damaged or diseased tissue. Techniques utilizing donated tissue from autografts, allografts, or xenografts are wholly unsatisfactory as autografts add additional trauma to a subject and allografts and xenografts are limited by immunological reactivity to the host subject and possible transfer of infective agents. Surgical attempts to utilize materials other than human or animal tissue for cartilage regeneration have been unsuccessful.

An ideal material which restores tissue function and facilitates reconstruction of the morphology of such tissue is as yet, lacking.

SUMMARY OF THE INVENTION

In some embodiments, the present invention provides optimized solid substrates for promoting cell or tissue growth or restored function. In some embodiments, the invention provides tools for use with same and methods of use of same.

In some embodiments, the invention provides an optimized solid substrate for promoting cell or tissue growth or restored function, which solid substrate comprises a coral or coral derivative, is characterized by a specific fluid uptake capacity value of at least 75% or is characterized by having a contact angle value of less than 60 degrees, when in contact with a fluid or which solid substrate is an allograft or autograft and which solid substrate is further characterized by tapered sides.

In some embodiments, the invention provides an optimized solid substrate for promoting cell or tissue growth or restored function, which solid substrate comprises a coral or coral derivative, is characterized by a specific fluid uptake capacity value of at least 75% or is characterized by having a contact angle value of less than 60 degrees, when in contact with a fluid or which solid substrate is an allograft or autograft and which solid substrate is further characterized by at least one substantially flat cross section at a terminus of said solid substrate and tapered sides.

In some embodiments, the invention provides an optimized solid substrate for promoting cell or tissue growth or restored function, which solid substrate comprises a coral or coral derivative, is characterized by a specific fluid uptake capacity value of at least 75% or is characterized by having a contact angle value of less than 60 degrees, when in contact with a fluid or which solid substrate is an allograft or autograft and which solid substrate is further characterized by comprising tapered sides at an angle of from 0.75 to about 4 degrees from a longitudinal axis along said solid substrate According to this aspect, and in some embodiments, the solid substrate is characterized by a conical or pyramidal frustum shape.

In some embodiments, the tapered sides are at an angle of from about 0.75 to about 4 degrees from a longitudinal axis along said solid substrate and in some embodiments, from about two degrees from a longitudinal axis along said solid substrate.

In some embodiments, the invention provides an optimized solid substrate for promoting cell or tissue growth or restored function, which solid substrate comprises a coral or coral derivative, is characterized by a specific fluid uptake capacity value of at least 75% or is characterized by having a contact angle value of less than 60 degrees, when in contact with a fluid or which solid substrate is an allograft or autograft and which solid substrate further comprises a curved surface, which curved surface has a radius of curvature approximating a radius of curvature of a tissue to which the solid substrate is being applied or implanted within.

In some embodiments, the coral or coral derivative is aragonite, calcite, mixtures thereof, or other polymorphs of the same. In some embodiments, the solid substrate is isolated from a *Porites* species, a *Goniopora*, a *Millepora* species or an *Acropora* species.

In some embodiments, the invention provides a solid substrate for promoting cell or tissue growth or restored function, which solid substrate is characterized by a specific fluid uptake capacity value of at least 75%, which specific fluid uptake capacity value is determined by establishing a spontaneous fluid uptake value divided by a total fluid uptake value.

In some embodiments, the invention provides a kit comprising a solid substrate as herein described.

In some embodiments, the invention provides a kit comprising a solid substrate as herein described and optionally any tool as herein described and optionally a biocompatible polymer, as herein described, wherein such biocompatible polymer may be applied to a solid substrate as herein described, wherein such application of the biocompatible polymer may be in situ, during implantation of such solid substrate, or such application of the biocompatible polymer may be during a preparation procedure of the solid substrate such that a solid substrate in a kit of this invention already comprises the biocompatible polymer incorporated therein.

In some embodiments, the invention provides a tissue shaper and alignment tool for implantation of an optimized solid substrate in a subject, said tissue shaper and alignment tool comprising:
  an elongated body having a central hollow spanning the length of said body;
  a shaping structure terminally joined to said elongated body by a joint region having a central hollow and further comprising:
    a first shaping region located proximal to said joint region, which first shaping region is substantially smooth and has parallel-oriented sides or sides tapered at an angle from a longitudinal axis of said tool; and
    a second shaping region located distal to said joint region, which second shaping region comprises a series of laterally extending protrusions, and has tapered sides at an angle from a longitudinal axis of said tool; and
  optionally a gripping handle, terminally joined to said elongated body by a joint region located distal to said shaping structure;

wherein said shaping structure is sized to be of a dimension to facilitate a snug fit within the borders of a site of implantation.

In some embodiments the lateral protrusions function as a series of dull blades, which when placed within and rotated within an implantation site, create a site with smooth walls, which have tapered sides at an angle from a longitudinal axis in said implantation site. In some embodiments, the tool comprises at least one lateral protrusion. In some embodiments, the tool comprises more than one lateral protrusion. In some embodiments, the tool comprises at least six lateral protrusions or in some embodiments, the tool comprises at least eight lateral protrusions, or in some embodiments, the tool comprises at least ten lateral protrusions, or in some embodiments, the tool comprises at least twelve lateral protrusions, or in some embodiments, the tool comprises at least four lateral protrusions, or in some embodiments, the tool comprises from two to six lateral protrusions. In some embodiments, the lateral protrusions have a long axis parallel to the longitudinal axis of the tool and in some embodiments, the lateral protrusions are angled with respect to the longitudinal axis of the tool. In some embodiments, the lateral protrusions are angled with respect to the longitudinal axis of the tool, at an angle from 1 to 15 degrees.

In some embodiments, the invention provides a kit comprising the tissue shaper and alignment tool as herein described.

In some embodiments, this invention provides a method for implantation of an optimized solid substrate for promoting cell or tissue growth or restored function in a subject in need thereof, said method comprising:
  isolating or preparing an optimized solid substrate for promoting cell or tissue growth or restored function, which solid substrate comprises a coral or coral derivative, is characterized by a specific fluid uptake capacity value of at least 75%, or is characterized by having a contact angle value of less than 60 degrees and which is further characterized by at least one substantially flat cross section at a terminus of said solid substrate and tapered sides;
  establishing a specific fluid uptake capacity value of said solid substrate, which specific fluid uptake capacity value is determined by establishing a spontaneous fluid uptake value divided by a total fluid uptake value;
  selecting a solid substrate characterized by a specific fluid uptake capacity value of at least 75% or is characterized by having a contact angle value of less than 60 degrees; and
  implanting said solid substrate characterized by a specific fluid uptake capacity value of at least 75% or is characterized by having a contact angle value of less than 60 degrees within a desired site in a subject, wherein said implanting is conducted at an angle from an axis perpendicular to the surface of the tissue site being thus treated.

In some embodiments, this invention provides a method for implantation of an optimized solid substrate for promoting cell or tissue growth or restored function in a subject in need thereof, said method comprising:
  Isolating or preparing an optimized solid substrate for promoting cell or tissue growth or restored function, which solid substrate comprises a coral or coral derivative, is characterized by a specific fluid uptake capacity value of at least 75%, or is characterized by having a contact angle value of less than 60 degrees and which is further characterized by comprising tapered sides at an angle of from 0.75 to about 4 degrees from a longitudinal axis along said solid substrate;

establishing a specific fluid uptake capacity value of said solid substrate, which specific fluid uptake capacity value is determined by establishing a spontaneous fluid uptake value divided by a total fluid uptake value;

selecting a solid substrate characterized by a specific fluid uptake capacity value of at least 75% or is characterized by having a contact angle value of less than 60 degrees; and implanting said solid substrate characterized by a specific fluid uptake capacity value of at least 75% or is characterized by having a contact angle value of less than 60 degrees within a desired site in a subject, wherein said implanting is conducted at an implant angle of from 0.75 to about 4 degrees from an axis perpendicular to the surface of the tissue site being thus treated.

In some embodiments, the method further comprises the step of:

inserting a rod-like structure within a target tissue implantation site in a subject, optionally with the aid of an implement orienting said rod-like structure to be in an orientation perpendicular to a plane of a surface of said target graft withdrawal or implantation site and in an orientation to be centralized within said implantation site;

drilling an area of tissue in said subject which is less than that of a desired tissue implantation site in an orientation perpendicular to a surface of said area of tissue, optionally with a drill bit adapted for application over said rod-like structure;

surgically excising tissue from an area of desired implantation, by optionally applying a surgical cutter over said rod-like structure;

shaping said area of desired implantation with the aid of a tissue shaper and alignment tool comprising:
  an elongated body having a central hollow spanning the length of said body;
  a shaping structure terminally joined to said elongated body by a joint region having a central hollow and further comprising:
    a first shaping region located proximal to said joint region, which first shaping region is substantially smooth and has parallel-oriented sides or sides tapered at an angle from a longitudinal axis of said tool; and
    a second shaping region located distal to said joint region, which second shaping region comprises a series of laterally extending protrusions, and has tapered sides at an angle from a longitudinal axis of said tool; and
  optionally a gripping handle, terminally joined to said elongated body by a joint region located distal to said shaping structure;
  wherein said shaping structure is sized to be of a dimension to facilitate a snug fit within the borders of a site of implantation;

and applying a tissue graft or solid implant within said area of tissue, optionally by inserting a cannulated implant within said area of desired implantation, over said rod-like structure;

wherein said shaping promotes creation of a site with tapered sides at an angle from a longitudinal axis through the site of implantation promoting ideal incorporation of said solid implant.

In some embodiments, the surgical cutter is a reamer.

In some embodiments, according to this aspect, the process further comprises the step of prior contacting said marine organism skeletal derivative-based solid material with a fluid for from 0.5-15 minutes to promote spontaneous fluid uptake of said fluid within said marine organism skeletal derivative-based solid material to arrive at said spontaneous fluid uptake value.

In some embodiments, according to this aspect, the process further comprises the step of prior contacting said marine organism skeletal derivative-based solid material with a fluid and applying negative pressure to said marine organism skeletal derivative-based solid material to promote maximal uptake of said fluid within said marine organism skeletal derivative-based solid material to arrive at said total fluid uptake value.

In some embodiments, according to this aspect, the specific fluid uptake capacity value is a function of change in weight in said marine organism skeletal derivative-based solid material.

In some embodiments, according to this aspect, the change in weight in said marine organism skeletal derivative-based solid material is due to absorbance of said fluid within interstices in said solid material, or in some embodiments, due to absorbance of said fluid within pores in said solid material.

In some embodiments, according to this aspect, the specific fluid uptake capacity value is a function of change in fluid volume of applied fluid to said coralline-based solid material.

In some embodiments, the method of this invention further comprises the step of contacting said solid substrate with cells or tissue.

In some embodiments, according to this aspect, the contacting promotes adhesion, proliferation or differentiation, or a combination thereof, of said cells or cells within said tissue.

In some embodiments, a fluid is a protein-containing, salt-containing or carbohydrate containing solution, or in some embodiments, the fluid is a biologic fluid, and in some embodiments, the biologic fluid is autologous or allogeneic with respect to a cell or tissue of a subject when said solid substrate is contacted with a cell or tissue of said subject. In some embodiments, the fluid is water.

In some embodiments, the solid substrate promotes cell or tissue growth or restored function in tissue damaged by trauma or disease. In some embodiments, the solid substrate promotes cell or tissue growth in tissue damaged by trauma or disease. In some embodiments, the solid substrate promotes cell or tissue growth or restored function in tissue of a subject afflicted with a defect or disorder or disease of the cartilage or bone or a combination thereof.

In some embodiments, this invention provides a curved alignment and positioning tissue extraction base, comprising:
  a basal surface having a radius of curvature complementary to a radius of curvature of a tissue to which said curved alignment and positioning tissue extraction base is being affixed;
  an outer boundary substantially ovoid in shape further comprising at least two externally located lateral extensions through which respective rod-like structures can be inserted; and
  at least two internally located hollowed regions spanning the length of said curved alignment and positioning tissue extraction base.

In some embodiments, this invention provides a locker comprising:

an elongated hollowed shaft;
a locking tip located at a first terminus of said elongated hollowed shaft, said locking tip comprising an externally located extension that inserts within a locking mechanism insertion structure within the curved alignment and positioning tissue extraction as herein described; and
a headpiece located at or attaching to a second terminus of said elongated hollowed shaft.

In some embodiments, this invention provides a perpendicular implantation aligner, comprising:
at least one elongated shaft comprising at least one central hollow spanning the length of said at least one elongated shaft;
a terminal grip having at least one hollow region spanning the length of said terminal grip and lining up with said at least one central hollow spanning the length of said at least one elongated shaft; and
an insertion base having at least one hollow region spanning the length of said insertion base and lining up with said at least one central hollow spanning the length of said at least one elongated shaft and further being substantially ovoid in shape and of a size capable of inserting within the curved alignment and positioning tissue extraction base as herein described.

In some embodiments, this invention provides a drill bit protective sheath, comprising:
at least one elongated shaft comprising at least one central hollow spanning the length of said at least one elongated shaft and sized to fit insertion of a drill bit and rotation of said drill bit therewithin;
a top portion having at least one central hollow spanning the length of said top portion and lining up with said at least one central hollow spanning the length of said at least one elongated shaft; and
an insertion base having at least one central hollow region spanning the length of said insertion base and lining up with said at least one central hollow spanning the length of said at least one elongated shaft and being of a size capable of inserting within the curved alignment and positioning tissue extraction base.

In some embodiments, this invention provides a contour cutter, comprising:
a central hollow, spanning a length of said contour cutter, through which a rod-like structure may insert;
an outer boundary substantially ovoid in shape; and
at least one blade structure which is slidingly attached to said outer boundary such that it may be raised and lowered within said contour cutter; and optionally
at least one hollowed housing for insertion of a second rod-like structure therethrough;

In some embodiments, this invention provides a tamper comprising:
a first region having an outer boundary substantially ovoid in shape and a basal surface comprising a radius of curvature complementary to a radius of curvature of a tissue to which said curved alignment and positioning tissue extraction base is being affixed and comprising a non-stick material on at least a portion of an exposed region of said basal surface;
a second region comprising a gripping part located distally to said first region; and
an elongated shaft positioned between said first region and said second region.

In some embodiments, this invention provides a kit comprising a curved alignment and positioning tissue extraction base as herein described, a locker as herein described, a perpendicular implantation aligner as herein described, a drill bit protective sheath as herein described, a contour cutter as herein described, a tamper as herein described and any combination thereof.

In some embodiments, such kits may further comprise a solid substrate for implantation in a subject and a biocompatible polymer for incorporation within said solid substrate which solid substrate may be applied in situ, or in some embodiments, such biocompatible polymer may already be incorporated within a solid substrate in a kit of this invention.

In some embodiments, this invention provides tools, which in turn comprise a surface characterized by a radius of curvature, which radius of curvature may in some embodiments, be substantially similar to a radius of curvature of a tissue surface to which a tool and/or solid substrate as herein described is being applied.

In some embodiments, such radius of curvature of a tool or solid substrate as herein described may vary along an X-axis of a surface plane of said tool or solid substrate.

It will be appreciated that reference to symmetry or asymmetry in the radius of curvature of a solid substrate and/or its inclusion in kits of this invention and/or use and/or methods implementing same, may reflect a choice in approximating a curved tissue structure that the solid substrate and/kits containing same of this invention and/or use and/or methods implementing same is meant to address. In some aspects such choice is derived specifically from sagittal and/or coronal sections imaged of a defect site and the same dimensions and characteristics as determined from same will be applied to arrive at the most optimal implant/substrate.

In some aspects, the symmetry or asymmetry of the radius of curvature of a surface of a solid substrate of this invention or in a kit or for use and/or in accordance with a method of this invention will reflect sagittal and/or coronal variance of a comparable tissue site, as determined.

It will similarly be appreciated herein that reference to X- and/or Z-axes herein refers to sagittal and/or coronal planes and include consideration of same.

In some embodiments, such radius of curvature of a tool or solid substrate as herein described may vary along a Z-axis of a surface plane of said tool or solid substrate and in some embodiments, such radius of curvature of a tool or solid substrate as herein described may vary along both an X-axis and a Z-axis of a surface plane of said tool or solid substrate.

In some aspects, the radius of curvature of a tool and/or solid substrate as herein described comprising same is specifically customized to suit a defined radius of curvature along an X-axis or Z-axis or combination thereof of a surface of a tissue to which such tool or substrate is being applied, as derived from topology assessments conducted of the surface of the tissue.

In some embodiments, such radius of curvature of a tool or solid substrate as herein described may vary along a Z-axis of a surface plane of said tool or solid substrate and in some embodiments, such radius of curvature of a tool or solid substrate as herein described may vary along both an X-axis and a Z-axis of a surface plane of said tool or solid substrate.

In some aspects, the radius of curvature of a tool and/or solid substrate as herein described comprising same is specifically customized to suit a defined radius of curvature along an X-axis or Z-axis or combination thereof of a surface of a tissue to which such tool or substrate is being applied, as derived from topology assessments conducted of the surface of the tissue.

All publications, patents, and patent applications mentioned herein are hereby incorporated by reference in their entirety as if each individual publication or patent was specifically and individually indicated to be incorporated by reference. In case of a conflict between the specification and an incorporated reference, the specification shall control. Where number ranges are given in this document, endpoints are included within the range. Furthermore, it is to be understood that unless otherwise indicated or otherwise evident from the context and understanding of one of ordinary skill in the art, values that are expressed as ranges can assume any specific value or sub-range within the stated ranges, optionally including or excluding either or both endpoints, in different embodiments of the invention, to the tenth of the unit of the lower limit of the range, unless the context clearly dictates otherwise. Where a percentage is recited in reference to a value that intrinsically has units that are whole numbers, any resulting fraction may be rounded to the nearest whole number.

BRIEF DESCRIPTION OF THE DRAWINGS

FIG. 8 schematically depicts the manual insertion of an implant as herein described within a desired implantation site.

FIGS. 11C, 11D, 11F and 11H depict top and elevated views of the jig base showing hollowed areas 11-60, which may also serve as insert regions for a handle as further described below and showing the region through which certain immobilizing structures.

FIGS. 11E, 11F, 11G and 11H depict embodied jig bases 11-10, where the tissue extraction base of the instrument (11-20) further contains an angle of curvature, which accommodates a curved tissue surface to which the jig base is being applied, which curvature is asymmetrical, as will be determined/suitable, based on the topology of the surface tissue to which the jig base is being applied.

FIGS. 11I-11J depict an embodied handle 11-70, which inserts within a jig base, which may be used to set and attach the jig base to the tissue site for implantation. FIG. 11I shows a side view of the handle, highlighting the stopper region 11-80 and a narrower region 11-90 that fits within the jig base. FIG. 11J shows a bottom view of the handle in FIG. 11I.

FIG. 11K depicts insertion of the handle within a jig base.

FIG. 11M depicts a specialized bit 11-110 containing a centralized hollow region 11-116, sized such that an immobilizing structure inserts therethrough, as shown. Referring to region 11-112, in some aspects, it provides for an extension of the tool, providing a more convenient length for ease of working with same. In some aspect, the proximal region 11-114 may have certain adaptations that facilitate ease of insertion of the tool, for example, into other standard tools of the trade, such as standard drill Jacob chucks. It will be appreciated that the proposed adaptations to the specialized bits may ease use of the tools/kits of this invention, but they are not critical components of same, and standard tools, bits and chucks may be used. In some aspects, the exemplified bits may facilitate faster drilling, since standardized equipment/adaptors are provided, such that additional chucks and adaptors are not necessary FIG. 11N is a cross section of the base region of the drill bit, which has a specialized internal structure which can more appropriately fit the immobilizing structure inserted therein, e.g. the K-wire. In some aspects, this aspect obviates the need to use an additional drill chuck, for example.

FIG. 11O depicts an embodied longitudinal section of the specialized bit 11-110. The specialized bit has a proximal region 11-114 to which a standard drill may be attached and a wider base region 11-112, which is distal to same.

FIGS. 12A-12L depict embodied lockers of this invention. In FIG. 12A, the locker 12-120 is inserted over the immobilizing structure 12-100 and locked into place, and in 12B the jig base handle is removed following locking of the jig base, affixing same to the desired tissue site. FIGS. 12C-12J depict various aspects of the locker, including the locker central hollow 12-116, which spans the shaft 12-122 and head piece 12-126; the locker terminal locking extension 12-124 on the shaft 12-122 that engages a complementary fastener structure, for example, a complementary slot positioned on the jig base, which facilitates locking the locker into place and preventing movement of the jig base or K-wire inserted therethrough. FIG. 12K provides an enlarged view of the insertion of the immobilizing structures through the jig base into the tissue below same, and insertion of the lockers 12-120 over the K-wire. FIGS. 12G-12K show that the locker shaft may comprise a terminal threaded region 12-130, with a fitted joint region 12-132, such that when the locker head piece 12-126 is fitted onto same, individual sections of the fitted joint region 12-132 may be brought closer together to effectively narrow the diameter of the hollow region 12-116 to more securely lock around the immobilizing structure fitted therethrough. The locker head piece 12-126 may also comprise a threaded region 12-128, which promotes the narrowing of the diameter of the hollow region as described. Referring to FIG. 12L, in some aspects, as the locker head piece 12-126 is screwed onto the threaded region 12-130 of the locker, e.g. for example turning along axis 12-127, the sides of the threaded region are brought closer, for example, at the arrows designated by 12-133, and this in turn more snugly catches the immobilizing structure located therewithin.

FIGS. 13A-E depict embodied aspects of a perpendicular implantation aligner 13-140 of this invention. As depicted in FIG. 13A, the aligner 13-140 fits within the jig base 13-10. FIGS. 13B and 13D show cut away longitudinal sections and FIG. 13C shows a top view of the aligner 13-140 containing hollows 13-116 spanning therethrough and the aligner base 13-134 which specifically inserts within a jig base, and stopper 13-136. A shaft or shafts 13-138 connect the perpendicular aligner base with the top handle 13-142. FIGS. 13F-13G depict the threading of two immobilizing structures 13-100 through the perpendicular aligner 13-140, and insertion of same within the underlying tissue and subsequent removal of the aligner.

FIGS. 14A-14H depict an embodied drill bit protective sheath and insertion of a drill bit therethrough. The protective sheath 14-150 in this aspect contains two barrels 14-138 through which an immobilizing structure, and drill bit may insert, as well as a top portion 14-142, barrels 14-138 and base 14-134. FIG. 14C shows a longitudinal section through the drill bit protective sheath shown in FIG. 14B. The base 14-134 of the drill bit protective sheath inserts within the jig base and the stopper structure 14-136 prevents unchecked advancement of same. The drill protective sheath will contain hollows 14-152 spanning through each top portion 14-142, barrels 14-138 and base 14-134, so that the immobilizing structures may insert therethrough. FIGS. 14D-14H depict insertion of a drill bit containing a central hollow 14-116 that spans the drill bit over the immobilizing structure and within the drill bit protective sheath.

FIGS. 15A-15D schematically depict embodied tissue shapers/reamers 15-170, which may be further modified to comprise a stopper structure, 15-172. The shapers/reamers of this invention may comprise certain terminal modification, whereby a first shaping region 15-10 is substantially smooth and a second shaping region 15-40 comprises a series of laterally extending protrusions 15-50, and has tapered sides at an angle of two degrees from a longitudinal axis of said tool. The laterally extending protrusions may be further angled (FIG. 15D), if desired.

FIG. 16A-16F schematically depict another embodied version of a perpendicular implantation aligner 16-180. In this aspect, the aligner 16-180 has a central hollow 16-116 spanning the length of the aligner, a base 16-134, which inserts within the jig base, and a stopper rim region 16-136, which prevents unchecked advancement of the aligner within the implant site. The aligner also has a shaft 16-138 connecting the base to the top 16-142 of the aligner 16-180. An immobilizing structure 16-100 may be inserted through the central void 16-116 in the aligner and embedded within the underlying tissue as described hereinabove. FIG. 16E-16F shows that following careful removal of the aligner, the immobilizing structure is placed at the midpoint between the two previously created voids in the underlying tissue, as seen in FIGS. 16E and 16F. The lockers 16-120 may then be removed and the jig base 16-10 removed, such that only the immobilizing structure remains (FIG. 16F).

FIGS. 17A-17G depict another embodied drill bit protective sheath, comprising terminal insertion anchors 17-182, a central hollow 17-188 within the shaft 17-184 and an upper rim 17-186, which may also serve as a stopper, as further described herein. The drill sleeve 17-190 is placed over the immobilizing structure 17-100, and within the drill sleeve hollow 17-188. Once drilling is complete, the drill bit and drill sleeve are removed, and only the immobilizing structure 17-100 remains within the implant site 17-15 (FIG. 17G).

FIGS. 19A-19D schematically depict removal of the contour cutter to produce a smooth ovoid implant site within a desired tissue site. A slide hammer 19-220 is depicted, containing a central hollow 19-116, which inserts over the immobilizing structure, a shaft 19-204 onto which a hammer 19-206 is slidingly attached, and stopper 19-208. The slide hammer 19-220 may further comprise a fitted insertion tip 19-205, which inserts in a fitted manner within a recess 18-203 (as depicted in FIG. 18C) in the contour cutter for ease of removal of the contour cutter.

FIG. 20A-20G schematically depict tamping of an implant within the smooth ovoid implant tissue site shown in FIG. 19D. The embodied tamper 20-230 has specialized terminal modifications suited for ideal implantation, i.e. to provide a curved surface. In FIGS. 20C-20G, the tampers handle region 20-232, shaft 20-234 and head region 20-236 are shown. The head region may comprise a flat terminus 20-238, attached to a curved non-stick component 20-240, and the angle of curvature is dictated by the curvature present in the curved non-stick component 20-240 (FIG. 20C). The head region may also comprises a curved terminus 20-238, to which is attached a curved non-stick component 20-240, and the angle of curvature is dictated by the curvature present in both the head region curved terminus as well as the curvature present in the curved non-stick component 20-240 (FIG. 20D). The curvature of the head region 20-236 may be symmetrical, as depicted in FIG. 20E or assymmetrical, as depicted in FIG. 20G, to accommodate a symmetrical or asymmetrical curved surface being treated, as herein described.

FIG. 21 A-E schematically depict a series of tools that can be combined within assorted kits for use in implantation as described herein. A series of curved alignment and positioning tissue extraction bases (10) are depicted, which vary in terms of their radius of curvature. A handle (70) for insertion within the jig bases is shown, as are immobilizing structures (100), also including 21-100, and lockers (120) and specialized bit (110) is shown. The aligners (140, 180) are shown, as are the drill bit protective sheaths (150, 190), as described. An embodied drill bit 160 is depicted as well. An embodied contour cutter (200) is shown as are the mallet (210) and slide hammer (206). An embodied tamper (230) is shown as well. FIGS. 21B-21E in particular provide additional embodiments of immobilizing structures, indicating the potential for varied length, and depicting top portion 21-260, shaft 21-240, and insertion point 21-250 and including pointed tips 21-250, or screw-like tips 21-260, or the inclusion of both on a single immobliziling structure.

DETAILED DESCRIPTION OF THE PRESENT INVENTION

This invention provides, inter alia, optimized solid substrates for promoting cell or tissue growth or restored function, tools for use with same and uses of same.

In some embodiments, the invention provides an optimized solid substrate for promoting cell or tissue growth or restored function, which solid substrate comprises a coral or coral derivative, is characterized by a specific fluid uptake capacity value of at least 75% or is characterized by having a contact angle value of less than 60 degrees, when in contact with a fluid and which is further characterized by tapered sides.

In some embodiments, the invention provides more generally for an optimized solid substrate for promoting cell or tissue growth or restored function, which solid substrate comprises a porous natural substrate, such as an allograft or autograft, or other suitable marine, plant or animal source material, which porous solid substrate is characterized by being absorptive of biologic fluids when implanted in situ, is of sufficient strength and hardness and useful in stimulating bone and/or cartilage repair and which substrate is further characterized by tapered sides.

In some embodiments, the invention provides more generally for an optimized solid substrate for promoting cell or tissue growth or restored function, which solid substrate comprises a any substrate suitable for implantation such as metal, PLGA, PGA, any appropriate carbon composite implant material, ceramic material, alginate-based implant, and others, as will be appreciated by the skilled artisan, which when implanted in situ, is of sufficient strength and hardness and useful in stimulating bone and/or cartilage repair and which substrate is further characterized by tapered sides.

In some embodiments, this invention provides an optimized solid substrate for promoting cell or tissue growth or restored function, which solid substrate is characterized by a specific fluid uptake capacity value of at least 75% or is characterized by having a contact angle value of less than 60 degrees, when in contact with a fluid and which is further characterized by having at least a surface of said substrate having a radius of curvature that is substantially similar to a radius of curvature of a tissue surface to which such solid substrate is being applied/implanted within.

According to these aspects and in some embodiments, any solid substrate as herein described may comprise a coral, or any other similar natural porous material which is plant or animal in source origin. In some aspects such substrate may comprise an allograft or autograft or xenograft. In some aspects, such substrate may comprise a plant material, such as bamboo.

In some aspects, the porous natural substrate may be acellular or further processed to be suitable for implantation within a human host.

Figure 1A:
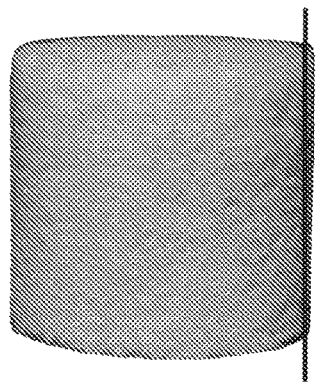
FIG. 1A shows a photograph of a prepared cylindrically shaped implant and the essentially parallel orientation of the sides with respect to a longitudinal axis of the implant.
Figure 1B:
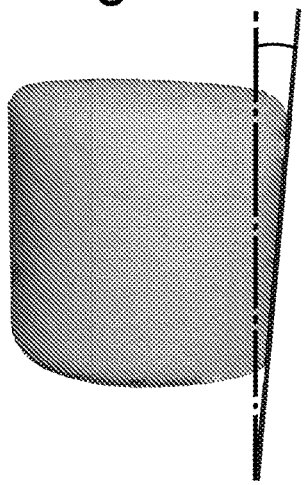
FIG. 1B shows a photograph of a prepared substantially conically shaped implant and the tapered orientation of the sides with respect to a longitudinal axis of the implant.
Figure 1C:
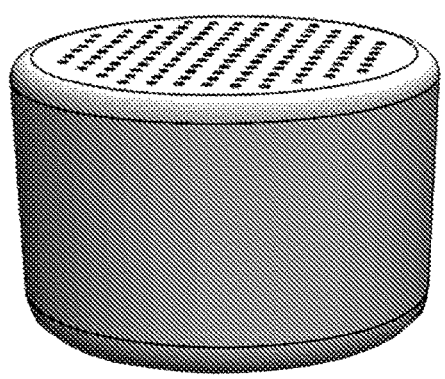
FIG. 1C provides a schematic representation of the implant in FIG. 1B.
Figure 1D:
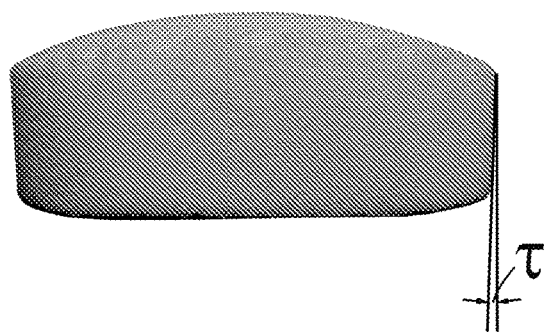
FIGS. 1D-1F depict and show photographs, respectively, of other embodied implants, which have tapered sides as viewed by the represented angle in these panels and an apical surface further modified to possess a desired radius of curvature. Similarly.
Figure 1E:
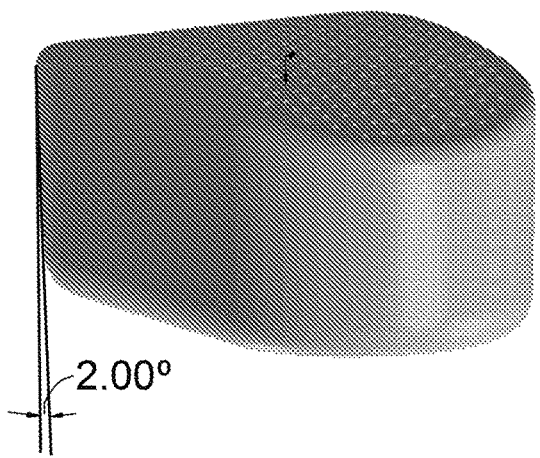
Figure 1F:
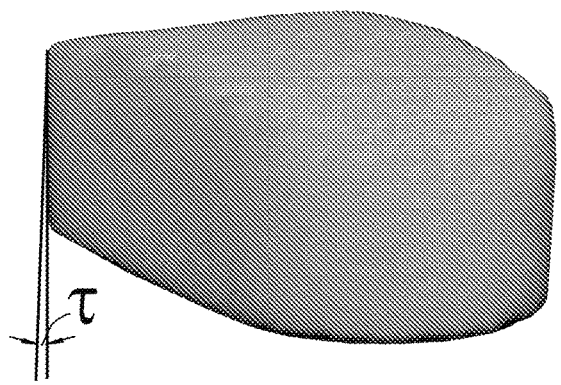
Figure 1G:
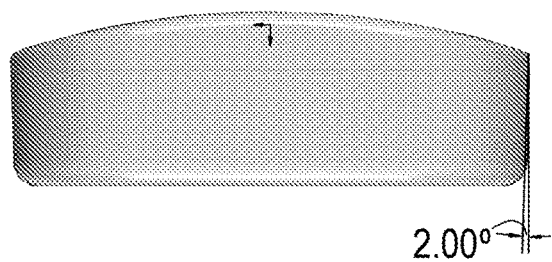
FIGS. 1G-1J show a photograph (1J), and schematically depict (1G-1I), respectively, other embodied implants, which optionally have tapered sides as depicted by the represented angle in the panel and various views of the implant are presented or depict implants where the implant apical surface is curved and such angle of curvature may be assymetrical, or symmetrical, as befitting the defect site each is intended to fill.
Figure 1H:
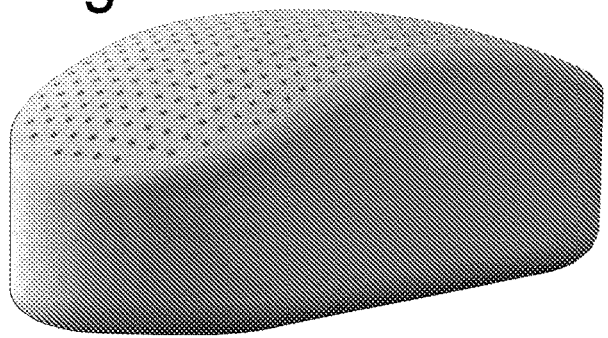
Figure 1I:
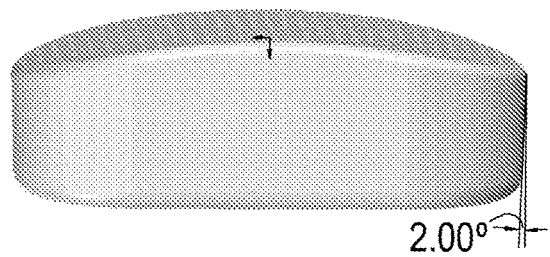
Figure 1J:
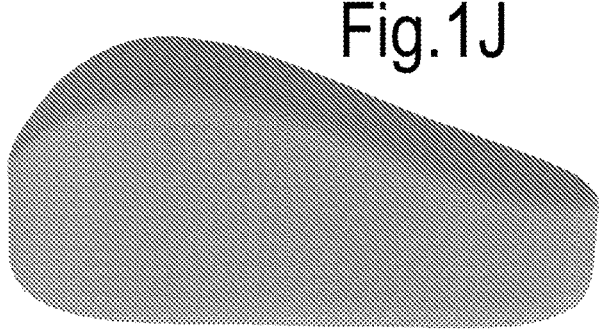

In some aspects, a solid substrate as herein described may be characterized by comprising tapered sides. In some embodiments, the term "tapered sides" refers to the sides of the solid implant being at an angle of from 0.75 to about 4 degrees from a longitudinal axis along said solid substrate. Referring to FIG. 1, comparing the photograph of an embodied substrate in FIG. 1B versus FIG. 1A, the sides of the substrate in FIG. 1B are clearly tapered in that a line parallel to a longitudinal axis along said solid substrate (gray line) is not parallel to a line following the contour of the side of the substrate (black line), whereas in FIG. 1A, the line following the contour of the side of the substrate is parallel to a longitudinal axis along said solid substrate. Similarly, the tapered sides can be readily observed in FIGS. 1E and 1I, as shown by the depicted angles presented in these panels.

In some aspects, the solid substrate will be characterized by at least one substantially flat cross section at a terminus of said solid substrate, as well.

In some aspects, the reference to being characterized by a substantially flat cross section of said solid substrate does not preclude the potential for rounded edges of the solid substrate, or in some embodiments, a slightly rounded top or bottom surface. In some embodiments, according to this aspect, the solid substrate may have slight bumps or other imperfections at either terminus. In some embodiments, according to this aspect, the solid substrate will be slightly rounded, but without a terminal point or pointed end or ends. In some embodiments, one terminus may be more rounded in appearance than another. In some embodiments, a terminus may be further characterized by the presence of a series of longitudinal channels or voids created therein, however, the top surface may still be considered to be substantially flat, as the surface in overall appearance will be substantially flat.

In some aspects, the solid substrate will have a substantially conical shape.

In some aspects, the term "a substantially conical" with regard to shape refers to a solid substrate characterized as above, with a shape approximating a cone in that it possesses a circular cross section at each terminus of the substrate, and tapered sides. In some aspects, the term "a substantially conical" precludes the presence of a terminal sharp point in the substrate, but does encompass a shape approximating a cone shape, whereby a pointy end is shaved or removed, leaving a circular cross section, tapered end in its stead.

According to this aspect, and in some embodiments, the solid substrate is characterized by a conical frustum shape.

According to this aspect, and in some embodiments, the solid substrate is characterized by a conical frustum shape, i.e. a portion of a solid cone that lies between two parallel planes cutting same. In some aspects, the diameter of the two parallel planes cutting the solid cone differs, such that one is larger and one is smaller. In some embodiments, the solid substrate characterized by a conical frustum shape will be further characterized by insertion of the solid substrate within an osteochondral defect such that the plane characterized with a smaller diameter is inserted first, such that the plane characterized by the larger diameter is most apically located within the implantation site.

In some aspects, the solid substrate will have a substantially pyramidal shape.

In some aspects, the term "a substantially pyramidal" with regard to shape refers to a solid substrate characterized as above, with a shape approximating a pyramid in that it possesses a flat cross section at each terminus of the substrate, and tapered sides. In some aspects, the term "substantially pyramidal" precludes the presence of a terminal sharp point in the substrate, but does encompass a shape approximating a pyramid shape, whereby a pointy end is shaved or removed, leaving a flat cross section, tapered end in its stead.

According to this aspect, and in some embodiments, the solid substrate is characterized by a pyramidal frustum shape.

According to this aspect, and in some embodiments, the solid substrate is characterized by a pyramidal frustum shape, i.e. a portion of a solid pyramid that lies between two parallel planes cutting same. In some aspects, the length/width of the two parallel planes cutting the solid pyramid differs, such that one is larger and one is smaller. In some embodiments, the solid substrate characterized by a pyramidal frustum shape will be further characterized by insertion of the solid substrate within an osteochondral defect such that the plane characterized with a smaller length/width is inserted first, such that the plane characterized by the larger length/width is most apically located within the implantation site.

In some embodiments, the solid substrate is characterized by a substantially ovoid shape, when referring to a shape regarding the boundaries or outer contour of the substrate. In some embodiments, the solid substrate has an overall shape that is ovoid or ellipsoid. In some embodiments, the solid substrate comprises an oval contour.

In some aspects, the solid substrate is characterized by any shape, that permits tapered sides, and in some embodiments, substantially flat termini, which can accommodate an ideal, optimized press fit within a defect site. In some aspects, the solid substrate will assume any appropriate geometry approximating a bar, cube, oval, with tapered sides, i.e. a solid shape substantially resembling for example, a bar, cube or oval, with two parallel planes cutting same.

In some aspects, the solid substrate is characterized by a shape with tapered sides as described, that can approximate the overall shape of a talus, great toe, shoulder, condyle, ankle, patella, trochlea, pelvis, vertebra, hip and others, as will be appreciated by the skilled artisan, or approximate a smaller piece of same that can insert within such structures readily, and in an optimized press fit manner.

In some aspects, the solid substrate may be characterized by having a first end with a diameter varying in size of between about 50-95% from that of a second diameter of the second end of the substrate, or in some embodiments, the solid substrate may be characterized by having a first end with a diameter varying in size of between about 50-65% from that of a second diameter of the second end of the substrate, or having a first end with a diameter varying in size of between about 55-75% from that of a second diameter of the second end of the substrate, having a first end with a diameter varying in size of between about 70-85% from that of a second diameter of the second end of the substrate, having a first end with a diameter varying in size of between about 75-95% from that of a second diameter of the second end of the substrate, having a first end with a diameter varying in size of between about 60-95% from that of a second diameter of the second end of the substrate, having a first end with a diameter varying in size of between about 65-95% from that of a second diameter of the second end of the substrate, having a first end with a diameter varying in size of between about 80-98% from that of a second diameter of the second end of the substrate having a first end with a diameter varying in size of between about 70-85% from that of a second diameter of the second end of the substrate.

In some aspects, the tapered sides are at an angle of two degrees from a longitudinal axis along the solid substrate.

In some aspects, the tapered sides are at an angle of 0.5 to 4.5 degrees from a longitudinal axis along the solid substrate. In some aspects, the tapered sides are at an angle of 0.5 to 4 degrees from a longitudinal axis along the solid substrate. In some aspects, the tapered sides are at an angle of 0.75 to 3.5 degrees from a longitudinal axis along the solid substrate, or in some embodiments, the tapered sides are at an angle of 1 to 3.25 degrees from a longitudinal axis along the solid substrate, or in some embodiments, the tapered sides are at an angle of 1.5 to 2.75 degrees from a longitudinal axis along the solid substrate, or in some embodiments, the tapered sides are at an angle of 1.75 to 4 degrees from a longitudinal axis along the solid substrate. Referring to FIG. 1B, an embodied solid substrate of the invention is shown, whereby the tapering of the lateral sides is evident, when viewed along a longitudinal axis drawn as depicted by the black bar spanning the implant.

Surprisingly, as described in studies conducted as described in Example 2 herein, implants defined as being substantially conical and with tapered sides at an angle of two degrees from a longitudinal axis of the implant, provided better results as compared to implants of identical composition yet varying structurally only in that their shape was substantially cylindrical, i.e. sides not tapered but essentially parallel to a longitudinal axis in the implant. Such improved results may, in some embodiments, be reflective of enhanced incorporation, diminished inflammation, diminished infection, greater surgical success, shorter implantation time, and other aspects, as will be appreciated by the skilled artisan.

It is important to note that while each coralline derived solid substrate evaluated in this context in terms of its promoting cell and/or tissue growth and restored tissue function yielded positive results, unexpectedly and surprisingly, when the implants were shaped such that their sides had a taper, which in this aspect, was a taper at an angle of about 0.75 to about 4 degrees from a longitudinal axis along said solid substrate, and in some embodiments, in particular at an angle of about 2 degrees, as described, such tapered substrates provided for significant, more consistent, improved incorporation and within an implantation site and other improved aspects/outcomes of the surgical procedures, for example, in terms of improved/faster cell and/or tissue growth and restored tissue function, or for example, improvement in terms of ease of and rapidity of incorporation, qualitative appearance, reduction of intra-operative complications in implanting same, reduction of time in implantation procedure and benefits related to same, and others.

Furthermore, in some aspects, such tapered solid substrates provided for greater potential for press fit insertion within a defect site, which in turn reduces many intraoperative complications associated with implantation within bone, cartilage or a combination thereof. In some embodiments, such advantages are particularly useful in implantation within osteochondral defects.

The solid substrates of this invention are characterized by a specific fluid uptake capacity value of at least 75%, which specific fluid uptake capacity value is determined by establishing a spontaneous fluid uptake value divided by a total fluid uptake value, or are characterized by having a contact angle value of less than 60 degrees, when in contact with a fluid. Methods for the determination of the specific fluid uptake and contact angle value have been described, for example, in PCT International Application Publication Number WO2014125478, hereby incorporated by reference in its entirety.

In some aspects, the solid substrate will be characterized by a curved cross section at a terminus of the solid substrate. According to this aspect, and in some embodiments, such curvature will be more typically at an apical surface of a solid substrate as herein described, in order to accommodate an appropriate fit of the implant, such that the correction of a defect containing a curved surface is readily accomplished. In some aspects, the curved surface of the defect site is substantially symmetrical and therefore the apical surface of the implant will comprise a substantially symmetrically curved surface. In some aspects, the curved surface of the defect site is substantially asymmetrical and therefore the apical surface of the implant will comprise a substantially asymmetrically curved surface.

In some embodiments, reference to a curved surface or curved cross section at a terminus of a solid substrate of this invention will include a radius of curvature of such substrate, where the radius may vary along an X-axis of a plane of a surface of such substrate, or in some embodiments, the radius may vary along a Z-axis of a plane of a surface of such substrate, or in some embodiments, radius may vary along an X-axis and a Z-axis of a plane of a surface of such substrate.

Similarly, and as described herein, reference to a curved surface or curved cross section at a terminus of a solid substrate of this invention will include a radius of curvature of such substrate, where the radius may vary along a coronal or sagittal plane of a surface of such substrate, or in some embodiments, such radius may vary along a lateral or anterior/posterior plane of a surface of such substrate, or in some embodiments, such radius may very along any axis as herein defined, along a surface of a substrate as herein described.

The solid substrates of this invention will, in some embodiments, comprise a coralline-based material. Coral, which is comprised of $CaCO_3$ in the crystalline form of aragonite or calcite has been shown to possess the advantage of supporting fast cellular invasion, adherence and proliferation. Coral has been shown to be an effective substrate for facilitation of the adherence, proliferation and differentiation of mesenchymal stem cells, and ultimate incorporation into cartilage and/or bone tissue. Coral has also been shown to serve as an excellent substrate for promoting adherence and proliferation of a number of other cell types, serving as an excellent support for cell and tissue growth.

The terms "coral" and "aragonite" and "calcite" may be used interchangeably herein.

In some embodiments, reference to an "implant" or "plug" or "solid substrate", as used herein refers to any embodiment or combined embodiments as herein described with regard to the solid substrates and to be considered as being included in the described aspect of this invention. For example, reference to a "solid substrate" as used herein, is to be understood to refer to any embodiment of a solid substrate as described herein being applicable for the indicated purpose or containing the indicated attribute, etc.

In one embodiment, "solid substrate" refers to a shaped platform used for cell and/or tissue repair and/or restored function, wherein the shaped platform provides a site for such repair and/or restored function. In one embodiment, the solid substrate is a temporary platform. In one embodiment, "temporary platform" refers to a natural degradation of a coral of this invention that occurs over time during such repair, wherein the natural fully or partially degradation of the coral may results in a change of solid substrate shape over time and/or change in solid substrate size over time.

In some embodiments, the solid implant is cannulated and in some embodiments, the solid implant is not cannulated.

It will be appreciated that different species of coral vary in terms of their average pore diameter and pore volume and the invention contemplates use of any such coral as a starting material for the preparation of the solid substrates as herein described, where the solid substrate is characterized in that it is characterized by a specific fluid uptake capacity value of at least 75%. As used herein, the term "pore volume" refers to volume or open spaces inside the porous scaffolding of this invention. Pore volume is determined by any means known in the art. Porosity can be calculated by standard methods, an example of which is provided further hereinbelow, see for example, Karageorgiou V, Kaplan D. (2005) "Porosity of 3D biomaterial scaffolds and osteogenesis" Biomaterials.; 26(27):5474-91, which is hereby incorporated by reference in its entirety.

It will be appreciated that the term "coral" will refer to a starting material from which aragonite, calcium carbonate, calcite, or hydroxyapatite etc. may be isolated.

In one embodiment, the solid substrates, processes and/or kits of this invention employ use of a coral. In one embodiment, the coral comprise any species, including, inter alia, *Porites, Acropora, Goniopora, Millepora*, or a combination thereof. In another embodiment the solid substrates, processes and/or kits of this invention employ use of nacre, mollusk shell, or bone morsels.

In one embodiment, the coral is from the *Porites* species. In one embodiment, the coral is *Porites Lutea*. In one embodiment, the coral is from the *Acropora* species. In one embodiment, the coral is *Acropora grandis*, which in one embodiment is very common, fast growing, and easy to grow in culture. Thus, in one embodiment *Acropora* samples can be easily collected in sheltered areas of the coral reefs and collection from the coral reefs can be avoided by use of cultured coral material.

In another embodiment, the coral is from the *Millepora* species. In one embodiment, the coral is *Millepora dichotoma*. In one embodiment, the coral has a pore size of 150 µm and can be cloned and cultured, making *Millepora* useful as a framework in the solid substrates, methods and/or kits of this invention.

In one embodiment, the coral is from the *Goniopora* species. In some embodiments, the coral is *Goniopora albiconus, Goniopora burgosi, Goniopora cellulosa, Goniopora ceylon, Goniopora ciliatus, Goniopora columna, Goniopora djiboutiensis, Goniopora eclipsensis, Goniopora fruticosa, Goniopora gracilis, Goniopora klunzingeri, Goniopora lobata, Goniopora mauritiensis, Goniopora minor, Goniopora norfolkensis, Goniopora palmensis, Goniopora pandoraensis, Goniopora parvistella, Goniopora pearsoni, Goniopora pendulus, Goniopora planulata, Goniopora polyformis, Goniopora reptans, Goniopora savignyi, Goniopora somaliensis, Goniopora stokes, Goniopora stutchburyi, Goniopora sultani, Goniopora tenella, Goniopora tenuidens* or *Goniopora viridis*.

In another embodiment, the coral is from any one or more of the following species *Favites halicora; Goniastrea retiformis; Acanthastrea echinata; Acanthastrea hemprichi; Acanthastrea ishigakiensis; Acropora aspera; Acropora austera; Acropora* sp. "brown digitate"; *Acropora carduus; Acropora cerealis; Acropora chesterfieldensis; Acropora clathrata; Acropora cophodactyla; Acropora* sp. "danai-like"; *Acropora divaricata; Acropora donei; Acropora echinata; Acropora efflorescens; Acropora gemmifera; Acropora globiceps; Acropora granulosa; Acropora* cf *hemprichi; Acropora kosurini; Acropora* cf *loisettae; Acropora longicyathus; Acropora loripes; Acropora* cf *lutkeni; Acropora paniculata; Acropora proximalis; Acropora rudis; Acropora selago; Acropora solitaryensis; Acropora* cf *spicifera* as per Veron; *Acropora* cf *spicifera* as per Wallace; *Acropora tenuis; Acropora valenciennesi; Acropora vaughani; Acropora vermiculata; Astreopora gracilis; Astreopora myriophthalma; Astreopora randalli; Astreopora suggesta; Australomussa rowleyensis; Coscinaraea collumna; Coscinaraea crassa; Cynarina lacrymalis; Distichopora violacea; Echinophyllia echinata; Echinophyllia* cf *echinoporoides; Echinopora gemmacea; Echinopora hirsutissima; Euphyllia ancora; Euphyllia divisa; Euphyllia yaeyamensis; Favia rotundata; Favia truncatus; Favites acuticollis; Favities pentagona; Fungia granulosa; Fungia klunzingeri; Fungia mollucensis; Galaxea acrhelia; Goniastrea edwardsi; Goniastea minuta; Hydnophora pilosa; Leptoseris explanata; Leptoseris incrustans; Leptoseris mycetoseroides; Leptoseris scabra; Leptoseris yabei; Lithophyllon undulatum; Lobophyllia hemprichii; Merulina scabricula; Millepora dichotoma; Millepora exaesa; Millipora intricata; Millepora murrayensis; Millipora platyphylla; Monastrea curta; Monastrea colemani; Montipora caliculata; Montipora capitata; Montipora foveolata; Montipora meandrina; Montipora tuberculosa; Montipora* cf *vietnamensis; Oulophyllia laevis; Oxypora crassispinosa; Oxypora lacera; Pavona bipartita; Pavona venosa; Pectinia alcicornis; Pectinia paeonea; Platygyra acuta; Platygyra pini; Platygyra* sp "green"; *Platygyra verweyi; Podabacia* cf *lanakensis; Porites annae; Porites cylindrica; Porites evermanni; Porites monticulosa; Psammocora digitata; Psammocora explanulata; Psammocora haimeana; Psammocora superficialis; Sandalolitha dentata; Seriatopora caliendrum; Stylocoeniella armata; Stylocoeniella guentheri; Stylaster* sp.; *Tubipora musica; Turbinaria stellulata*; or any coral known in the art, or a combination thereof.

In another embodiment, derivatives of marine animals—such as coral, sponges, mollusks shells and other related organisms may be used in the solid substrates, methods and/or kits of this invention may be Madreporaria, Helioporida of the order Coenothecalia, *Tubipora* of the order *Stolonifera, Millepora* of the order Milleporina, or others known in the art. In some embodiments, coral for use in the substrates, methods and/or kits of this invention may comprise scleractinian coral, including in some embodiments, *Goniopora* and others. In some embodiments, coral for use in the substrates, methods and/or kits of this invention may comprise *Alveopora*. In some embodiments, coral for use in the substrates, methods and/or kits of this invention may comprise bamboo corals, including in some embodiments, coral from the family Isididae, genera *Keratoisis, Isidella*, and others.

In one embodiment of this invention, the term "coral" refers to coral which is cut from a single piece of coral.

In one embodiment, coral may be machined into the described configurations, and quite complex shapes which are substantially conical, but for example, further modified to include or be shaped to include a threaded structure is envisioned and the same may be formed by appropriate machine or other processing, such as chemical processing.

In some embodiments, the solid substrate is scaled into a size/dimension so as to be most approximate to accommodate a site of desired tissue growth or repair.

In some embodiments, the solid substrate comprises a hollow or hollows along a Cartesian coordinate axis of said solid substrate.

In one embodiment, the size of coral solid substrates may be any size and/or any shape that would be useful for the purposes of the present invention, as would be known to one of skill in the Art depending on the purpose. For example and in one embodiment, the solid substrate may be substantially the same size as the structure it is meant to replace, while in another embodiment, the solid substrate or a portion thereof may be the size of a defect, fissure or fracture such that it may be placed therein to enhance/replace tissue formation/function in a discrete location. According to these aspects, it will be understood that the sides of such implant will have a taper with respect to a longitudinal axis through such implant.

In one embodiment, a coral for use in a solid substrate of this invention comprises an average void diameter, average pore size or a combination thereof appropriate for cell seeding and/or development of vasculature.

In one embodiment, coral is washed, bleached, frozen, dried, exposed to electrical forces, magnetic forces or ultrasound waves or microwaves or electromagnetic radiation or high pressure or a combination thereof prior to use thereof.

In some embodiments, the solid substrate is of a size and/or overall shape that is appropriate for the intended purpose, as will be appreciated by the skilled artisan. For example, and in some embodiments, solid substrates for use in osteochondral therapy or repair may make use of a substrate that has a diameter of about 5-15 mm, and a height of about 5-25 mm. In some embodiments, the solid substrate has a diameter of about 1-35 mm, and a height of about 1-45 mm, or about 5-40 mm, and a height of about 5-60 mm, or about 5-15 mm, and a height of about 5-45 mm. 5-30 mm, 15-60 mm, or larger. In some embodiments, the solid substrate has a height of about 5-40 mm. In some embodiments, the solid substrate has a height of about 1 cm to about 5 cm.

It will be appreciated by the skilled artisan that the size of the substrate may be so selected so as to be suitable to a particular application, for example, when using as a scaffolding material for bone repair, then the size may approximate the dimensions of a long bone in the subject. Accordingly, this invention is not to be limited by the size of the solid substrate.

It will be appreciated by the skilled artisan that the overall shape of the substrate may be so selected so as to be suitable to a particular application, for example, when using as a scaffolding material for condyle repair, then the shape may by curved in addition to being of the approximate dimensions of the regions of the condyle being repaired in the subject. Accordingly, this invention is not to be limited by the shape of the solid substrate.

In some embodiments, the coral for use in accordance with the instant invention may be prepared as described in PCT International Application publication Number WO 2009/066283, PCT International Application publication Number WO 2010/058400, PCT International Application publication Number WO 2010/146574 and PCT International Application publication Number WO 2010/146574, each of which is fully incorporated by reference herein, in its entirety.

A solid substrate of this invention is characterized by a specific fluid uptake capacity value as desired for the specific application for example of at least 75%, which specific fluid uptake capacity value is determined by establishing a spontaneous fluid uptake value divided by a total fluid uptake value.

In some embodiments, the fluid is a biologic fluid, which in some embodiments, is blood, and in some embodiments, the biologic fluid is water. In some embodiments, the biologic fluid is hydrophilic. In some embodiments the fluid is a plasma or plasma-containing solution. In some embodiments, the fluid is a protein-containing or carbohydrate-containing solution. In some embodiments the fluid is a salt-containing solution. In some embodiments, the solution is a glycoprotein-containing solution.

In some embodiments, the biologic fluid is autologous with respect to a cell or tissue of a subject when said solid substrate is contacted with such cell or tissue of said subject.

In some embodiments, the biologic fluid is a blood analog as herein defined.

In some embodiments, surprisingly, it was found that a solution containing 40% glycerol and 1 g/L glucose in normal saline was a useful fluid for evaluation of the specific fluid uptake capacity values of the solid substrates as herein described. In some embodiments, such solution is referred to as a "blood analogue" as its biocompatibility and other desirable characteristics, such as viscosity for the purpose of evaluating the specific fluid uptake capacity values of the solid substrates as herein described provides values as consistently as when autologous or allogeneic blood is used, or water and therefore can serve as an analogue for such screening protocols.

In some aspects, reference to a blood analogue herein will be understood to specifically refer to any solution containing from about 20 to about 60% glycerol and 1 g/L glucose in normal saline.

In some aspects, such blood analogue may further comprise a color indicator or dye, such as 1-D&C blue #2 Aluminum lake dye or FD&C blue #2 dye, or any other appropriate color indicator, as will be appreciated by the skilled artisan. In some embodiments, the blood analogue will comprise 1 g/L 1-D&C blue #2 Aluminum lake dye, or in some embodiments, the blood analogue will further comprise 0.075 g/L FD&C blue #2 dye, as these are convenient concentrations for the color indicator. It will be appreciated by the skilled artisan that the color indicator may be provided at any convenient concentration that provides a desired detectable signal.

It will be appreciated by the skilled artisan that the fluid for use in determining specific fluid uptake capacity values of the solid substrates as herein described may include any appropriate described fluid, for example, Salt based solutions such as physiologic Saline (0.9% NaCl), or in some embodiments, Carbohydrate based solutions such as Glucose 1 g/L in saline, or in some embodiments, Glucose 1 g/L in WFI, or in some embodiments, Glucose 10 g/L in WFI, or in some embodiments, a Protein based solution such as BSA 50 g/L in saline, or in some embodiments, BSA 5 g/L in in WFI, or in some embodiments, BSA 0.5 g/L in in WFI, or in some embodiments, a Glycerol based solution, such as, for example, 22% Glycerol in saline, or in some embodiments, 22% Glycerol in WFI, or in some embodiments, 30% Glycerol in WFI, or in some embodiments, 44% Glycerol in WFI, or in some embodiments, a Xanthan-Gum & Glycerol solution, such as, for example, 0.025% Xanthan-Gum+30% Glycerol in WFI, or in some embodiments, combinations of the above, for example, Glycerol/Glucose/BSA/saline/Skim milk, or in some embodiments, Glucose 0.1 g/dL+BSA 5 g/dL in saline, or in some embodiments, 5 g/dL skim milk in saline, or in some embodiments, 22% Glycerol+50 g/L skim milk in saline, or in some embodiments, 22% Glycerol+10 g/L Glucose in saline, or in some embodiments, 22% Glycerol+1 g/L Glucose in saline, or in some embodiments, 30% Glycerol+1 g/L Glucose in saline, or in some embodiments, 30% Glycerol+10 g/L Glucose in saline, or in some embodiments, 32.5% Glycerol+1 g/L Glucose in saline, or in some embodiments, 35% glycerol+1 g/L Glucose in saline, or in some embodiments, 35% Glycerol+1 g/L Glucose in saline, or in some embodiments, 40% Glycerol+1 g/L Glucose in saline, or in some embodiments, PEG/Tween 20/Gelatin such as, for example, 40% Glycerol+1 g/L Glucose in saline+1% PEG, or in some embodiments, 40% Glycerol+1 g/L Glucose in saline+0.1% PEG, or in some embodiments, 40% Glycerol+1 g/L Glucose in saline+0.1% PEG+0.1% Tween 20, or in some embodiments, 40% Glycerol+1 g/L Glucose in saline+0.1% PEG+0.1% Gelatin, and others, as will be appreciated by the skilled artisan.

It will also be appreciated by the skilled artisan that any such fluid for use in determining the specific fluid uptake capacity values of the solid substrates as herein described may also be considered to represent an envisioned "blood analogue" as herein described.

It will be understood that any of the above are considered for use in determining the specific fluid uptake capacity values of the solid substrates as herein described and may in part function as a type of blood analogue for the purpose of such determination. In some aspects, as a preferred embodiment of a blood analogue as referred to herein, such analogue will comprise 40% glycerol and 1 g/L glucose in normal saline and optionally will further comprise a color indicator as herein described.

In some aspects, the blood analog as herein described will be further characterized by the following characteristics: having a density of approximately 1.12 g/mL; and having a viscosity of approximately 4.57 mPa/sec at 25° C.

It will be understood that the biologic fluid may be any fluid which is biocompatible and whose incorporation is appropriate within a solid substrate for the desired application.

In some embodiments, the process further comprises the step of contacting the material with a fluid for from 2-15 minutes to promote spontaneous fluid uptake of said fluid within said coralline-based solid material to arrive at said spontaneous fluid uptake value. In some embodiments, the process may allow for the contacting of the material with a fluid for from 0.5-15 minutes, or in some embodiments, from 0.5-5 minutes, or in some embodiments, 10-60 minutes, or in some embodiments, from 60 to 90 minutes, or in some embodiments, other intervals, to promote spontaneous fluid uptake. The skilled artisan will appreciate that the amount of time for which the fluid is applied to determine the spontaneous uptake may be extended or shortened as a function of the dimensions and geometry of the sample substrate being assessed. In some embodiments, when a larger sample is being assessed, the process further comprises the step of contacting the material with a fluid for from 2-24 hours to promote spontaneous fluid uptake of said fluid within said coralline-based solid material to arrive at said spontaneous fluid uptake value. In some embodiments, establishing a specific fluid uptake capacity value of the solid substrate includes the step of contacting said solid substrate with a fluid for from 0.1-15 minutes, allowing for spontaneous fluid uptake of the fluid within the solid substrate to arrive at the spontaneous fluid uptake value.

In some embodiments, the process further comprises the step of contacting said solid material with a fluid and applying negative pressure to the solid implant material to promote maximal uptake of said fluid within said coralline-based solid material to arrive at said total fluid uptake value. In some embodiments, application of positive pressure is via the application of a vacuum to the substrate immersed in the fluid, promoting entry of the fluid therewithin.

In some embodiments, the process may further comprise the step of contacting the solid implant material with a fluid and applying positive pressure to same to promote maximal uptake of fluid within the solid implant material to arrive at said total fluid uptake value. According to this aspect, and in some embodiments, care will be taken to ensure that the application of pressure does not in any way compromise the structural integrity of the solid substrate.

In some embodiments, application of positive pressure is via any manual means, for example, via the use of any applicator, syringe, etc., gravitational pressure, and others, as will be appreciated by the skilled artisan. In some embodiments, application of positive pressure is via forced osmosis, centrifugation and others. In some embodiments, combinations of the described methods and others are envisioned.

In some embodiments, the solid substrate for promoting cell or tissue growth or restored function comprises a coralline or coralline derivative, or other appropriate solid implant material characterized by having a contact angle value of less than 60 degrees, when in contact with a fluid.

Methods for determining a contact angle are well known, and any appropriate method can be used.

In some aspects, the sample is further dried under vacuum and/or heated or pressurized or steam treated.

In some embodiments, for aspects relating to a specific fluid uptake capacity value, such value is a function of change in weight in the solid implant material.

According to this aspect and in some embodiments, the dry weight for each sample is recorded and fluid as described herein is added an assay container.

According to this aspect and in some embodiments, at least 1:1 ratio of the size of the sample in mm to the volume of fluid added in ml is applied to the container. In some embodiments, the amount of fluid applied is in excess, as compared to the sample size.

According to this aspect and in some embodiments, once the initial fluid uptake is assessed, according to this aspect and in some embodiments, the solid substrate sample is then brought into contact with the fluid and the weight of the solid substrate sample is assessed. In other embodiments the specific gravity is assessed by gradient centrifugation of by the Archimedean principle.

According to this aspect and in some embodiments, spontaneous fluid uptake is assessed and a spontaneous fluid uptake value is established, based on the change in weight of the sample.

According to this aspect and in some embodiments, the specific fluid uptake capacity value is a function of change in fluid volume of applied fluid to said marine organism skeletal derivative-based solid material. According to this aspect, spontaneous fluid uptake is assessed and a spontaneous fluid uptake value is established based on the complete uptake of the volume applied to the sample.

According to this aspect and in some embodiments, the process then further comprises contacting a significantly increased amount of fluid with the sample and applying pressure thereto to promote maximal fluid uptake to the total fluid uptake capacity of the sample.

According to this aspect and in some embodiments, as noted, such pressure may be either positive or negative pressure, and the application time is for a period of time sufficient to ensure maximal uptake of the applied fluid into the marine organism skeletal derivative sample.

According to this aspect and in some embodiments, such time may include an interval of from 0.5-60 minutes, or in some embodiments, when a larger sample is being assessed, such time may include an interval of from 2-24 hours to arrive at said spontaneous fluid uptake value. It will be appreciated that the time intervals recited herein are applicable for any embodiment with regard thereto as described herein. The skilled artisan will appreciate that the amount of time for which the fluid is applied to determine the full capacity fluid uptake may be extended or shortened as a function of the dimensions and geometry of the sample substrate being assessed.

According to these aspects, the total fluid uptake capacity is thus assessed and the specific fluid uptake capacity value is then determined.

In some embodiments, the invention specifically contemplates solid substrates having a specific fluid uptake capacity value exceeding the cutoff value of 75%, for the sample to be noted optimized as a solid substrate for promoting cell or tissue growth. It will be appreciated that the invention contemplates the stated cutoff value for promoting a reasonable value that reduces the presence of appreciable false positives, i.e. solid substrates that are not as optimal for the stated applications.

In some embodiments, the invention specifically contemplates solid substrates characterized by having a contact angle value of less than 60 degrees, when in contact with a fluid, for the sample to be noted optimized as a solid substrate for promoting cell or tissue growth. It will be appreciated that the invention contemplates the stated cutoff value for promoting a reasonable value that reduces the presence of appreciable false positives, i.e. solid substrates that are not as optimal for the stated applications.

In some embodiments, samples thus processed and found to be characterized by a specific fluid uptake capacity value of at least 75%, or specific selection of organism skeletal derivative-based solid substrates characterized by having a contact angle value of less than 60 degrees, when in contact with a fluid may then be used for the isolation of proximally located regions of a section from which such sample was taken, which samples can then be reliably used and considered as being optimized in accordance with the processes of this invention. In some embodiments, with regard to coral-based samples, such regions may include the entire annual growth ring region within the coral from which the sample was derived.

In some embodiments, samples thus processed and found to be characterized by a specific fluid uptake capacity value of at least 75%, or specific selection of organism skeletal derivative-based solid substrates characterized by having a contact angle value of less than 60 degrees, when in contact with a fluid, may then be dried fully and utilized for implantation into a subject or for use as an ex-vivo substrate for cell or tissue growth for subsequent implantation and then machined into the described substantially conical shapes as characterized herein.

In some embodiments, when the sample is utilized in vivo in subsequent applications, in some aspects, the sample is first contacted with autologous biological fluids or materials from the host prior to implantation into the same, verifying the observed enhanced fluid uptake phenotype as herein described.

In one embodiment of this invention, the solid substrate may further comprise an additional material.

In some embodiments, such additional material may include a polymer.

The term "polymer" refers, in some embodiments, to the presence of a layer of polymeric material in association with at least a portion of the solid substrate material. In some embodiments, such polymer layer is a coating for the solid substrate material.

In some embodiments, such coating may be over the entirety of the solid substrate, and in some embodiments, such coating may penetrate to within the voids and/or pores and/or hollows of the solid substrate. In some embodiments, such coating may be selectively applied to a particular region of the solid substrate, such that it creates a separate phase on the solid substrate, and in some embodiments, such polymer may be so applied that a thick polymer layer or phase is associated with a portion of a solid substrate, thereby creating a separate polymer phase in association with the solid substrate as herein described.

In one embodiment, the polymer coating provides added features to the solid substrates as herein described, for example, added tensile strength, added flexibility, reduced brittleness, and other attributes, to the solid substrate and in some embodiments, the polymer coating results in greater cellular attraction and attachment to the solid substrates as herein described, which in turn, inter alia, results in enhanced repair in terms of quantity, quality and timing of repair. In some embodiments, the polymer coating enhance cells proliferation and/or differentiation into desired mature tissue which in turn, inter alia, results in enhanced repair in terms of quantity, quality and timing of repair.

In one embodiment of this invention, a polymer coating is permeable. In one embodiment, the permeable polymer coating comprises a special porous membrane. In one embodiment, the term "permeable" refers to having pores and openings. In one embodiment, the permeable polymer coating of this invention has pores and openings which allow entry of nutrients, a therapeutic compound, a cell population, a chelator, or a combination thereof. In one embodiment, the permeable polymer coating of this invention has pores and openings which allow exit/release of nutrients, a therapeutic compound, a cell population, a chelator, or a combination thereof.

In one embodiment, a polymer coating of this invention is discontinuous. In one embodiment, a region or a plurality of sub-regions of the coral of this invention comprise an absence of polymer coating, allowing direct contact between the coral and the environment.

In some embodiments, the solid substrate incorporates a biocompatible polymer therewithin, which is associated with the aragonite or calcite component, via any physical or chemical association. In some embodiments, the polymer is a part of a hydrogel, which is incorporated in the solid substrates of this invention. In some embodiments, such hydrogel-containing solid substrates may thereafter be lyophilized or desiccated, and may thereafter be reconstituted.

In some embodiments of the solid substrates of this invention, the polymer may be applied to the solid substrate so as to form a separate phase, or in some embodiments, the polymer may be applied as a layer onto the solid substrate, or in some embodiments, the solid substrate may comprise both polymer as an internal or externally associated layer with a separate phase attached thereto comprising the same or a different polymeric material. In some embodiments, the biocompatible polymer is attached to an outer surface of the substrate. In some embodiments, the biocompatible polymer is present in a separate phase associated with a terminus of the solid substrate.

Such polymer-containing solid substrates may be particularly suited for cartilage repair, regeneration or enhancement of formation thereof. In some embodiments, according to this aspect, for example, in the treatment of osteochondral defects, the solid substrate is of a dimension suitable for incorporation within affected bone, and further comprises a polymer-containing phase, which phase, when inserted within the affected defect site, is proximal to affected cartilage. In another aspect and representing an embodiment of this invention, the solid substrate comprises a polymer, which has permeated within the voids and pores of the solid substrate, which solid substrate is inserted within a site of cartilage repair and which polymer facilitates cartilage growth, regeneration or healing of the defect site.

Such polymer-containing solid substrates may be particularly suited for bone repair, regeneration or enhancement of formation thereof. In some embodiments, according to this aspect, for example, in the treatment of bone edema, bone breakage or fragmentation, disease or defect, the coralline-based solid substrate is of a dimension suitable for incorporation within affected bone, and further comprises a polymer, which polymer has permeated within the voids and pores of the solid substrate, which solid substrate is inserted within the bone and which polymer facilitates bone growth, regeneration or healing of the defect site.

In one embodiment, a polymer coating of this invention comprises a natural polymer comprising, collagen, fibrin, elastin, silk, hyaluronic acid, sodium hyaluronate, cross linked hyalronic acid, chitosan, cross linked chitosan, alginate, calcium alginate, cross linked calcium alginate and any combinations thereof. In one embodiment, the biocompatible polymer comprises a natural polymer comprising a glycosaminoglycan, collagen, fibrin, elastin, silk, chitosan, alginate, and any combinations thereof.

In one embodiment, the polymer comprises synthetically modified natural polymers, and may include cellulose derivatives such as alkyl celluloses, hydroxyalkyl celluloses, cellulose ethers, cellulose esters and nitrocelluloses. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate and cellulose sulfate sodium salt.

In one embodiment, of this invention, a polymer comprises a synthetic biodegradable polymer. In one embodiment of this invention, a synthetic biodegradable polymer comprises alpha-hydroxy acids including poly-lactic acid, polyglycolic acid, enantioners thereof, co-polymers thereof, polyorthoesters, and combinations thereof.

In one embodiment, a polymer of this invention comprises a poly(cianoacrylate), poly(alkyl-cianoacrylate), poly (ketal), poly(caprolactone), poly(acetal), poly(α-hydroxy-ester), poly(α-hydroxy-ester), poly(hydroxyl-alkanoate), poly(propylene-fumarate), poly (imino-carbonate), poly(ester), poly(ethers), poly(carbonates), poly(amide), poly(siloxane), poly(silane), poly(sulfide), poly(imides), poly (urea), poly(amide-enamine), poly(organic acid), poly (electrolytes), poly(p-dioxanone), poly(olefin), poloxamer, inorganic or organometallic polymers, elastomer, or any of their derivatives, or a copolymer obtained by a combination thereof.

In one embodiment, a polymer of this invention comprises poly(D,L-lactide-co-glycolide) (PLGA). In another embodiment, the polymer comprises poly(D,L-lactide) (PLA). In another embodiment, the polymer comprises poly(D,L-glycolide) (PGA). In one embodiment, the polymer comprises a glycosaminoglycan.

In one embodiment, the polymer comprises synthetic degradable polymers, which may include, but are not limited to polyhydroxy acids, such as poly(lactide)s, poly(glycolide)s and copolymers thereof; poly(ethylene terephthalate); poly(hydroxybutyric acid); poly(hydroxyvaleric acid); poly[lactide-co-(ε-caprolactone)]; poly[glycolide-co-(ε-caprolactone)]; poly(carbonate)s, poly(pseudo amino acids); poly(amino acids); poly(hydroxyalkanoate)s; poly(anhydrides); poly(ortho ester)s; and blends and copolymers thereof.

In one embodiment of this invention, a polymer comprises proteins such as zein, modified zein, casein, gelatin, gluten, serum albumin, collagen, actin, α-fetoprotein, globulin, macroglobulin, cohesin, laminin, fibronectin, fibrinogen, osteocalcin, osteopontin, osteoprotegerin, or others, as will be appreciated by one skilled in the art. In another embodiment, a polymer may comprise cyclic sugars, cyclodextrins, synthetic derivatives of cyclodextrins, glycolipids, glycosaminoglycans, oligosaccharide, polysaccharides such as alginate, carrageenan (χ, λ, μ, κ), chitosane, celluloses, condroitin sulfate, curdlan, dextrans, elsinan, furcellran, galactomannan, gellan, glycogen, arabic gum, hemicellulose, inulin, karaya gum, levan, pectin, pollulan, pullulane, prophyran, scleroglucan, starch, tragacanth gum, welan, xanthan, xylan, xyloglucan, hyaluronic acid, chitin, or a poly(3-hydroxyalkanoate)s, such as poly(β-hydroxybutyrate), poly(3-hydroxyoctanoate) or poly(3-hydroxyfatty acids), or any combination thereof.

In one embodiment, the polymer comprises a bioerodible polymer such as poly(lactide-co-glycolide)s, poly(anhydride)s, and poly(orthoester)s, which have carboxylic groups exposed on the external surface as the smooth surface of the polymer erodes, which may also be used. In one embodiment, the polymer contains labile bonds, such as polyanhydrides and polyesters.

In one embodiment, a polymer may comprise chemical derivatives thereof (substitutions, additions, and elimination of chemical groups, for example, alkyl, alkylene, hydroxylations, oxidations, and other modifications routinely made by those skilled in the art), blends of, e.g. proteins or carbohydrates alone or in combination with synthetic polymers.

In one embodiment of this invention, the polymer is biodegradable. In one embodiment, the term "biodegradable" or grammatical forms thereof, refers to a material of this invention, which is degraded in the biological environment of the subject in which it is found. In one embodiment, the biodegradable material undergoes degradation, during which, acidic products, or in another embodiment, basic products are released. In one embodiment, bio-degradation involves the degradation of a material into its component subunits, via, for example, digestion, by a biochemical process. In one embodiment, biodegradation may involve cleavage of bonds (whether covalent or otherwise), for example in a polymer backbone of this invention. In another embodiment, biodegradation may involve cleavage of a bond (whether covalent or otherwise) internal to a side-chain or one that connects a side chain to, for example a polymer backbone.

In one embodiment, a solid substrate of this invention is covalently associated with the polymer coating via the use of a cross-linking agent. In one embodiment, the phrase "cross-linking agent" refers to an agent which facilitates the formation of a covalent bond between 2 atoms. In one embodiment, the cross-linking agent is a zero-length cross-linking agent.

In one embodiment, the cross-linking agent is (1 ethyl 3-(3dimethyl aminopropyl)carbodiimide (EDAC), N-Sulfohydroxy succinamide (Sulfo NHS), 5-iodopyrimidines, N-carbalkoxydihydroquinolines, pyrroloquinolinequinones, genipin or a combination thereof.

In one embodiment, the cross-linking agent is a homobifunctional cross-linker, such as, for example, a N-hydroxysuccinimide ester (e.g. disuccinimidyl suberate or dithiobis (succinimidylpropionate), homobifunctional imidoester (e.g. dimethyladipimidate or dimethyl pimelimidate), sulfhydryl-reactive crosslinker (e.g. 1,4-di-[3'-(2'-pyridyldithio) propionamido]butane), difluorobenzene derivative (e.g. 1,5-difluoro-2,4-dinitrobenzene), aldehyde (e.g. formaldehyde, glutaraldehyde), bis-epoxide (e.g. 1,4-butanediol diglycidyl ether), hydrazide (e.g. adipic acid dihydrazide), bis-diazonium derivative (e.g. o-tolidine), bis-alkylhalide, or a combination thereof.

In one embodiment, the cross-linking agent is a heterobifunctional cross-linker, such as, for example, an amine-reactive and sulfhydryl-reactive crosslinker (e.g. N-succinimidyl 3-(2-pyridyldithio)propionate, a carbonyl-reactive and sulfhydryl-reactive crosslinker (e.g. 4-(4-N-maleimidophenyl)butyric acid hydrazide), or a combination thereof.

In some embodiments, the cross-linking agent is a trifunctional cross-linkers, such as, for example, 4-azido-2-nitrophenylbiocytin-4-nitrophenyl ester, sulfosuccinimidyl-2-[6-biotinamido]-2-(p-azidobenzamido)hexanoamido] ethyl-1,3'-dithiopropionate (sulfo-SBED), or a combination thereof.

In another embodiment, the cross-linking agent is an enzyme. In one embodiment of this invention, the cross-linking agent comprises a transglutaminase, a peroxidase, a xanthine oxidase, a polymerase, or a ligase, or a combination thereof.

The choice of concentration of the cross-linking agent utilized for activity will vary, as a function of the volume, agent and polymer chosen, in a given application, as will be appreciated by one skilled in the art.

In one embodiment, the association of a solid substrate of this invention with a polymer coating of this invention comprises a physical and/or mechanical association. For example, in one embodiment, a physical and/or mechanical association may comprise imbibing of any means, air drying, using a cross-linking agent, applying of heat, applying vacuum, applying lyophilizing methods, freezing, applying mechanical forces or any combination thereof, to promote the physical association between a coral and a polymer coating as described herein.

In some embodiments, the choice of polymer, or application of polymer to a solid substrate as herein described may be so chosen, for an added ability to increase fluid uptake. Similarly, the surface of the solid substrate may be treated to increase fluid uptake therewithin, as well. In some embodiments, such surface treatment may include application of plasma to the solid substrate.

It will be apparent to one skilled in the art that the physical and/or chemical properties of a polymer application to a solid substrate of this invention and components thereof may influence methods of use of this invention and kits thereof, for inducing or enhancing cartilage and/or bone repair.

In one embodiment, the polymer as applied to the solid substrates of this invention has a thickness of between 2.0 μm and 0.1 μm. In one embodiment, the polymer coating has a thickness of about 1.0 μm. In one embodiment, the polymer coating of this invention has a thickness of between 10 μm and 50 μm. In one embodiment, the polymer coating as applied to the solid substrates of this invention has a thickness of about 10-25, or about 15-30, or about 25-50 μm. In one embodiment, the polymer coating as applied to the solid substrates of this invention has a thickness of about 0.0001-0.1 μm. In one embodiment, the polymer coating as applied to the solid substrates of this invention has a thickness of about 20-200 μm. In one embodiment, the polymer coating as applied to the solid substrates of this invention has a thickness of about 100-1500 μm.

In some embodiments, the polymer as applied to the solid substrates of this invention is a thin coating, which is associated with the solid substrates of this invention and has a thickness as indicated hereinabove.

In some embodiments, the polymer as applied to the solid substrates of this invention is applied throughout the solid substrates of this invention, such that, in some embodiments, the pores and voids within the solid substrates of the invention may be filled with polymers as herein described, and such polymer layer as applied may have a thickness of about 60-900 μm.

In some embodiments, the polymer is applied to an apical surface of an implant, in situ, as part of an implantation procedure of this invention.

In some embodiments, a kit of this invention will comprise a solid substrate as herein described which incorporates a polymer as described. In some embodiments, a kit of this invention will comprise a solid substrate as herein described, and a separate container comprising a biocompatible polymer for application to the solid substrate, wherein such biocompatible polymer may be applied to the solid substrate just prior to implantation, or in some embodiments, such biocompatible polymer may be applied to the solid substrate, in situ, during or immediately following implantation of the solid substrate in the affected subject.

In some embodiments, such kits may further comprise any tool useful in the implantation procedure of the solid substrate as described herein, and optionally, further comprising tools for the application of the biocompatible polymers as herein described.

In some embodiments, the polymer as applied to the solid substrates of this invention is to a terminus or a portion of the coating forming an additional polymer phase on the solid substrates of the invention. According to this aspect, and in some embodiments, the polymer layer as applied will have a thickness of between about 0.1-10 mm.

In some embodiments, multiple solid substrates comprising polymeric additives are implanted into a desired implantation site, wherein the polymer thickness applied to a first solid substrate may vary as compared to a polymer thickness as applied to a second solid substrate, implanted in the desired site. Variations in such thickness may reflect the range described herein.

In one embodiment, the thickness of the polymer as applied to the solid substrates of this invention influences physical characteristics of a solid substrate of this invention. For example, the thickness of a polymeric application may influence elasticity, tensile strength, adhesiveness, or retentiveness, or any combination thereof of a solid substrate of this invention. In one embodiment, the polymer application increases the elasticity of a solid substrate of this invention. In one embodiment, a polymeric application increases the tensile strength of a solid substrate of this invention. In one embodiment, the adhesiveness of a polymeric application relates to adhesion of mesenchymal stem cells, blood vessels, tissue at a site of desired repair, including cartilage repair, cartilage tissue, or bone tissue, or a combination thereof. In one embodiment, a polymeric application decreases the adhesiveness of a solid substrate of this invention. In one embodiment, a polymeric application increases the adhesiveness of a solid substrate of this invention. One skilled in the art will recognize that a polymeric application may increase adhesiveness for an item while decreasing adhesiveness for another item. For example, in one embodiment, the polymeric application increases adhesiveness for a mesenchymal stem cell and decreases adhesiveness of an infective agent. In one embodiment, the retentiveness of a polymeric application relates to retention of a cell population. In one embodiment, the cell population retained within a polymer coating is a mesenchymal stem cell population, chondrocyte population osteoblast population, etc. In one embodiment, the retentiveness of a polymeric application relates to retention of effector compounds.

In one embodiment, the thickness of the polymeric application influences proliferation and/or differentiation of cells applied to the solid substrates of this invention, or influences the activation or migration of cells associated with cell or tissue growth/restored function to the substrates of this invention, or a combination thereof.

Incorporation of a biocompatible polymer such as hyaluronic acid within a solid substrate of this invention, may be accomplished via any means, including, in some embodiments, pressure-driven application, for example, via application under vacuum, centrifugal force or mechanical pressure. In some embodiments, gravitational force is sufficient to allow appropriate and relatively homogenous penetration of the hyaluronic acid to a desired depth of the implant. According to this aspect, in one embodiment, visual inspection of the implant, for example using the staining with Fast Green/Safranin O, demonstrates uniform distribution of the hyaluronic acid through the substrate to a desired depth as a function of the time and conditions of application.

In one embodiment, the solid substrates of this invention may further comprise an effector compound, which in some embodiments, may be associated directly with the solid substrates of this invention, or in some embodiments, may be associated with a polymer, and applied in connection therewith.

In one embodiment, such effector compounds might include silver ions, copper ions or other metals, or combinations thereof. In another embodiment release of this compound might be facilitated by the application of electrical charge.

In another embodiment a first implant may be coated with a metal such as silver and a second implant may be coated with a second metal such as gold. Application of electrical field or actuation by battery might cause an electrical charge to flow between the implanted materials and lead to sterilization of the area due to discharge of silver ions. Such implementation might, for example, be useful in the treatment of osteomyelitis.

In one embodiment, the effector compound comprises a component of a kit of this invention for use for incorporation into a solid substrate of this invention as herein described.

In one embodiment of this invention, the effector compound comprises a cytokine, a bone morphogenetic protein (BMP), growth factors, a chelator, a cell population, a therapeutic compound, or an antibiotic, or any combination thereof. In one embodiment, the solid substrate further comprises a cytokine, a growth factor, a therapeutic compound, a drug, or any combination thereof.

In one embodiment of this invention, the phrase "a therapeutic compound" refers to a peptide, a protein or a nucleic acid, or a combination thereof. In another embodiment, the therapeutic compound is an antibacterial, antiviral, antifungal or antiparasitic compound. In another embodiment, the therapeutic compound has cytotoxic or anti-cancer activity. In another embodiment, the therapeutic compound is an enzyme, a receptor, a channel protein, a hormone, a cytokine or a growth factor. In another embodiment, the therapeutic compound is immunostimulatory. In another embodiment, the therapeutic compound inhibits inflammatory or immune responses. In one embodiment, the therapeutic compound comprises a pro-angiogenic factor.

In one embodiment, the effector compound comprises, an anti-helminth, an antihistamine, an immunomodulatory, an anticoagulant, a surfactant, an antibody, a beta-adrenergic receptor inhibitor, a calcium channel blocker, an ace inhibitor, a growth factor, a hormone, a DNA, an siRNA, or a vector or any combination thereof.

In one embodiment, the phrase "effector compound" refers to any agent or compound, which has a specific purpose or application which is useful in the treatment, prevention, inhibition, suppression, delay or reduction of incidence of infection, a disease, a disorder, or a condition, when applied to the solid substrates, kits and/or methods of this invention. An effector compound of this invention, in one embodiment, will produce a desired effect which is exclusive to the ability to image the compound. In some embodiments, the effector compound may be useful in imaging a site at which the compound is present, however, such ability is secondary to the purpose or choice of use of the compound.

In one embodiment of this invention, term "effector compound" is to be understood to include the terms "drug" and "agent", as well, when referred to herein, and represents a molecule whose incorporation within the solid substrate and/or kits of this invention, or whose use thereof, is desired. In one embodiment, the agent is incorporated directly within a solid substrate, and/or kit of this invention. In another embodiment, the agent is incorporated within a solid substrate and/or kit of this invention, either by physical interaction with a polymer coating, a coral, or coral particles of this invention, and/or a kit of this invention, or association thereto.

In one embodiment, the "effector compound" is a therapeutic compound.

In one embodiment, the phrase "a therapeutic compound", refers to a molecule, which when provided to a subject in need, provides a beneficial effect. In some cases, the molecule is therapeutic in that it functions to replace an absence or diminished presence of such a molecule in a subject. In one embodiment, the molecule is a nucleic acid coding for the expression of a protein is absent, such as in cases of an endogenous null mutant being compensated for by expression of the foreign protein. In other embodiments, the endogenous protein is mutated, and produces a non-functional protein, compensated for by the expression of a heterologous functional protein. In other embodiments, expression of a heterologous protein is additive to low endogenous levels, resulting in cumulative enhanced expression of a given protein. In other embodiments, the molecule stimulates a signaling cascade that provides for expression, or secretion, or others of a critical element for cellular or host functioning.

In another embodiment, the therapeutic compound may be natural or non-natural insulins, amylases, proteases, lipases, kinases, phosphatases, glycosyl transferases, trypsinogen, chymotrypsinogen, carboxypeptidases, hormones, ribonucleases, deoxyribonucleases, triacylglycerol lipase, phospholipase A2, elastases, amylases, blood clotting factors, UDP glucuronyl transferases, ornithine transcarbamoylases, cytochrome p450 enzymes, adenosine deaminases, serum thymic factors, thymic humoral factors, thymopoietins, growth hormones, somatomedins, costimulatory factors, antibodies, colony stimulating factors, erythropoietin, epidermal growth factors, hepatic erythropoietic factors (hepatopoietin), liver-cell growth factors, interleukins, interferons, negative growth factors, fibroblast growth factors, transforming growth factors of the α family, transforming growth factors of the β family, gastrins, secretins, cholecystokinins, somatostatins, serotonins, substance P, transcription factors or combinations thereof.

In any of the embodiments herein, solid substrates, and their use in the methods of the present invention may further comprise, or be implanted with, other compounds such as, for example, antioxidants, growth factors, cytokines, antibiotics, anti-inflammatories, immunosuppressors, preservative, pain medication, other therapeutics, and excipient agents. In one embodiment, examples of growth factors that may be administered in addition to the HMG-CoA reductase inhibitor include, but are not limited to, epidermal growth factor (EGF), transforming growth factor-alpha (TGF-α), transforming growth factor-beta (TGF-β), human endothelial cell growth factor (ECGF), granulocyte macrophage colony stimulating factor (GM-CSF), bone morphogenetic protein (BMP), nerve growth factor (NGF), vascular endothelial growth factor (VEGF), fibroblast growth factor (FGF), insulin-like growth factor (IGF), cartilage derived morphogenetic protein (CDMP), platelet derived growth factor (PDGF), or any combinations thereof. Examples of antibiotics include antimicrobials and antibacterials.

In any of the embodiments herein, solid substrates, and their use in the methods of the present invention may further comprise, or be implanted with, plasma, platelet rich plasma, any growth factor as appropriate, any glycosaminoglycan, in particular, hyaluronic acid and any useful form of same, or any combination of same. In some embodiments, the glycosaminoglycan is hyaluronic acid, sodium hyaluronate, cross linked hyalronic acid, or a combination thereof.

In one embodiment, effector compounds for use in a solid substrate and/or a kit of this invention and/or a method of this invention may comprise, inter-alia, an antibody or antibody fragment, a peptide, an oligonucleotide, a ligand for a biological target, an immunoconjugate, a chemomimetic functional group, a glycolipid, a labelling agent, an enzyme, a metal ion chelate, an enzyme cofactor, a cytotoxic compound, a bactericidal compound, a bacteriostatic compound, a fungicidal compound, a fungistatic compound, a chemotherapeutic, a growth factor, a hormone, a cytokine, a toxin, a prodrug, an antimetabolite, a microtubule inhibitor, a radioactive material, or a targeting moiety, or any combination thereof.

In one embodiment, the solid substrates and/or kits of this invention and/or methods of this invention comprise or make use of an oligonucleotide, a nucleic acid, or a vector. In some embodiments, the term "oligonucleotide" is interchangeable with the term "nucleic acid", and may refer to a molecule, which may include, but is not limited to, prokaryotic sequences, eukaryotic mRNA, cDNA from eukaryotic mRNA, genomic DNA sequences from eukaryotic (e.g., mammalian) DNA, and even synthetic DNA sequences. The term also refers to sequences that include any of the known base analogs of DNA and RNA.

The solid substrates and/or kits of this invention and/or methods of use of this invention may comprise nucleic acids, in one embodiment, or in another embodiment, the solid substrates and/or kits of this invention and/or methods of use of this invention may include delivery of the same, as a part of a particular vector. In one embodiment, polynucleotide segments encoding sequences of interest can be ligated into commercially available expression vector systems suitable for transducing/transforming mammalian cells and for directing the expression of recombinant products within the transduced cells. It will be appreciated that such commercially available vector systems can easily be modified via commonly used recombinant techniques in order to replace, duplicate or mutate existing promoter or enhancer sequences and/or introduce any additional polynucleotide sequences such as for example, sequences encoding additional selection markers or sequences encoding reporter polypeptides.

In one embodiment, effector compounds for use in a solid substrate and/or a kit of this invention and/or a method of this invention may comprise, inter-alia, a cytokine, a bone morphogenetic protein (BMP), growth factor, a chelator, a cell population, a therapeutic compound, an antiinflammatory compound, a pro-angiogenic compound or an antibiotic, or any combination thereof. In one embodiment, therapeutic compound or drug can include an antiinflammatory compound, an anti-infective compound, a pro-angiogenic factor or a combination thereof.

It will be appreciated that the solid substrates as herein described, and including any embodied addition to/incorporation within same, refers to such substrates possessing tapered sides as herein described, or in some embodiments, specifically shaped to be substantially ovoid in shape and optionally further comprising a taper, as described herein.

In some embodiments, the solid substrates of this invention may be seeded with cells, cell populations or tissue.

In some embodiments, the cells or tissue comprise stem or progenitor cells, or a combination thereof.

It will be appreciated that any appropriate stem or progenitor cell, from any source or obtained via any protocol is envisioned.

In some embodiments, adipose tissue derived stem cells are specifically envisioned for use in the methods of this invention and for incorporation with the solid substrates of this invention or kits of this invention.

In one embodiment of this invention, the cells or tissue as used in accordance with the substrates, methods of use or kits of this invention, are engineered to express a desired product.

In one embodiment, the phrase "a cell population" refers to a transfected cell population, a transduced cell population, a transformed cell population, or a cell population isolated from a subject, or a combination thereof. In some embodiments, transfected, transduced or transformed cells, may be seeded on the solid substrate, or in some embodiments, may be incorporated into a polymeric application thereto, or a combination thereof.

In one embodiment, a cell population of this invention comprises mesenchymal stem cells. In one embodiment, the mesenchymal stem cells are transformed.

In one embodiment, a cell population comprises cells beneficial in repair of a tissue for which the implantation of a solid substrate of this invention is desired.

In some embodiments, the cells are beneficial in and/or promote cartilage and/or bone formation and/or repair. Such cells may include chondroblasts or chondrocytes; fibrochondrocyte; osteocyte; osteoblast; osteoclast; synoviocyte; bone marrow cell; stromal cell; stem cell; embryonic stem cell; precursor cell, derived from adipose tissue; peripheral blood progenitor cell; stem cell isolated from adult tissue; genetically transformed cell; or a combination thereof. In another embodiment, a precursor cell may refer to a combination of chondrocytes and other cells; a combination of osteocytes and other cells; a combination of synoviocytes and other cells; a combination of bone marrow cells and other cells; a combination of mesenchymal cells and other cells; a combination of stromal cells and other cells; a combination of stem cells and other cells; a combination of embryonic stem cells and other cells; a combination of precursor cells isolated from adult tissue and other cells; a combination of peripheral blood progenitor cells and other cells; a combination of stem cells isolated from adult tissue and other cells; and a combination of genetically transformed cells and other cells. The precursor cells for use in the method of the present invention are prepared from an organ tissue of the recipient mammal (i.e. autologous), or a syngeneic mammal. In another embodiment, allogeneic and xenogeneic precursor cells may be utilized.

In one embodiment, the solid substrate of this invention incorporates stem or progenitor or precursor cells. Such cells can be obtained directly from a mammalian donor, e.g., a patient's own cells, from a culture of cells from a donor, or from established cell culture lines. In some embodiments, the mammal is a mouse, rat, rabbit, guinea pig, hamster, cow, pig, horse, goat, sheep, dog, cat, monkey, ape or a human. Cells of the same species and/or of the same immunological profile can be obtained by biopsy, either from the patient or a close relative. Using standard cell culture techniques and conditions, the cells are then grown in culture until confluent and used when needed. The cells may be cultured until a sufficient number of cells have been obtained for a particular application.

In one embodiment, the solid substrate of this invention incorporates any cell which may participate in tissue repair, for example, in cartilage and/or bone formation or repair. In some embodiments, such cells represent autografts, in that cells are cultured ex-vivo to seed the cells on the solid substrates of the invention, and such seeded solid substrates are implanted into the subject.

In some embodiments, such cells may represent allografts or xenografts, which may be incorporated within the solid substrates of this invention and implanted within a site of repair.

In one embodiment, a coral of this invention comprises a cell population from in vitro culture of the coral for a time period sufficient to seed the cells in the coral. In one embodiment, the cell population is a mesenchymal stem cell population, chondrocyte; fibrochondrocyte; osteocyte; osteoblast; osteoclast; synoviocyte; bone marrow cell; stromal cell; stem cell; embryonic stem cell; precursor cell, derived from adipose tissue; peripheral blood progenitor cell; stem cell isolated from adult tissue; genetically transformed cell; or a combination thereof. In one embodiment, the mesenchymal stem cells; chondrocyte; fibrochondrocyte; osteocyte; osteoblast; osteoclast; synoviocyte; bone marrow cell; stromal cell; stem cell; embryonic stem cell; precursor cell, derived from adipose tissue; peripheral blood progenitor cell; stem cell isolated from adult tissue; genetically transformed cell; or a combination thereof seeded in vitro are transformed. In one embodiment, the cell population comprises a cell population beneficial for cartilage repair. In one embodiment, the culture comprises a chelator. In one embodiment of this invention, the chelator in a culture comprises a calcium chelator.

In some embodiments, the solid substrate further comprises a bone filler or bone substitute material. In some embodiments, the solid substrate can be used as a bone filler or bone substitute material. In some embodiments, the solid substrate may further serve as a bone substitute or bone void filler. In some embodiments, the solid substrate may further incorporate a bone-substitute or bone void filler. In some embodiments, such bone-containing material may comprise autologous or allogeneic bone. In some embodiments, the bone-containing material may comprise animal bone.

This invention provides the unexpected application of optimally selected solid substrates being useful in cell and tissue growth and/or restored function and exemplified herein is the particular application for cartilage and bone repair and enhancement of formation.

In particular, this invention provides the unexpected application that bone regeneration, repair and enhancement of formation is optimal when the solid substrate is characterized by a specific fluid uptake capacity value of at least 75%, which specific fluid uptake capacity value was determined by establishing a spontaneous fluid uptake value divided by a total fluid uptake value and such substrate is inserted within a site for bone repair or when the solid substrate is characterized by having a contact angle value of less than 60 degrees, when in contact with a fluid, and further characterized by a substantially conical shape, having a circular cross section at each end of said solid substrate and tapered sides, and such substrate is inserted within a site for bone repair.

In other aspects, this invention provides the unexpected application that bone regeneration, repair and enhancement of formation is optimal when the solid substrate is characterized by a specific fluid uptake capacity value of at least 75%, which specific fluid uptake capacity value was determined by establishing a spontaneous fluid uptake value divided by a total fluid uptake value and such substrate is inserted within a site for bone repair or when the solid substrate is characterized by having a contact angle value of less than 60 degrees, when in contact with a fluid, and further characterized by having a radius of curvature that substantially approximates a radius of curvature of a tissue surface/site to which such solid substrate is being applied.

In other embodiments, this invention provides the unexpected advantage in terms of greater chondrogenesis, when the solid substrate is characterized by a specific fluid uptake capacity value of at least 75%, which specific fluid uptake capacity value was determined by establishing a spontaneous fluid uptake value divided by a total fluid uptake value or characterized by having a contact angle value of less than 60 degrees, when in contact with a fluid and further characterized by a substantially conical shape, having a circular cross section at each end of said solid substrate and tapered sides, and such substrate was inserted within the cartilage defect site.

In other aspects, this invention provides the unexpected advantage in terms of greater chondrogenesis, when the solid substrate is characterized by a specific fluid uptake capacity value of at least 75%, which specific fluid uptake capacity value was determined by establishing a spontaneous fluid uptake value divided by a total fluid uptake value or characterized by having a contact angle value of less than 60 degrees, when in contact with a fluid and further characterized by having a radius of curvature that substantially approximates a radius of curvature of a tissue surface/site to which such solid substrate is being applied.

In some embodiments, solid substrates of this invention may be applied for use in a subject with a bone defect in need of repair, wherein access to the bone defect results in the creation of a defect in the overlying cartilage, and the solid substrates of this invention allow for ideal healing of affected bone or bone and cartilage tissues.

In other embodiments, such solid substrates may be administered to a subject with a cartilage defect in need of repair, wherein optimal insertion of the solid substrate for stimulation of cartilage repair necessitates anchoring of the scaffold in the underlying bone, for example, by creating a minimal void in the underlying bone for insertion of the solid substrates, and once inserted, the solid substrate facilitates repair of both the overlying cartilage and underlying bone.

In other embodiments, such solid substrate may be administered to a subject with an osteochondral defect, where both bone and cartilage tissue are in need of repair as part of the pathogenesis of the disorder. The solid substrates according to this aspect are, in some embodiments, particularly suited for such applications.

It will be appreciated by the skilled artisan, that the applications, in particular, as related to bone therapy may include use of a solid substrate that incorporates any additional element as described herein, including, for example, bone allograft, bone autograft, bone substitutes, known bone void fillers, therapeutic compounds, and the like.

In some embodiments, the solid substrates of this invention may be used in conjunction with other known and/or available materials for stimulating/enhancing cell and/or tissue growth and/or restored function, for example, by promoting bone and/or cartilage repair.

In some embodiments, the solid substrates of this invention may be utilized to affix additional solid substrates, for example for use in whole joint repair or ligament repair, or other connector tissue repair.

It is to be understood that any use of the solid substrates of this invention, alone or in conjunction with other appropriate materials, for the treatment, repair or stimulation of cell or tissue growth or restored function is to be considered as part of this invention It will be appreciated that the solid substrates of this invention may be of any suitable size to accommodate its application in accordance with the methods of this invention. For example, and in some embodiments, for applications of the solid substrates of this invention within long bones of a subject, the dimensions of the solid substrate will be scaled to approximate that of the site into which the scaffold will be implanted, and may be on an order of magnitude scaling from millimeters to centimeters, as needed.

This invention provides, in some embodiments, solid substrates for use in repairing cartilage and/or bone tissue defects associated with physical trauma, or cartilage and/or bone tissue defects associated with a disease or disorder in a subject.

In some aspects, it is particularly contemplated that the methods, solid substrates, kits and tools and systems of the invention are suitable for hip replacement, great toe fusion, arthrodesis, ankle replacement or fusion, total or partial knee replacement procedures, including any or all of same.

In some embodiments, multiple coralline solid substrates as herein described are inserted to maximally occupy a defect site, to accommodate proper insertion into the desired region within a desired implantation site.

In one embodiment, the phrase "cartilage repair" refers to restoring a cartilage defect to a more healthful state. In one embodiment, restoring cartilage results in regeneration of cartilage tissue. In one embodiment, restoring cartilage results in regeneration of a full or partial thickness articular cartilage defect. In one embodiment, restoring cartilage results in complete or partial regeneration of cartilage tissue at a site of cartilage repair. In one embodiment, cartilage repair may result in restoration/repair of missing or defective bone tissue, wherein repair of a cartilage defect necessitates removal of bone tissue at a site of cartilage repair. In one embodiment, restoring cartilage results in regeneration of osteochondral defect. In one embodiment, cartilage repair comprises restoring cartilage defects of joints (e.g. knee, elbow, ankle, toe, finger, hip, shoulder joints), of ears, of a nose, or of a wind pipe.

In one embodiment, the phrase "bone repair" refers to restoring a bone defect to a more healthful state. In one embodiment, restoring bone results in regeneration of bone tissue. In one embodiment, restoring bone results in the filling in of any fracture or void within a bone tissue. In one embodiment, restoring bone results in complete or partial regeneration of bone tissue at a site of bone repair. In one embodiment, bone repair may result in restoration/repair of missing or defective bone tissue. In one embodiment, bone repair comprises restoring bone defects of any bone, treating bone edema, and other bone disorders, as needed.

In some embodiments, the phrase "bone repair" refers to the treatment of a subject with osteoporosis, Paget's disease, fibrous dysplasias, bone edema or osteodystrophies. In another embodiment, the subject has bone and/or cartilage infirmity. In another embodiment, the subject has other bone remodeling disorders include osteomalacia, rickets, rheumatoid arthritis, achondroplasia, osteochodrytis, hyperparathyroidism, osteogenesis imperfecta, congenital hypophosphatasia, fribromatous lesions, multiple myeloma, abnormal bone turnover, osteolytic bone disease, periodontal disease, or a combination thereof. In one embodiment, bone remodeling disorders include metabolic bone diseases which are characterized by disturbances in the organic matrix, bone mineralization, bone remodeling, endocrine, nutritional and other factors which regulate skeletal and mineral homeostasis, or a combination thereof. Such disorders may be hereditary or acquired and in one embodiment, are systemic and affect the entire skeletal system.

In other aspects, the invention specifically contemplates use of the solid substrates as herein described and methods for use of same for treating a bone and/or cartilage defect arising as a consequence of tumor or avascular necrosis.

The solid substrates, kits and methods of the invention may also be used to enhance bone and/or cartilage formation in conditions where a bone and/or cartilage deficit is caused by factors other than bone remodeling disorders. Such bone deficits include fractures, bone trauma, conditions associated with post-traumatic bone surgery, post-prosthetic joint surgery, post plastic bone surgery, bone chemotherapy, post dental surgery and bone radiotherapy. Fractures include all types of microscopic and macroscopic fractures. In one embodiment, some examples of fractures includes avulsion fracture, comminuted fracture, transverse fracture, oblique fracture, spiral fracture, segmental fracture, displaced fracture, impacted fracture, greenstick fracture, torus fracture, fatigue fracture, intraarticular fracture (epiphyseal fracture), closed fracture (simple fracture), open fracture (compound fracture) and occult fracture. In one embodiment, fractures meant to be treated using the methods of the present invention are non-union fractures.

In one embodiment, methods, materials and kits of this invention are utilized for induced or enhanced repair of a cartilage and/or bone defect or disorder or disease. In one embodiment, the cartilage defect results from a trauma, a tear, a sports injury, a full thickness articular cartilage defect, a joint defect, or a repetitive stresses injury (e.g., osteochondral fracture, secondary damage due to cruciate ligament injury). In one embodiment, the cartilage disorder comprises a disease of the cartilage. In one embodiment, methods of this invention induce or enhance cartilage repair in osteoarthritis, rheumatoid arthritis, aseptic necrosis, osteoarthritis, including osteochondritis dissecans, articular cartilage injuries, chondromalacia patella, chondrosarcoma, chondrosarcoma—head and neck, costochondritis, enchondroma, hallux rigidus, hip labral tear, osteochondritis dissecans, torn meniscus, relapsing polychondritis, canine arthritis, fourth branchial arch defect or cauliflower ear. In one embodiment, methods of this invention induce or enhance cartilage repair in degenerative cartilagenous disorders comprising disorders characterized, at least in part, by degeneration or metabolic derangement of connective tissues of the body, including not only the joints or related structures, including muscles, bursae (synovial membrane), tendons, and fibrous tissue, but also the growth plate, meniscal system, and intervertebral discs.

In one embodiment, methods, materials and kits of this invention are utilized for resurfacing joints and in some embodiments, the methods, materials and kits of this invention in use as described herein, prevent, reduce the need, delay the need or abrogate the need for joint replacement. In one embodiment, the method reduces the incidence or extends the time or need for joint replacement in an affected subject.

In one embodiment, the solid substrates, kits and methods of the invention may also be used to augment long bone fracture repair; generate bone in segmental defects; provide a bone graft substitute for fractures; facilitate tumor reconstruction or spine fusion; provide a local treatment (by injection) for weak or osteoporotic bone, such as in osteoporosis of the hip, vertebrae, or wrist, or a combination thereof. In another embodiment, the solid substrates, kits and methods of the invention may also be used in a method to accelerate the repair of fractured long bones; treat of delayed union or non-unions of long bone fractures or pseudoarthrosis of spine fusions; induce new bone formation in avascular necrosis of the hip or knee, or a combination thereof.

In some embodiments, the solid substrates, kits and methods of the invention may also be used as an alternative to joint replacement, for any bone as herein described, e.g. hip, knee, shoulder, elbow, ankle, and others as will be appreciated by the skilled artisan.

In one embodiment, methods of this invention are evaluated by examining the site of cartilage and/or bone tissue repair, wherein assessment is by histology, histochemistry, palpation, biopsy, endoscopy, arthroscopy, or imaging techniques comprising X-ray photographs, computerized X-ray densitometry, computerized fluorescence densitometry, CT, MRI or another method known in the art, or any combination thereof.

In one embodiment, a method of this invention comprises inducing and enhancing cartilage and/or bone repair wherein implanting a solid substrate of this invention within a site of cartilage and/or bone repair influences and improves cartilage and/or bone repair and optionally using the specialized tools of this invention.

In one embodiment, a method of this invention induces or enhances cartilage and/or bone repair, wherein the solid substrate attracts a population of cells to the solid substrate, thereby influencing or improving cartilage and/or bone repair.

A clinician skilled in the art will recognize that methods of this invention, which entail implanting a coralline solid substrate within a site of cartilage and/or bone repair, may require preparation of a site of cartilage and/or bone repair. These preparations may occur prior to implantation of a coralline solid substrate or simultaneously with implantation. For example, cartilage and/or bone tissue and/or other tissues proximal to a site of cartilage and/or bone repair may initially be drilled through to create a channel of dimensions appropriate for a coralline solid substrate used in the methods of this invention. Then the coralline solid substrate is implanted within the site so that a region of the coralline solid substrate penetrates the drilled cartilage and/or bone tissues. Alternatively, the coralline solid substrate may be attached to a tool capable of penetrating through cartilage and/or bone or other tissues, or a combination thereof. In this case, as the tool penetrates through the cartilage and/or bone tissue, the attached coralline solid substrate is simultaneously implanted.

In some embodiments, following implantation of the solid substrate within a repair site, or several solid substrates within the repair site, the solid substrate is processed to optimize incorporation and optimal cartilage and/or bone repair. In some embodiments, such processing may comprise cutting, sanding or otherwise smoothing the surface of the solid substrate or coralline solid substrates, for optimal repair.

It will be apparent to those skilled in the art that various modifications and variations can be made in the solid substrates, kits, process and methods of the present invention without departing from the spirit or scope of the invention.

In some aspects, the invention provides tools and kits comprising same for use in implanting a solid substrate as herein described.

In some aspects, the invention may provide a tissue shaper and alignment tool for implantation of an optimized solid substrate in a subject, said tissue shaper and alignment tool comprising:

an elongated body having a central hollow spanning the length of said body;
a shaping structure terminally joined to said elongated body by a joint region having a central hollow and further comprising:
  a first shaping region located proximal to said joint region, which first shaping region is substantially smooth and has parallel-oriented sides or sides tapered at an angle from a longitudinal axis of said tool; and
  a second shaping region located distal to said joint region, which second shaping region comprises a series of laterally extending protrusions, and has tapered sides at an angle from a longitudinal axis of said tool; and
optionally a gripping handle, terminally joined to said elongated body by a joint region located distal to said shaping structure;
wherein said shaping structure is sized to be of a dimension to facilitate a snug fit within the borders of a site of implantation.

In some embodiments, the taper in the second shaping region and optionally in the first shaping region, in terms of the angle associated thereto will reflect the corresponding taper angle in the solid substrate being selected for implantation.

In some aspects, the specific choice and match of taper between tool and solid substrate further facilitates the press fit insertion of the solid substrate within the desired implant site.

Example 3 provides a description of the tissue shaper and alignment tool and other tools for use in implantation of a solid substrate as herein described.

In some aspects, the lateral protrusions of the tissue shaper and alignment tool as herein described function as a series of dull blades, which when placed within and rotated within an implantation site, create a site with smooth walls, which have tapered sides at an angle of two degrees from a longitudinal axis in said implantation site.

In some embodiments, use of such tissue cutter, reamer, shaper tools may be manually operated or motor driven.

In some embodiments, use of such tissue cutter, reamer, shaper tools may be manually operated, which, in turn may follow use of similar tools which are motor driven, and the manual introduction of same may, in some aspects, provide for the removal of a layer of tissue that has been adversely effected by the use of the motor driven tool. For example, use of such motor driven tools may result in inadvertent heating, cell death or other necrosis stimulators in the tissue in a desired site of implantation and subsequent manual tissue cutter, reamer, shaper tool use may facilitate removal of damaged tissue to promote implant interaction with underlying non-necrotic tissue.

In some aspects, such lateral protrusions may be of similar size and shape, or in some embodiment, may be of staggered height, or in some embodiments, may have varying angles of incline, or in some embodiments, may be of staggered widths, or in some embodiments, a combination thereof.

In some embodiments, the tool comprises at least one lateral protrusion. In some embodiments, the tool comprises more than one lateral protrusion.

In some embodiments, the tool comprises at least six lateral protrusions, or in some embodiments, the tool comprises at least eight lateral protrusions, or in some embodiments, the tool comprises at least ten lateral protrusions, or in some embodiments, the tool comprises at least twelve lateral protrusions, or in some embodiments, the tool comprises at least four lateral protrusions, or in some embodiments, the tool comprises from two to six lateral protrusions.

In some embodiments, the lateral protrusions have a long axis parallel to the longitudinal axis of the tool and in some embodiments, the lateral protrusions are angled with respect to the longitudinal axis of the tool. In some embodiments, the lateral protrusions are angled with respect to the longitudinal axis of the tool, at an angle from 1 to 15 degrees. In some embodiments, the lateral protrusions are angled with respect to the longitudinal axis of the tool, at an angle from 0.5 to 5 degrees. In some embodiments, the lateral protrusions are angled with respect to the longitudinal axis of the tool, at an angle from 0.75 to 4 degrees, or in some embodiments, the lateral protrusions are angled with respect to the longitudinal axis of the tool, at an angle from 1 to 3.5 degrees, or in some embodiments, the lateral protrusions are angled with respect to the longitudinal axis of the tool, at an angle from 1.5 to 3.25 degrees, or in some embodiments, the lateral protrusions are angled with respect to the longitudinal axis of the tool, at an angle from 1.75 to 3 degrees, or in some embodiments, the lateral protrusions are angled with respect to the longitudinal axis of the tool, at an angle from 1.75 to 2.5 degrees. It will be appreciated that in some aspects, a press fit is desired and the lateral protrusions of the tissue shaper and alignment tool of this invention will have be angled, with respect to the longitudinal axis of the tool to approximate the angle of taper of the solid implants of this invention.

In some embodiments, the invention provides kits comprising such shaping tools as herein described.

In some embodiments, the invention provides a method for implantation of an optimized solid substrate for promoting cell or tissue growth or restored function in a subject in need thereof, said method comprising:

Isolating or preparing an optimized solid substrate for promoting cell or tissue growth or restored function, which solid substrate comprises a coral or coral derivative, is characterized by a specific fluid uptake capacity value of at least 75%, or is characterized by having a contact angle value of less than 60 degrees and which is further characterized by a substantially conical shape, having a circular cross section at each end of said solid substrate and tapered sides;

establishing a specific fluid uptake capacity value of said solid substrate, which specific fluid uptake capacity value is determined by establishing a spontaneous fluid uptake value divided by a total fluid uptake value;

selecting a solid substrate characterized by a specific fluid uptake capacity value of at least 75% or is characterized by having a contact angle value of less than 60 degrees; and implanting said solid substrate characterized by a specific fluid uptake capacity value of at least 75% or is characterized by having a contact angle value of less than 60 degrees within a desired site in a subject, wherein said implanting is conducted at an implant angle of 2 degrees from an axis perpendicular to the surface of the tissue site being thus treated.

In some aspects, the method further comprises the step of:
inserting a rod-like structure within a target tissue implantation site in a subject, optionally with the aid of an implement orienting said rod-like structure to be in an orientation perpendicular to a plane of a surface of said target graft withdrawal or implantation site and in an orientation to be centralized within said implantation site;

drilling an area of tissue in said subject which is less than that of a desired tissue implantation site in an orientation perpendicular to a surface of said area of tissue, optionally with a drill bit adapted for application over said rod-like structure;

surgically excising tissue from an area of desired implantation, by optionally applying a surgical cutter over said rod-like structure;

shaping said area of desired implantation with the aid of a tissue shaper and alignment tool comprising:
  an elongated body having a central hollow spanning the length of said body;
  a shaping structure terminally joined to said elongated body by a joint region having a central hollow and further comprising:
    a first shaping region located proximal to said joint region, which first shaping region is substantially smooth and has parallel-oriented sides or sides tapered tapered sides at an angle of two degrees from a longitudinal axis of said tool; and
    a second shaping region located distal to said joint region, which second shaping region comprises a series of laterally extending protrusions, and has tapered sides at an angle of two degrees from a longitudinal axis of said tool; and
  optionally a gripping handle, terminally joined to said elongated body by a joint region located distal to said shaping structure;

wherein said shaping structure is sized to be of a dimension to facilitate a snug fit within the borders of a site of implantation.

and applying a tissue graft or solid implant within said area of tissue, optionally by inserting a cannulated implant within said area of desired implantation, over said rod-like structure;

wherein said shaping promotes creation of a site with tapered sides at an angle of two degrees from a longitudinal axis through the site of implantation promoting ideal incorporation of said solid implant.

In some aspects, this invention provides a curved alignment and positioning tissue extraction base, comprising:
  a basal surface having a radius of curvature complementary to a radius of curvature of a tissue to which said curved alignment and positioning tissue extraction base is being affixed;
  an outer boundary substantially ovoid in shape further comprising at least two externally located lateral extensions through which respective rod-like structures can be inserted; and
  at least two internally located hollowed regions spanning the length of said curved alignment and positioning tissue extraction base.

In some aspects, the curved alignment and positioning tissue extraction base is useful for preparing a site of implantation in a subject, where the implantation is within a site with a curvature.

In some aspects, the curved alignment and positioning tissue extraction base, comprises a basal surface having a radius of curvature complementary to a radius of curvature of a tissue to which the curved alignment and positioning tissue extraction base is being affixed.

In some aspects, such tissue to which the curved alignment and positioning tissue extraction base is being affixed may comprise a condyle, a capitulum of the humerus, a humeral trochlea, a femoral head or any curved portion of a bone, cartilage or combination thereof.

In some aspects, the curved alignment and positioning tissue extraction base will have a radius of curvature essentially comparable to the radius of curvature of the tissue site to which such base is being applied.

Figure 11A:
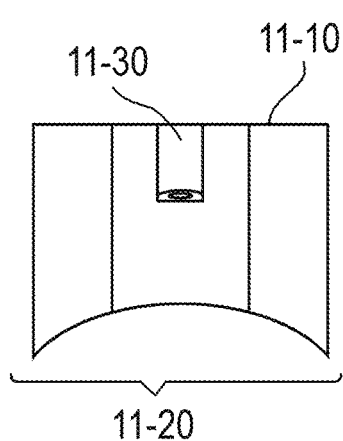
FIGS. 11A-11H schematically depict embodied curved alignment and positioning tissue extraction bases or jig bases of this invention. Side views are shown in FIGS. 11A, 11E and 11G, highlighting the basal surface having a radius of curvature complementary to a radius of curvature of a tissue to which said curved alignment and positioning tissue extraction base is being affixed (11-20), and locking mechanism insertion structure (11-30), which are lateral modifications of the jig base through which an immobilizing structure can be inserted, for example, a tissue screw or K-wire.
Figure 11B:
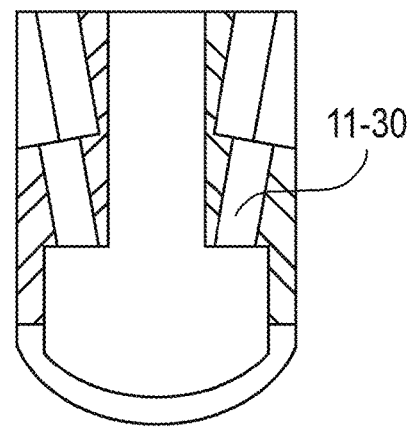
Figure 11C:
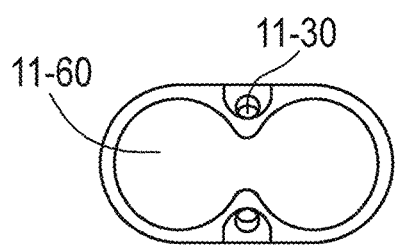
Figure 11D:
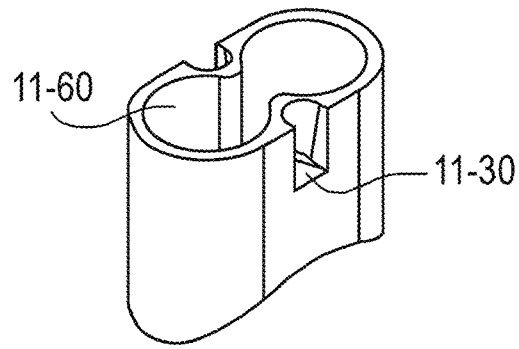
Figure 11E:
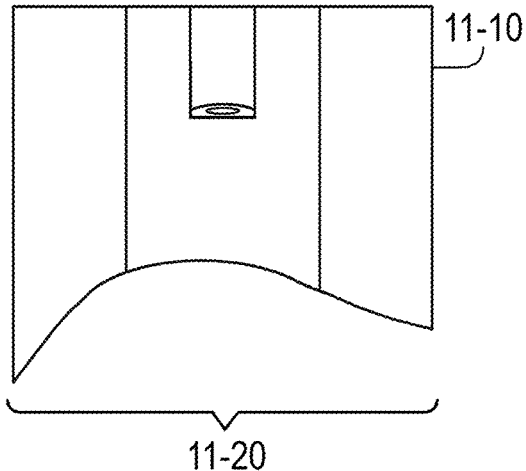
Figure 11F:
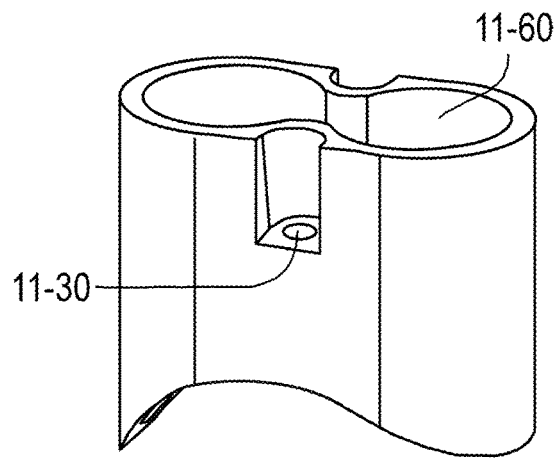
Figure 11G:
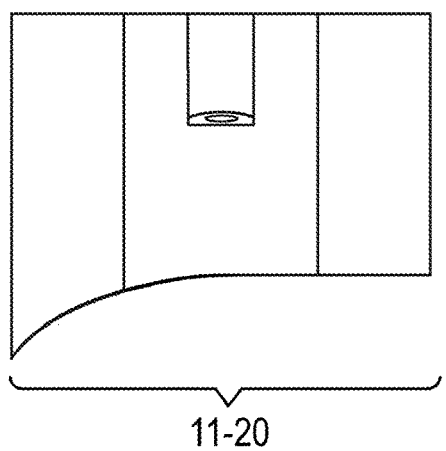
Figure 11H:
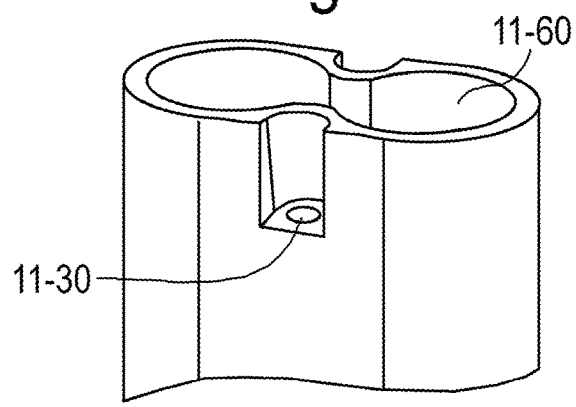

Referring to FIG. 11, and in particular, to FIGS. 11A, 11E and 11G, as exemplified in these figures, the jig base, in some aspects, will have a radius of curvature that is symmetric and in some embodiments, the radius of curvature will be asymmetric. In some aspects, the lack of symmetry may be along an X-axis, or in some embodiments, along a Z-axis, or in some embodiments, along both an X- and Z-axis in three dimensional space.

In some aspects, the radius of curvature may be in any appropriate configuration, and this may be with respect to the curved portions of any of the tools as herein defined, for example, but not limited to the jig base, implant or tampers as herein described.

In some aspects, the radius of curvature will most nearly approximate the curvature of the surface of the tissue to which the respective tool is being applied. In some aspects, this will reflect a varying radius of curvature in an X-axis of the respective tool surface with a constant radius of curvature along a Z-axis, or in some embodiments, this will reflect a varying radius of curvature in a Z-axis of the respective tool surface with a constant radius of curvature along an X-axis, or in some embodiments, this will reflect a varying radius of curvature in an X-axis of the respective tool surface along with a varying radius of curvature along the Z-axis of the tool surface. In some aspects, the curved tools of this invention or curved parts of tools of this invention will be understood to comprise modifications to same to specifically best fit a defect site/tissue site to which the respective too is being applied.

In some aspects, the radius of curvature may effectively be of standard dimensions, depending upon the age, weight, genetic makeup, etc. of the subject, which in turn defines a set of tools that may be prepared for example, for inclusion in a kit, for use in accordance with the methods of this invention.

In some aspects, the radius of curvature is established empirically, via known methods in the art. In some aspects, the curved alignment and positioning tissue extraction base will have a radius of curvature that is essentially standardized, such that when the radius of curvature of the tissue site to which the base is applied is determined, an easy choice of appropriate base will be made and the corresponding appropriate base chosen for use.

The curved alignment and positioning tissue extraction base will further comprise, in some embodiments, an outer boundary substantially ovoid in shape.

In some aspects, the outer boundary is substantially rectangular, or assumes a shape that is substantially that of a rectangular prism.

In some aspects, the outer boundary is substantially cuboidal in shape.

In some aspects, the outer boundary is substantially oblong and assumes an approximate overall shape most appropriate for preparing a given tissue site for implantation.

In some aspect, the outer boundary of the curved alignment and positioning tissue extraction base of this invention further comprises at least two externally located lateral extensions positioned substantially midway between poles of the curved alignment and positioning tissue extraction base through which respective rod-like structures can be inserted.

In some aspects, the outer boundary of the curved alignment and positioning tissue extraction base of this invention further comprises at least two externally located lateral extensions, which lateral extensions are optionally positioned substantially midway between the poles, or optionally positioned substantially at the poles of the curved alignment and positioning tissue extraction base.

In some aspects, the at least two externally located lateral extensions are positioned somewhere between the poles of the base and midway between the poles of the base, as may be required to best position the curved alignment and positioning tissue extraction base of this invention.

FIGS. 11A, 11D and 11E depict an embodied curved alignment and positioning tissue extraction base of this invention. In this aspect, the basal surface having a radius of curvature is shown (11-20). FIG. 21A further depicts various embodied curved alignment and positioning tissue extraction base of this invention, at item 10. As is evident from this embodiment, a variety of curvature radii are envisioned and kits comprising various curved alignment and positioning tissue extraction bases to suit a variety of applications are envisioned, as well.

In some aspects, the curvature radii will be substantially symmetrical and in some embodiments, the curvature radii will by substantially asymmetrical. It will be appreciated that the choice in tool/implement for use in a particular application will best address an ideal fit, with respect to the surface characteristics being treated, and implants and tools for implantation of same will be chosen to best address same.

FIGS. 11D and 11E highlight the presence of externally located lateral extensions (11-30) through which respective rod-like structures can be inserted. Referring to FIG. 11I, insertion of such rod-like structures 11-100 through the lateral extensions 11-30 is seen. According to this aspect, the lateral extensions are positioned substantially midway between the poles of the device, however, the skilled artisan will appreciate that the lateral extensions can be positioned in any convenient region on the outer surface of the base, for example, at the polls, or between the polls and the midway point between the polls, and any such positioned is envisioned and to be considered as part of this invention.

In some aspects, with respect to the curved tools and solid substrates of this invention, it will be appreciated that such solid substrates and elements of tools as herein described as possessing a radius of curvature, which radius of curvature serves to specifically accommodate implantation of a solid substrate within an implant site in a subject having a radius of curvature in same, such radius will approximate that of the tissue site being treated, and in some embodiments, will possess a radius of curvature that is symmetric or in some embodiments, asymmetric along an X-axis of same, or in some embodiments, such radius will possess a radius of curvature that is symmetric or in some embodiments, asymmetric along a Z-axis of same, or in some embodiments, such radius will possess a radius of curvature that is symmetric or in some embodiments, asymmetric along an X- and a Z-axis of same.

In some aspects, the positioning of the jig base may be facilitated with the use of a specialized handle. FIG. 11I depicts an embodied handle 11-70, which is characterized by the presence of terminal modifications. In one aspect terminal part 11-90 inserts within a void or space 11-60 in the jig base, and may further contain a stopper 11-80, which ensures that the handle is only advanced to a desired depth within the jig base.

In some aspects, the jig base may be stably applied and immobilized within a desired tissue site.

In one aspect, a tissue screw or K-wire (see e.g. 11-100, 21-100, inserts through the jig base through lateral modifications 11-30 inserting within underlying tissue in the subject.

It will be appreciated that the immobilizing structure can be a simple pointed structure, such as a K-wire (for example, as depicted in FIG. 21B, 21C or 21D) 21-150, or in some aspects, the structure may have terminal modifications such as screw-like projections 21-260 or laterally extending protrusions, to better grip/attach to the underlying tissue into which it is inserted. In some embodiments, each end may be terminally modified with a different structure, for example, one end is a simple pointed structure, while the other terminus contains a terminal screw-like projection (See FIG. 21E).

Cleaning tools may also be included in the kits of this invention.

Figure 11L:
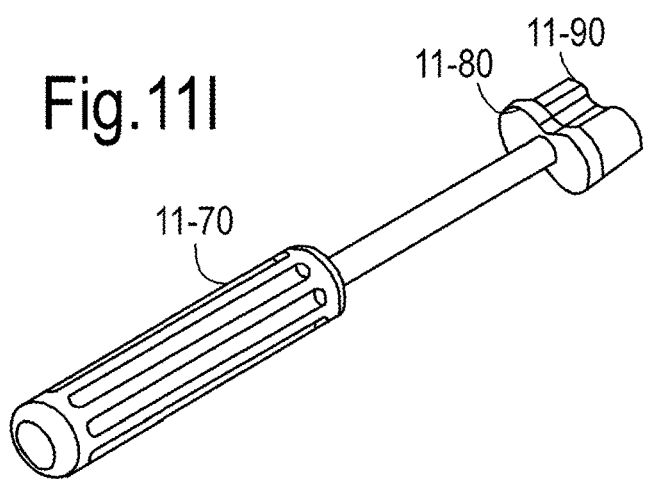
FIG. 11L depicts immobilization of the jig base via insertion of an immobilizing structure, such as a rod-like structure or K-wire, within the lateral modifications to affix the jig base to the underlying tissue below. Also depicted in FIG. 11I is a specialized bit 11-110.

In some aspects, a specialized bit 11-110 may be used to specifically affix the immobilizing structure within the underlying tissue. (FIG. 11L). In some aspects, the specialized bit fits standard drills and other tools for insertion within tissue.

In some aspects, the immobilizing structure lateral modification through which the immobilizing structure inserts is so oriented and constructed that the immobilizing structure/rod-like structure inserts within underlying tissue in a region that is interior to the outer defect margins. According to this embodiment, the immobilizing structure inserts within the underlying tissue in a region over which an implant is placed, and this region is not exposed following insertion of an implant within the defect site and therefore any holes or insert within the tissue is ultimately covered with an implant structure and optionally is remodeled as part of the healing process of the implant procedure.

In some aspects, insertion of the rod-like structure may be further reinforced or in some embodiments, immobilized by the use of "lockers". In some aspects, such lockers have a shaft and a head piece, which are so constructed so as to fit over the immobilizing structure/rod-like structure, and lock same into place. In some aspects, the shaft will further comprise a basal terminal modification, which locks into place in the jig base. Referring to FIG. 12C, the terminal modification/locking part 12-124 may be a simple extension of the shaft, which can readily insert within a cognate locking part in the jig base, e.g. by containing a slot mechanism into which the locking part 12-124 may insert. In other aspects, the shaft may contain an apical terminal modification, e.g. threading as depicted at 12-130 which fits within the head piece 12-126, which also contains a threaded part 12-128, which serves to bring the respective sides of the terminal region of the shaft into closer proximity, effectively narrowing the space surrounding the K-wire/rod-like structure, and thereby more specifically immobilizing same. In some aspects, the lockers may comprise both basal and apical locking mechanisms.

In some aspects and referring to FIGS. 12G-12K, the locker shaft may comprise terminal modifications to provide a more optimal fit with respect to the immobilizing structures inserted/locked thereby. In some aspects, the locker may comprise a terminal threaded region 12-130, with a fitted joint region 12-132, such that when the locker head piece 12-126 is fitted onto same, individual sections of the fitted joint region 12-132 may be brought closer together to effectively narrow the diameter of the hollow region 12-116 to more securely lock around the immobilizing structure fitted therethrough. The locker head piece 12-126 may also comprise a threaded region 12-128, which promotes the narrowing of the diameter of the hollow region as described. Referring to FIG. 12L, in some aspects, as the locker head piece 12-126 is screwed onto the threaded region 12-130 of the locker, e.g. for example turning along axis 12-127, the sides of the threaded region are brought closer, for example, at the arrows designated by 12-133, and this in turn more snugly catches the immobilizing structure located therewithin.

Once the jig base is stably attached or immobilized at the desired tissue site, a region into which a desired implant will be inserted is defined and is internal to the boundaries of the aligning stabilizer base.

In some aspects, the region of tissue into which a desired implant will be inserted contains a defect site in underlying bone, cartilage or both.

This invention also provides a perpendicular implantation aligner tool, which fits within the jig base as herein described.

In some aspects the "perpendicular implantation aligner" also referred to herein as a "perpendicular aligner" may be used to define an ideal orientation for preparing an implantation site in a tissue of a subject. According to this aspect, the perpendicular implantation aligner allows for a precise insertion of a rod like structure within a desired tissue site, where the inserted immobilizing structure/rod-like structure will be perpendicular in orientation to a long axis of the tissue surface being thus treated. Uniquely the orientation is attainable, even when the surface being treated is curved in nature.

FIG. 13 shows embodied aspects of a perpendicular implantation aligner, which comprises at least one elongated shaft.

The at least one elongated shaft will in turn comprise at least one central hollow spanning the length of the shaft. The perpendicular implantation aligner further comprises a terminal grip having at least one hollow region spanning the length of the grip and lining up with the hollow spanning the length of the shaft.

Referring to FIGS. 13C and 13D, for example, a central hollow 13-116 lines up when passing through the terminal grip part 13-142 and the elongated shaft, part 13-138.

The perpendicular implantation aligner further comprises an insertion base having at least one hollow region spanning the length of the base and lining up with the central hollow spanning the length of the shaft.

Referring to FIG. 13D, the insertion base 13-134 also possesses at least one hollow 13-116, which lines up with the hollow through the shaft region and through the terminal grip.

In some aspects, the insertion base will be substantially ovoid in shape and of a size capable of inserting within the jig base as herein described.

The central hollow spanning the perpendicular implantation aligner promotes insertion of an immobilizing structure/rod-like structure therewithin.

In some aspects, the perpendicular aligner has a base of dimensions and overall shape, which specifically inserts within a jig base, and optionally further comprises a stopper region, which prevents unchecked advance of the perpendicular aligner within the jig base.

In some aspects, one or more perpendicular implantation aligners may be utilized in an implant procedure. In some aspects, a first perpendicular implantation aligner is used to create two terminal substantially circular or oval drilled sites, in preparation of an implant insertion.

According to this aspect, and in some embodiments, such first perpendicular implantation aligner will therefore contain at least two central hollows spanning the grip, shaft and base of the first perpendicular implantation aligner.

In some aspects, if the defect site is large and therefore a larger implant site is required, then the first perpendicular implantation aligner may be used, for example, to create three or four substantially circular or oval drilled sites, positioned along a long axis of the intended implant site in preparation for the implant insertion.

It will be appreciated that the tools of this invention can be scaled to be of a larger and/or smaller size, as appropriate, and may contain multiples of certain key aspects to accommodate and be appropriate for implantation of a larger implant structure, as well as being suitable and scaled for smaller implant procedures, for example by incorporating singles of key structures as will be appropriate for same.

FIG. 13G embodies the perpendicular alignment of two rod-like structures within the jig base, perpendicular in orientation to a tissue site being treated in a subject.

In some aspects, the use of the perpendicular implantation aligner allows for specific drilling within a tissue site in a desired ideal orientation (i.e. perpendicular in orientation to a tissue site being thus treated). According to this aspect and in some embodiments, this invention provides a drill bit protective sheath, comprising:
 at least one elongated shaft comprising at least one central hollow spanning the length of said at least one elongated shaft and sized to fit insertion of a drill bit and rotation of said drill bit therewithin;
 a top portion having at least one central hollow spanning the length of said top portion and lining up with said at least one central hollow spanning the length of said at least one elongated shaft; and
 an insertion base having at least one central hollow region spanning the length of said insertion base and lining up with said at least one central hollow spanning the length of said at least one elongated shaft and further being of a size capable of inserting within the curved alignment and positioning tissue extraction base as herein defined.

According to this aspect and in some embodiments, the drill bit protective sheath will comprise at least one elongated hollowed shaft sized to fit insertion of a drill bit and rotation of the drill bit therewithin.

In some aspects, the drill bit protective sheath will further comprise a top portion, having at least one central hollow, lined up with the hollow in the elongated shaft. The top portion may also comprise an extension, which prevents unchecked advancement of a drill bit inserted within the drill bit protective sheath.

The drill bit protective sheath will still further comprise an insertion base comprising at least one central hollow, lining up with the corresponding hollow/s in the elongated shaft. The protective sheath therefore inserts within the jig base, over the K-wires/rod-like structures, so that drilling within the intended implantation site can be specifically controlled in terms of the orientation and shape and depth of same.

According to this aspect and in some embodiments, referring to FIG. 14, the drill bit protective sheath containing two barrels 14-138 are shown. The drill protective sheath contains hollows 14-152 spanning through each top portion 14-142, barrels 14-138 and base 14-134, so that the immobilizing structures may insert therethrough. The drill protective sheath top 14-142 may be so modified such that when a drill bit is inserted therethrough, over the immobilizing structure, the top of the drill bit protective sheath provides a stopper mechanism, as well, preventing unchecked advancement of the drill and drill bit within the drill protective sheath.

The drill protective sheaths of this invention are designed to promote insertion of a drill bit therethrough, which drill bits, in turn, may further comprise a central hollow that spans the drill bit, so that same can insert over the immobilizing structure. In some aspects, such a drill bit fitting over the immobilizing structure ensures drilling in a particular orientation, optimized for ideal preparation of the implant site.

In some aspects, the drill bit as well, will comprise a stopper preventing continued advancement of the drill bit within the protective sheath. In some aspects, the drill bit comprises a terminus particularly sized to be a standard fit for most drills in use.

Once drilling is complete, the drill bit is removed.

In some aspects the drilled sites may be further modified, for example, to incorporate a taper as described hereinabove, by incorporation of a tissue reamer/shaper as herein described. Referring to FIG. 15 and Example 4 hereinbelow, such tissue reamer will, as well, comprise a central hollow which in turn may insert over the K-wire/immobilizing structure to ensure that tissue shaping, as well, conforms in terms of the desired perpendicular orientation.

According to this aspect, as will be appreciated by the skilled artisan, given the drilling orientation of the drill bit within the sheath, circular/speherical voids are created in the underlying tissue, so that if the embodied sheath of FIG. 14 is used, two circular void regions have been drilled in the underlying tissue.

According to this aspect, it is desirable to provide a substantially ovoid implantation site and therefore upon removal of the drill bit protective sheath a second perpendicular implantation aligner may be used, which provides at least one central hollow positioned to be substantially midway between two drilled regions in an underlying tissue. Such second perpendicular implantation aligner will comprise the features of a first perpendicular aligner in terms of the presence of a terminal grip, hollow-containing shaft and base which inserts within a jig base. Such second perpendicular implantation aligner will further comprise at least one (or multiple) hollow regions, through which a K-wire may insert therethrough and which overall drilling and ultimate shaping is desired.

According to this aspect, once the K-wire/immobilizing structure is affixed thereto the jig base may be removed, and a drill bit protective sheath may be further utilized to create an additional drilled void (or voids) in the underlying tissue, for example, midway located between the prior introduced drilled voids.

When a substantially ovoid implantation site is desired, in some aspects, this invention further provides a contour cutter, comprising:
 a central hollow, spanning a length of said contour cutter, through which a rod-like structure may insert;
 an outer boundary substantially ovoid in shape; and
 at least one blade structure, which is slidingly attached to said outer boundary such that it may be raised and lowered within said contour cutter; and
 optionally at least one hollowed housing for insertion of a second rod-like structure therethrough.

As will be appreciated by the skilled artisan, the contour cutter serves to create a desired contour for the boundaries of the implant site. In order to ensure ideal/optimal orientation of the contour cutter, the contour cutter will also comprise a central hollow through which the rod-like structure may insert, which in turn ensures ideal/optimal orientation of the cutter, i.e. perpendicular in orientation to the implant surface. The contour cutter may be further secured via the use of additional immobilizing structures inserted therethrough, for example, through the optional additional hollowed housings in the cutter as noted herein.

The contour cutter further may comprise an overall shape that is substantially similar to that of the jig base, or substantially similar to the desired contour of the implant site.

In some aspects, the contour cutter further comprises at least one blade structure which is slidingly attached to an outer boundary such that it may be raised and lowered within the contour cutter, and facilitates creation of a desired contour within the implantation site.

Referring for example to FIG. 18, the contour cutter possesses two blade structures. In some aspects, the blade structure/s are initially raised and may be subsequently lowered using a specialized tool/mallet as further described. In some aspects, the contour cutter will further comprise rounded termini to insert within the rounded boundaries of the prepared implant site.

In some aspects, the blades are lowered within the contour cutter, and ultimately cutting underlying tissue in a highly controlled manner, in part owing to the positioning of same within defined grooves in the contour cutter and optionally via use of a specific and appropriately sized mallet, which lowers same. In some aspects, the mallet will further comprise a central hollow, which in turn may be threaded over the immobilizing structure, as well, with the long axis of the mallet head being in a perpendicular orientation to that of the long axis of the contour cutter, further promoting controlled use of same.

It will be appreciated that the mallet head may be of any appropriate size and geometry, which is effective to lower the blades of the contour cutter to effectively cut/shape the boundaries of the underlying tissue.

Figure 19A:
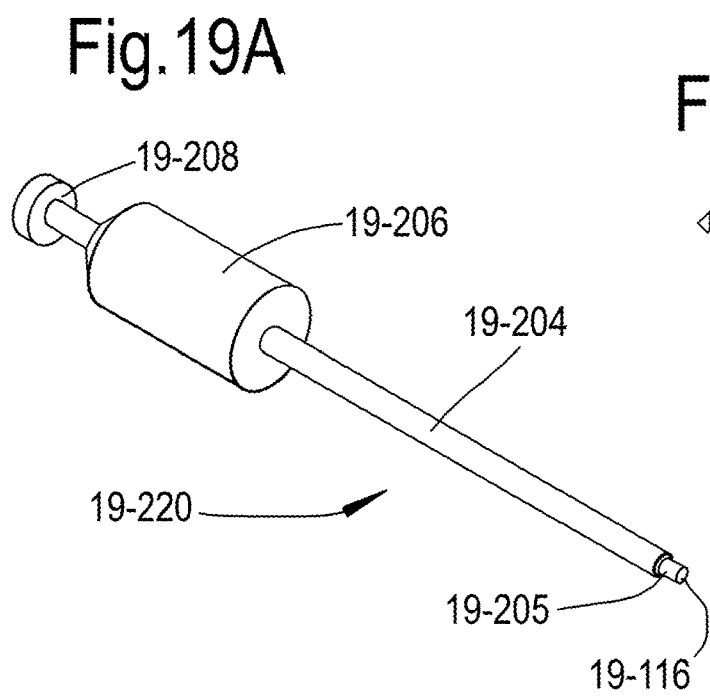
Figure 19B:
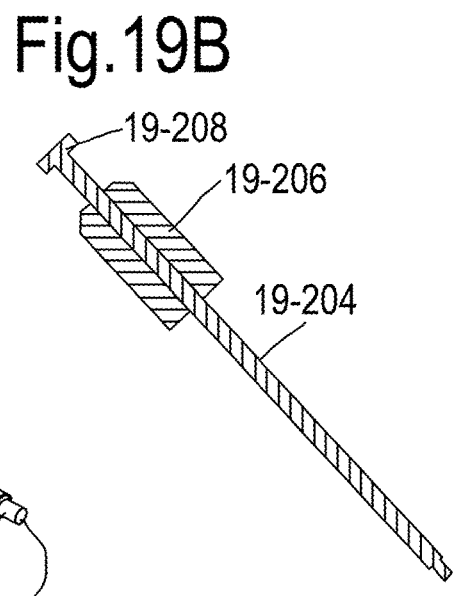

In some aspects, in order to smoothly and carefully remove the contour cutter and avoid in any way altering the now prepared implant site, a slide hammer may be further fittedly affixed to the contour cutter. An embodied version of the slide hammer is shown in FIG. 19, which further comprises a stopper for controlled and safest removal of the contour cutter.

In some aspects, the slide hammer may further comprise a fitted insertion tip for insertion in a fitted manner within a recess in the contour cutter for ease of removal of the contour cutter. In some aspects, the press fit is sufficiently fitted to enable extraction of the contour cutter. In some aspects, the recess is threaded, as is the insertion tip in a complementary fashion to promote a more specific fit for the slide hammer within the contour cutter.

Once the contour cutter is removed, a smooth, large implant site remains, and a desired implant may be manually inserted therein.

In some aspects, this invention provides a tamper.
In some aspects, the tamper comprises:
a first region having an outer boundary substantially ovoid in shape and a basal surface comprising a radius of curvature complementary to a radius of curvature of a tissue to which said curved alignment and positioning tissue extraction base is being affixed and comprising a non-stick material on at least a portion of an exposed region of said basal surface;
a second region comprising a gripping part located distally to said first region; and
an elongated shaft positioned between said first region and said second region.

The tamper, in some embodiments, comprises a first region comprising a solid base and further comprises a flexible cover attached to the solid base. In some aspects, the flexible cover comprises a radius of curvature complementary to the radius of curvature of a tissue to which said curved alignment and positioning tissue extraction base is being affixed.

In some aspects, the solid base cover comprises a radius of curvature complementary to the radius of curvature of a tissue to which said curved alignment and positioning tissue extraction base is being affixed.

In some aspects, a basal surface of the solid base is flat, and the radius of curvature of the first region is present in the flexible cover alone.

In some embodiments, this invention provides a kit of parts comprising any complement of tools as herein described.

In some embodiments, the kit of parts will comprise one or more curved alignment and positioning tissue extraction bases. In some embodiments a kit of this invention will comprise a series of curved alignment and positioning tissue extraction bases or jig bases, from which all potential angles of curvature are represented for a given implantation procedure to promote kit versatility for the surgeon.

In some aspects, such kit may further comprise handle, as herein described.

In some aspects, such kit may further comprise a full complement of immobilizing structures/rod-shaped structures, which are, in some embodiments, K-wires, or in some embodiments, a similar structure with a terminal modification that inserts within tissue in a stable manner Such complement may have structures of varied lengths, or in some embodiments, tips that vary in terms of the presence of a "screw-like structure" or pointed tip, being of varied diameters, or any combination thereof.

In some embodiments, the kit may further comprise one or more "lockers" as herein described, wherein the lockers may vary in terms of their lengths, shaft diameters, size of the locker heads, as well as varying in terms of their locking mechanism, as will be appreciated by the skilled artisan. Any complement of lockers is envisioned as being appropriate for inclusion in a kit of this invention.

In some embodiments such kit may comprise a specialized bit as herein described.

In some embodiments, the kits of this invention may comprise one or more perpendicular implantation aligners as herein described.

In some aspects, the kit will comprise perpendicular implantation aligners which vary in terms of the number of and positioning of the shaft/s in the aligners, or in some embodiments, the perpendicular implantation aligners will vary in terms of the overall dimensions of the aligners, or in some embodiments, the kits of this invention may comprise a complement of aligners differing in terms of any combination of such features.

Such kits may further comprise any complement of immobilizing structures/rod-shaped structures, as herein described.

Such kits may further comprise a one or more curved alignment and positioning tissue extraction bases, as herein described, and optionally further comprise a handle for insertion therein as herein described, and optionally further comprise one or more lockers as herein described.

In some embodiments, the kits may comprise one or more drill bit protective sheaths as herein described. In some embodiments, such drill bit protective sheaths may vary in terms of overall dimensions or shape, or in some embodiments, such drill bit protective sheaths may vary in terms of the number of barrels in same, or in some embodiments, the kits may comprise any permutation/embodiment of same.

In some embodiments, such kits may further comprise a specialized drill bit as herein described. In some embodiments, such kits may further comprise a tissue reamer/shaper as herein described. In some embodiments, such kits may further comprise one or more perpendicular implantation aligners as herein described.

In some embodiments, such kits may further comprise one or more curved alignment and positioning tissue extraction bases, as herein described, and optionally further comprise a handle for insertion therein as herein described, and optionally further comprise one or more lockers as herein described.

In some embodiments, such kits may further comprise any complement of immobilizing structures/rod-shaped structures, as herein described.

In some embodiments, this invention provides a kit comprising one or more contour cutters as herein described. In some embodiments, such kit may further comprise a mallet as herein described and in some embodiments, such kit may comprise one or more slide hammers as herein described.

In some embodiments, such kits may further comprise any complement of immobilizing structures/rod-shaped structures, as herein described.

In some embodiments, such kits may further comprise one or more curved alignment and positioning tissue extraction bases, as herein described, and optionally further comprise a handle for insertion therein as herein described, and optionally further comprise one or more lockers as herein described.

In some embodiments, such kits may further comprise one or more drill bit protective sheaths as herein described. In some embodiments, such drill bit protective sheaths may vary in terms of overall dimensions or shape, or in some embodiments, such drill bit protective sheaths may vary in terms of the number of barrels in same, or in some embodiments, the kits may comprise any permutation/embodiment of same.

In some embodiments, such kits may further comprise a specialized drill bit as herein described. In some embodiments, such kits may further comprise a tissue reamer/shaper as herein described.

In some embodiments, this invention provides a kit comprising one or more tampers as herein described. In some embodiments, such tampers may vary in terms of the angle of curvature of a basal surface of the tampers as herein described. In some aspects, the tampers may vary in terms of the size and dimension of such tampers. In some embodiments, the kit may comprise a combination of any embodied tamper as herein described.

In some embodiments, such kits may further comprise one or more contour cutters as herein described. In some embodiments, such kit may further comprise a mallet as herein described and in some embodiments, such kit may comprise one or more slide hammers as herein described.

In some embodiments, such kits may further comprise any complement of immobilizing structures/rod-shaped structures, as herein described.

In some embodiments, such kits will comprise any complement of solid substrates as herein described and optionally, may further comprise any biocompatible polymer as herein described, and hyaluronic acid is in particular envisioned in this context.

In some embodiments, such kits may further comprise one or more curved alignment and positioning tissue extraction bases, as herein described, and optionally further comprise a handle for insertion therein as herein described, and optionally further comprise one or more lockers as herein described.

In some embodiments, such kits may further comprise one or more drill bit protective sheaths as herein described. In some embodiments, such drill bit protective sheaths may vary in terms of overall dimensions or shape, or in some embodiments, such drill bit protective sheaths may vary in terms of the number of barrels in same, or in some embodiments, the kits may comprise any permutation/embodiment of same.

In some embodiments, such kits may further comprise a specialized drill bit as herein described. In some embodiments, such kits may further comprise a tissue reamer/shaper as herein described.

It will be appreciated that a kit comprising any complement of tools as herein described is envisioned and to be considered as part of this invention.

In some embodiments, any kit as herein described may further comprise one or more implants as herein described and in some embodiments, such kits may comprise a full complement of implants as herein described.

In some embodiments, such kits will comprise any complement of solid substrates as herein described and optionally, may further comprise any biocompatible polymer as herein described, and hyaluronic acid is in particular envisioned in this context.

In some embodiments, the methods of this invention further comprise matching an optimized solid substrate in terms of its angle of taper to the angle of the tapered sides of the tissue shaper and alignment tool used in some embodiments of the methods of this invention.

In some embodiments, the methods of this invention include any method for tissue repair making use of a solid substrate or tool as herein described.

This invention specifically contemplates customized applications, wherein a solid substrate for implantation is specifically prepared in a customized manner to best fit a defect site in a subject in need of implantation of same.

In some aspects, this invention specifically contemplates that customization, in particular, with respect to implantation procedures within a curved tissue site in a subject include idealized preparation of a solid substrate for implantation, for example, via compiling information from a variety of sources such as MRI and/or CT scans, such that a plurality of medical images of a bone region with a defect area are obtained and converted into three-dimensional data.

In some aspects, such three-dimensional data in turn is used via automated systems to specifically machine an appropriate and idealized implant.

In some embodiments, such three-dimensional data in turn is used to facilitate selection of an implant from a variety of standard implants of varying dimensions and topographies, to promote selection of a best choice for implant from among a series of available implants.

In some embodiments, in either case, whereby a truly optimized implant is specifically and in a custom manner machined to ideally fit a subject, or an optimized implant reflective of a best fit from a wide variety of standards is chosen, the implant may further contain tapered sides as herein described and/or a rounded surface, as herein described.

In some aspects, this invention specifically contemplates that customization, in particular, with respect to implantation procedures within a curved tissue site in a subject include idealized preparation of a tool as herein described for implantation of the optimally selected, or fully customized implant, for example, via compiling information from a variety of sources such as MRI and/or CT scans, such that a plurality of medical images of a bone and/or cartilage region with a defect area are obtained and converted into three-dimensional data and tools for use in implantation in such defect site are therefore machined and prepared in a fully customized manner.

In some aspects, such three-dimensional data in turn is used via automated systems to specifically machine an appropriate and idealized tool.

In some embodiments, such three-dimensional data in turn is used to facilitate selection of an optimal tool from a variety of standard tools of varying dimensions and topographies, to promote selection of a best choice for implantation tools from among a series of available such tools.

In some embodiments, in either case, whereby a truly optimized tool is specifically selected and in a custom manner machined to ideally fit a subject, or an optimized tool reflective of a best fit from a wide variety of standards is chosen, the tools may further contain adaptations to specifically accommodate tapered sides of the implant as herein described and/or a rounded surface, as herein described.

Such substrate and tool custom preparation and/or selection allows for ideal design of a solid substrate and tool for implanting same in terms of its dimensions and for example, including a taper as herein described and/or an appropriate radius of curvature as herein described, and fabrication of same.

In some embodiments, the tools of this invention, in particular tools comprising a radius of curvature, as herein described are also fabricated via known methods to specifically provide a best fit for the subject tissue being manipulated in a highly customized manner.

This invention therefore provides a method for implantation of an optimized solid substrate for promoting cell or tissue growth or restored function in a subject in need thereof, said method comprising:

Isolating or preparing an optimized solid substrate for promoting cell or tissue growth or restored function, which solid substrate comprises a coral or coral derivative, is characterized by a specific fluid uptake capacity value of at least 75%, or is characterized by having a contact angle value of less than 60 degrees and which further comprises a radius of curvature complementary to a radius of curvature of a tissue surface to which said solid substrate is being applied;

establishing a specific fluid uptake capacity value of said solid substrate, which specific fluid uptake capacity value is determined by establishing a spontaneous fluid uptake value divided by a total fluid uptake value;

selecting a solid substrate characterized by a specific fluid uptake capacity value of at least 75% or is characterized by having a contact angle value of less than 60 degrees; and implanting said solid substrate characterized by a specific fluid uptake capacity value of at least 75% or is characterized by having a contact angle value of less than 60 degrees within a desired site in a subject, wherein said implanting is conducted by making use of at least one of the contour cutters as herein described, the curved alignment and positioning tissue extraction bases as herein described, the locker as herein described, the perpendicular implantation aligner as herein described, the drill bit protective sheath as herein described and the tamper as herein described or any combination thereof.

In some embodiments, according to this aspect, the method further comprises customizing a radius of curvature of a curved surface of at least one of the curved alignment and positioning tissue extraction bases as herein described, or the tampers as herein described, or at least one of the surfaces of the solid substrate characterized by a specific fluid uptake capacity value of at least 75%, or any combination thereof.

In some embodiments, such customization of the substrates and/or tools of this invention provide a best fit and idealized, customized procedure and substrates for implantation in a subject, promoting greater and more complete healing in the subject.

In some embodiments, the methods of this invention lend themselves to use of an automated system, suitable for use with any combination of the contour cutters as herein described, the curved alignment and positioning tissue extraction base as herein described, the locker as herein described, the perpendicular implantation aligner as herein described, the drill bit protective sheath as herein described, and the tamper as herein described, or any combination of same.

In some aspects, such automated systems are suitable for robotic assemblies to produce desired movements of the contour cutter as herein described, the curved alignment and positioning tissue extraction base as herein described, the locker as herein described, the perpendicular implantation aligner as herein described, the drill bit protective sheath as herein described and the tamper as herein described or any combination thereof so as to manipulate same in a surgical procedure in said method.

In some aspects, such automated systems are well established and allow for greater precision and control during surgical implantation procedures and may be further combined with the customized methods, implants and tools as herein described to provide idealized implantations and optimal results in a subject in need of same.

In some embodiments, the term "comprise" or grammatical forms thereof, refers to the inclusion of the indicated components of this invention, as well as inclusion of other active agents, and pharmaceutically acceptable carriers, excipients, emollients, stabilizers, etc., as are known in the pharmaceutical industry.

In one embodiment, the term "about" refers to a variance of from 1-10%, or in another embodiment, 5-15%, or in another embodiment, up to 10%, or in another embodiment, up to 25% variance from the indicated values, except where context indicates that the variance should not result in a value exceeding 100%.

In one embodiment, the present invention provides combined preparations. In one embodiment, the term "a combined preparation" defines especially a "kit of parts" in the sense that the combination partners as defined above can be used independently or in different combinations i.e., simultaneously, concurrently, separately or sequentially.

EXAMPLES

Example 1

Preparing Optimized Coralline-Based Solid Substrates of this Invention

Materials and Methods

A diamond saw was used to remove an outer coral layer, and large sections from which representative smaller sections of desired dimensions were cut from the coral block.

Coral from the hydrocoral *Porites lutea* which has an average pore size of 100-150 μm was harvested from various regions within a coral. The coral was evaluated visually for its appearance, density, and porosity. Coral was then optionally immersed in 5% sodium hypochlorite for removal of external organic tissue. Briefly, coral was first exposed to a 5% sodium hypochlorite solution for 30 minutes, 3 exchanges at temperature range of from RT-50° C., and sub-atmospheric pressure using vacuum pressure ranging from 0.2-0.00001 Bar. The coral sections were then exposed to a 10% solution of hydrogen peroxide for 15 minutes at a temperature range of from RT-50° C., and subatmospheric pressure using vacuum pressure ranging from 0.2-0.00001 Bar. The cleaned sections were then washed in distilled water for 30 minutes, 3 exchanges at a temperature range of from RT-50° C., and sub-atmospheric pressure using vacuum pressure ranging from 0.3-0.00001 Bar.

The coral was optionally sterilized by exposure to gamma radiation at a strength of at least 22.5 kGy and can then be stored aseptically, in packaging material, and in particular, the smaller samples were irradiated, whereas larger blocks assessed were not irradiated.

Each section was then place in a plastic petri dish and 2 ml of fluid was applied to each dish. Observations regarding absorption of the fluid were recorded. Fluids used included animal blood, plasma, water and various colored solutions.

Coral samples with substantial absorption throughout the structure were used.

Additional coral samples were taken from identical regions as to those thus identified above as absorptive, and the samples were isolated and machined to a desired size and shape, then dried.

A dry weight for each sample was recorded.

Water was added to each assay container in an approximately 1:1 ratio or slightly more, i.e. equal to or slightly more than the size of the sample in mm as compared to the volume of fluid in ml is added to the container.

The sample was then weighed and a spontaneous fluid uptake value determined.

A significantly increased amount of fluid was then brought into contact with the sample and a vacuum applied for a period of time to ensure maximal uptake of the applied fluid into the coral sample, and total fluid uptake capacity was assessed and the specific fluid uptake capacity value determined by dividing the spontaneous fluid uptake value by the total fluid uptake capacity. Samples with a value of 75% or more were selected.

Samples were then further machined into a cylindrical shape (FIG. 1A) or a substantially conical shape (FIG. 1B), cleaned, sterilized and hydrogel was aseptically added.

In order to further appreciate the difference imparted to the structure by the tapering of the sides of the substrate, a vertical line is drawn in each figure parallel to a longitudinal axis through the solid substrate for ease of viewing. As is readily evident, the sides of the cylindrical substrate are essentially parallel to the drawn line, whereas the sides of the substantially conical substrate are tapered, with sides at an angle of about 2 degrees from the line drawn.

Example 2

Improved Solid Substrate Incorporation as a Function of the Presence of Tapered Sides Specifically at a Two Degree Angle Along a Longitudinal Axis in the Coralline-Based Solid Substrates of this Invention In order to assess the consequence of the structural variability in the plugs of Example 1, coral plugs were prepared were prepared as described in Example 1.

Tapered implants were prepared as described in Example 1, for evaluation of their effect in ex-vivo porcine bone models of repair. The same were compared to cylindrical shaped implants without tapered sides.

Perpendicularity relative to the articular surface, in the center of the lesion, was determined using tools as described in PCT International Application Number WO 2014/072982, fully incorporated by reference herein. Using a motorized drill, a 2.5 mm K-wire was inserted through the Alignment tool into the center of the lesion. The K-wire was advanced up until the indicator line reached the proximal end of the Alignment tool, and then the drill was disengaged from the K-wire, and the Alignment tool removed, leaving the K-wire in place.

The Drill Protective sheath was then placed over the K-wire and the Drill Bit threaded onto the Drill Protective sheath over the K-wire, at which point the motorized drill is activated and engaged until reaching a stop-indicator line. The Drill Bit and Drill Protective sheath were then removed, leaving the K-wire in place.

The Reamer was next inserted over the K-wire, and rotated clockwise, and advanced forward until the laser mark indicator line reached the articular cartilage level, and then removed, providing the desired depth for the implant site. The Shaper/Reamer was then inserted over the K-wire, rotated clockwise and advanced forward until the laser mark indicator line reached the articular cartilage level, as well, and then removed, followed by removal of the K-wire. No loose or untrimmed tissue remnants were left remaining in the implant site.

Conic implants (15 mmD×10 mmL) prepared as in Example 1, containing tapered sides angled at an angle of 1°, 2°, 3°, 4° and 5° were evaluated.

The implants were gently, manually fit within the implant site created, as described hereinabove, and ensuring an orientation perpendicular to the implant site surface. Implants were manually advanced as far as possible, and a Tamper was used to further advance same.

Implantation of the substantially conical implants was associated with a typically shorter implantation procedure time, greater ease of insertion, and no implant breakage events occurred. In contrast, implantation of substantially cylindrical implants was associated with a longer procedure time, and greater insertion difficulty, including instances of breakage of the implant during its introduction within the implantation site.

Example 3

Tools and Ideal Implantation Protocols for the Optimized Substantially Conical Coralline-Based Solid Substrates for Implantation The optimized substrate as described in Example 2 may be implanted in a defect site, and it will be appreciated that such implants may be scaled to size, while still preserving the 2 degree optimal taper angle for the sides of the substantially conical implant.

Figure 2:
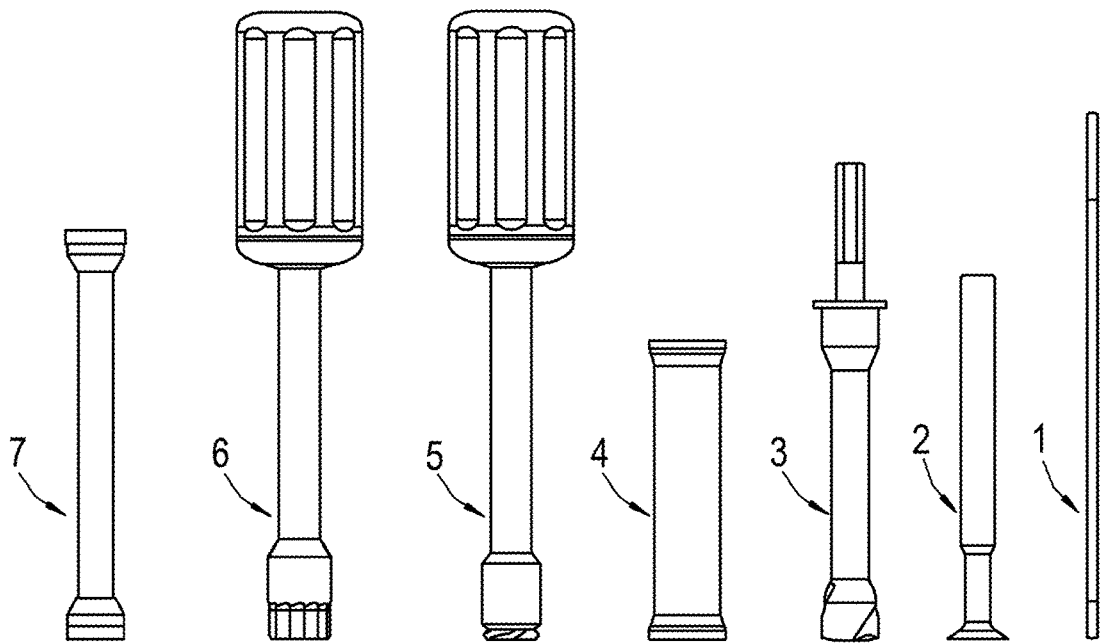
FIG. 2 schematically depicts a complement of tools which may be used in an implantation procedure for implantation of a solid substrate/implant as herein described.

A putative complement of tools is presented in FIG. 2. From right to left, is shown a rod-like structure (tool number 1), an implantation stabilization tool (tool number 2), a drill bit and protective sheath (tools number 3 and 4, respectively), a reamer (tool number 5), a shaper (tool number 6) and a tamper (tool number 7).

In some aspect, a rod-like structure, such as a K-wire, is initially inserted and stabilized within a desired site of implantation (FIG. 2, tool number 1). The rod-like structure is any structure so-shaped and sized as to be appropriate for surgical insertion within a tissue, for example, screws, pins, molly or molly bolt or a drill bit, which may, for example, remain inserted, and any anchored version of the same, e.g. anchor, hook, or other similar structure, as will be appreciated by the skilled artisan.

Figure 3A:
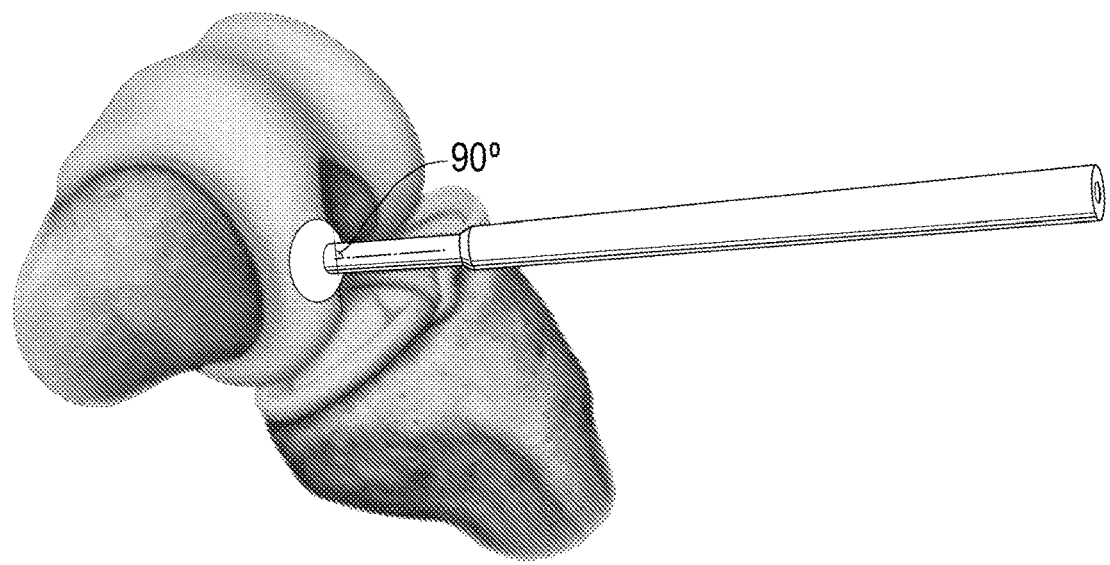
FIG. 3A-3B schematically depict the insertion of a K-wire and implantation alignment tool for the insertion of the K-wire in a perpendicular orientation within a desired implantation site.
Figure 3B:
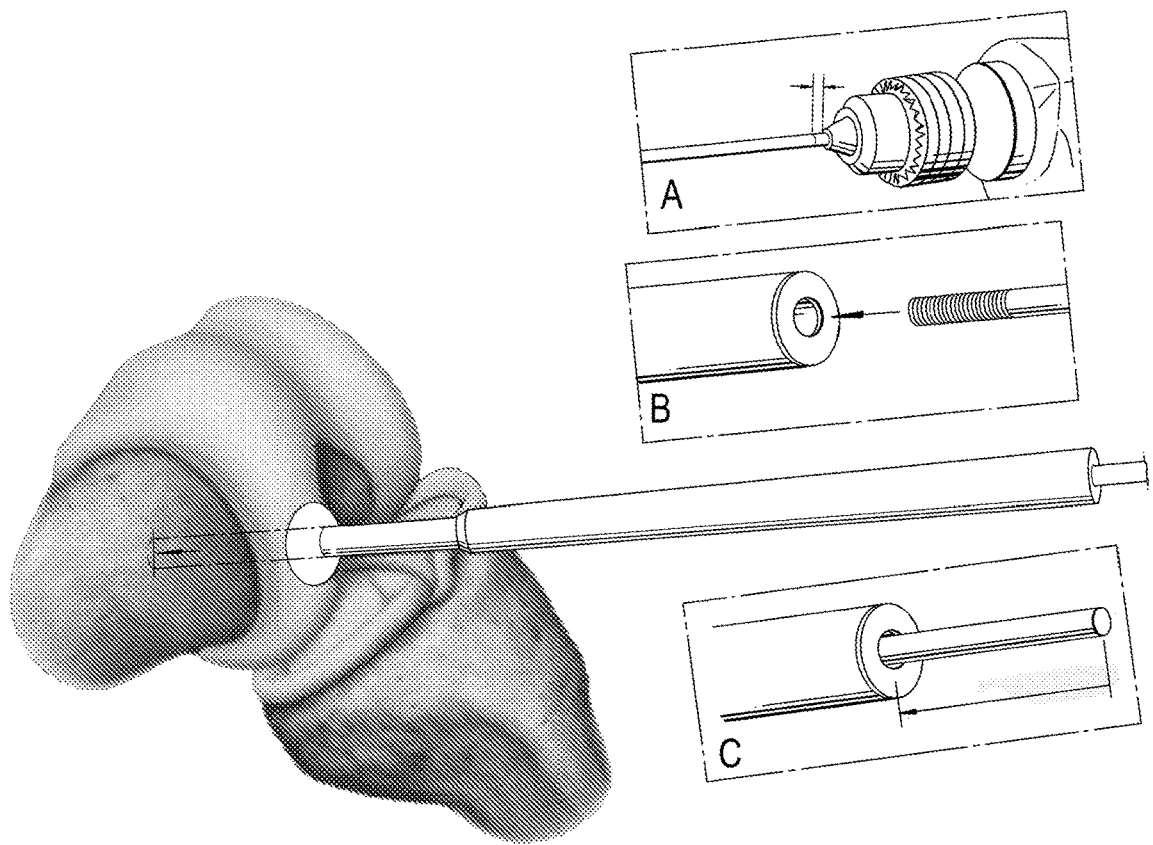
Figure 4A:
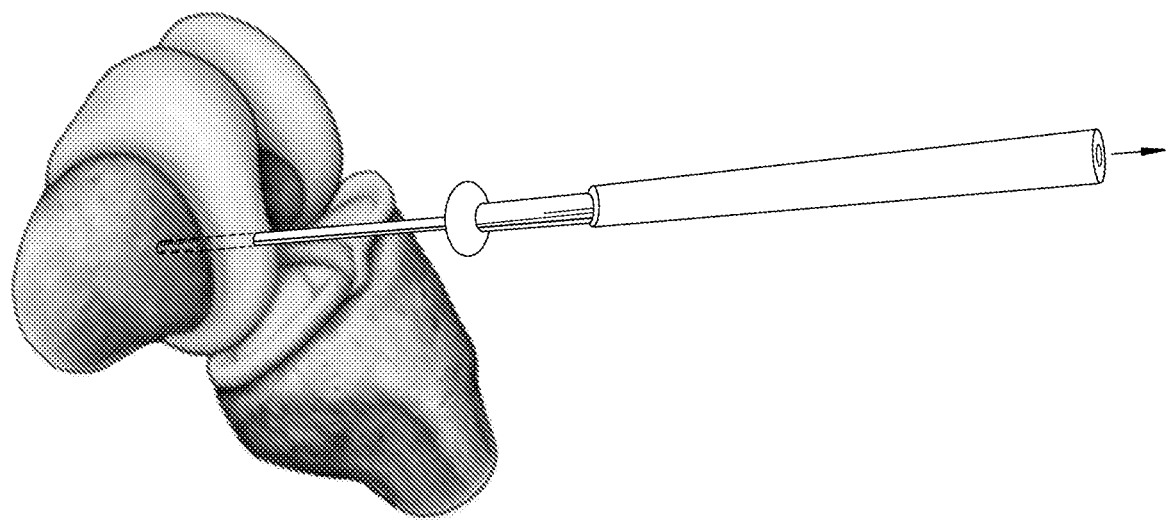
FIG. 4A-4B schematically depict the possible removal of the alignment tool and fitting of a drill bit protective sheath over the K-wire.
Figure 4B:
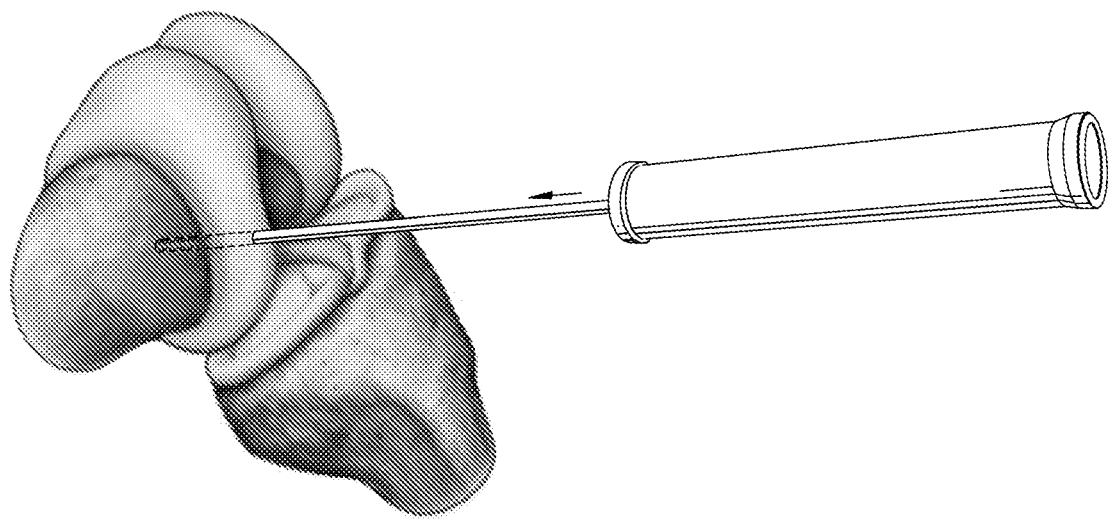

The rod-like structure is inserted, positioned and stabilized in a perpendicular orientation relative to the implantation location (articular surface). In some embodiments, such rod-like structure is threaded through an implantation tool stabilizing implement (FIG. 2, tool number 2; and FIG. 3A) and anchored into the bone with a resulting perpendicular orientation relative to the articular surface. It will be appreciated that any implantation tool set may be used, for example, those described in PCT International Patent Application Publication Number WO 2014072982, which is fully incorporated herein by reference.

Such implantation tool stabilizing implement will comprise a stabilizing contact structure with an at least partially circular concave single piece structure, suitable for placement proximally to an articular surface, and the contact structure serves the function of ensuring a desired orientation of the implement with respect to a plane of the target surface. The implantation tool stabilizing implement is a cannulated tool, allowing for the rod-like structure to be threaded therethrough.

Figure 5A:
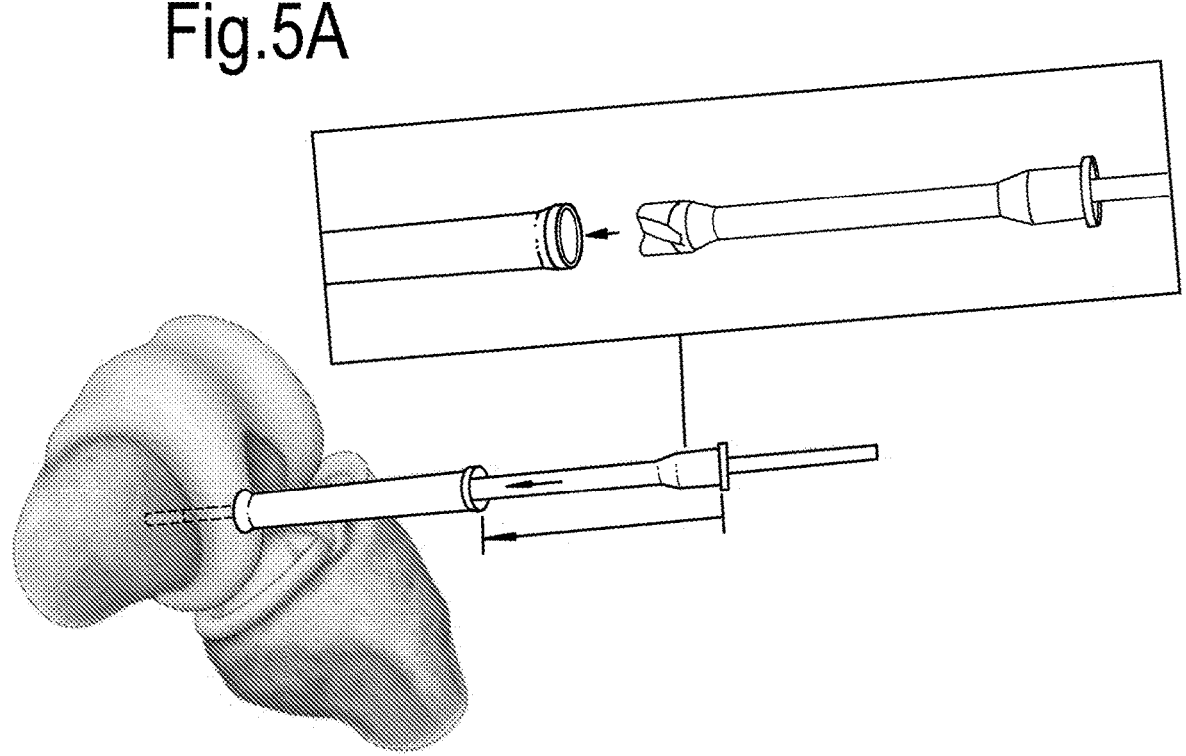
FIG. 5A-5B schematically depict the insertion of a drill bit assembly including insertion within a drill bit protective sheath for creation of a void in preparation of the site for implantation and ultimate removal of same.

While the K-wire is initially placed within the site of implantation, the site is further prepared by drilling and thereby enlarging the tissue site, using a drill bit, which in turn may be cannulated to fit over the K-wire (FIG. 2, tool number 3). The drill bit is connected to a drill. Such drill bit may be first placed within a drill bit protective sheath (FIG. 2, tool number 4 or FIG. 5A, panel B), both of which are cannulated (FIG. 5A), to be positioned over the K-wire ensuring the perpendicular orientation when drilling.

Figure 5B:
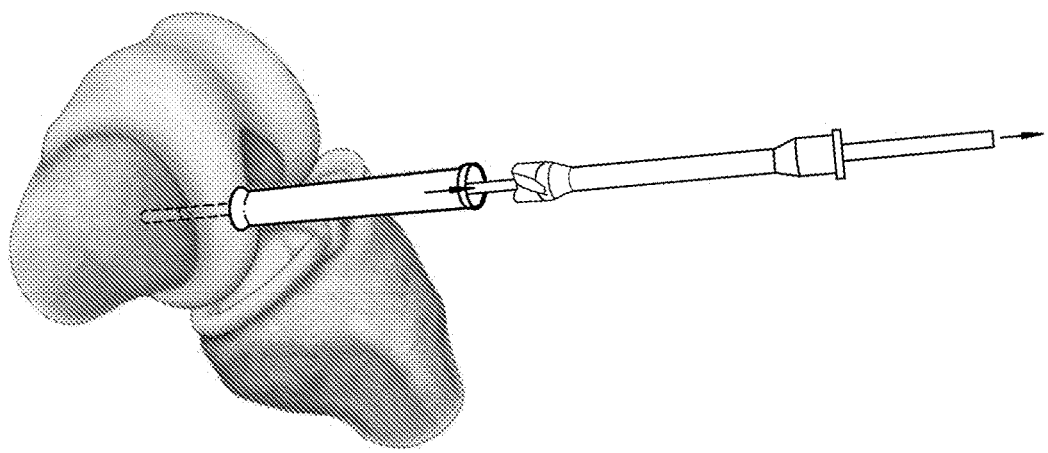

The drill bit and sheath, as well as the stabilization tool may all be removed and the next tool may be inserted over the K-wire (FIG. 5B).

In other aspects, the stabilization tool may be removed and a drill bit protective sheath is placed over the K-wire, with the drill bit threaded on the K-wire and located within the protective sheath.

Following removal of the drill bit and protective sheath from over the rod-like structure bit protective sheath over the drill bit and attachment of the assembly (FIG. 5B) the hole or void in the desired target tissue having a desired depth has been created.

Figure 6A:
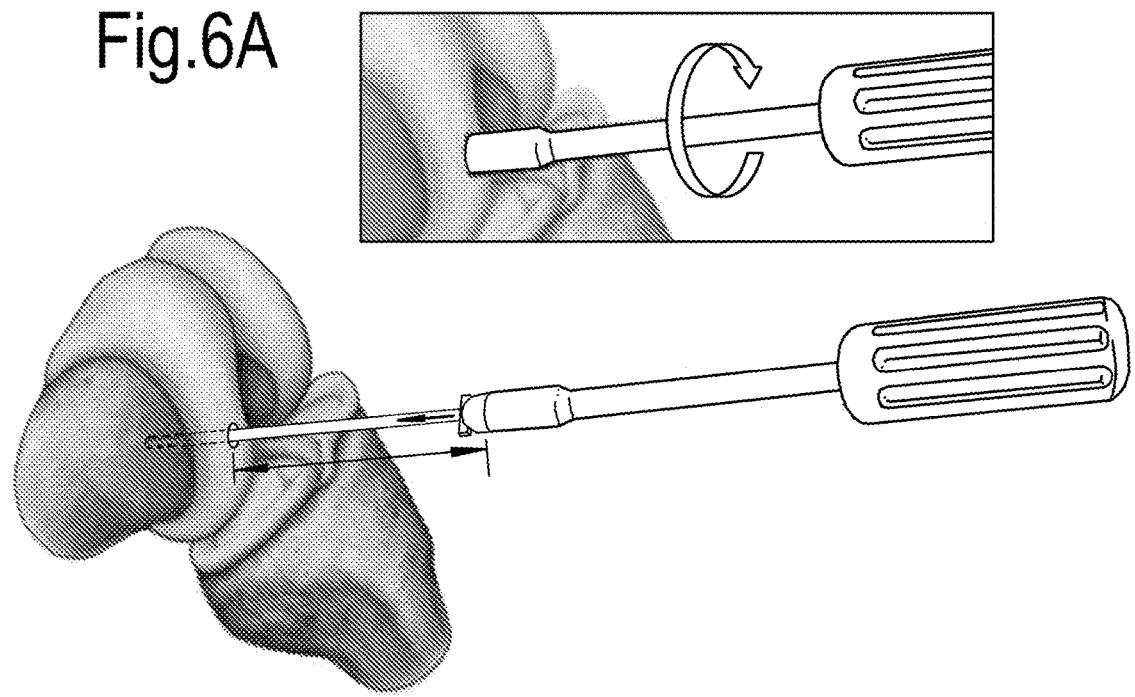
FIG. 6A-6B schematically depicts the insertion, rotation and ultimate removal of a tissue reamer for further creation of a void and early shaping of same in preparation of the site for implantation.
Figure 6B:
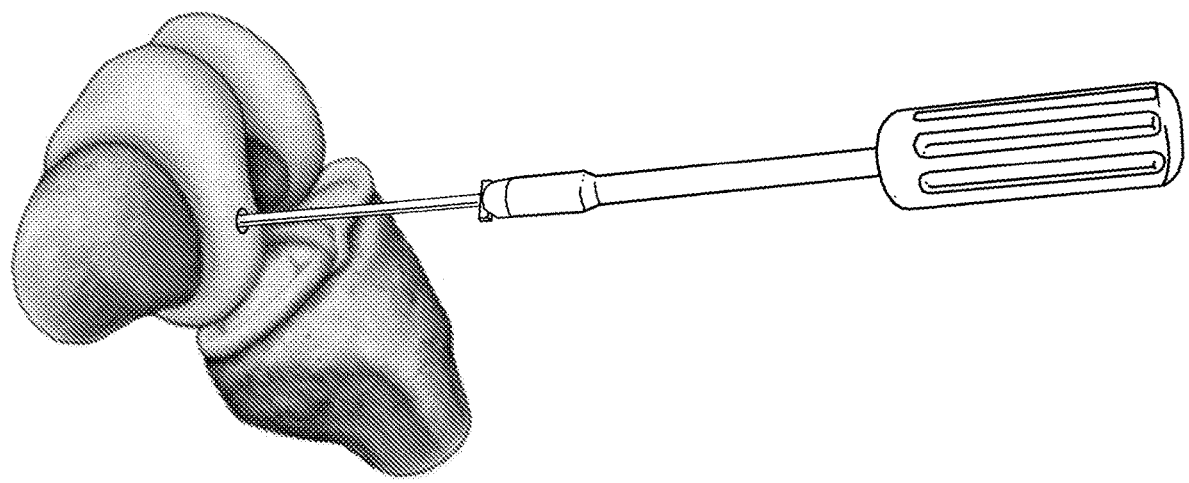

A tissue reamer (FIG. 2, tool number 5) is then used to further harvest undesirable tissue at the implantation site and/or to smooth the walls of the implantation site and/or deepen the hole to the desired depth in preparation for implantation of a solid substrate as herein described (FIG. 6A). The reamer is also a cannulated tool which inserts over the K-wire, and rotation about the axis as noted in the inset facilitates the harvesting and/or shaping as described. The reamer is then removed off the K-wire, as depicted in FIG. 6B.

Figure 7A:
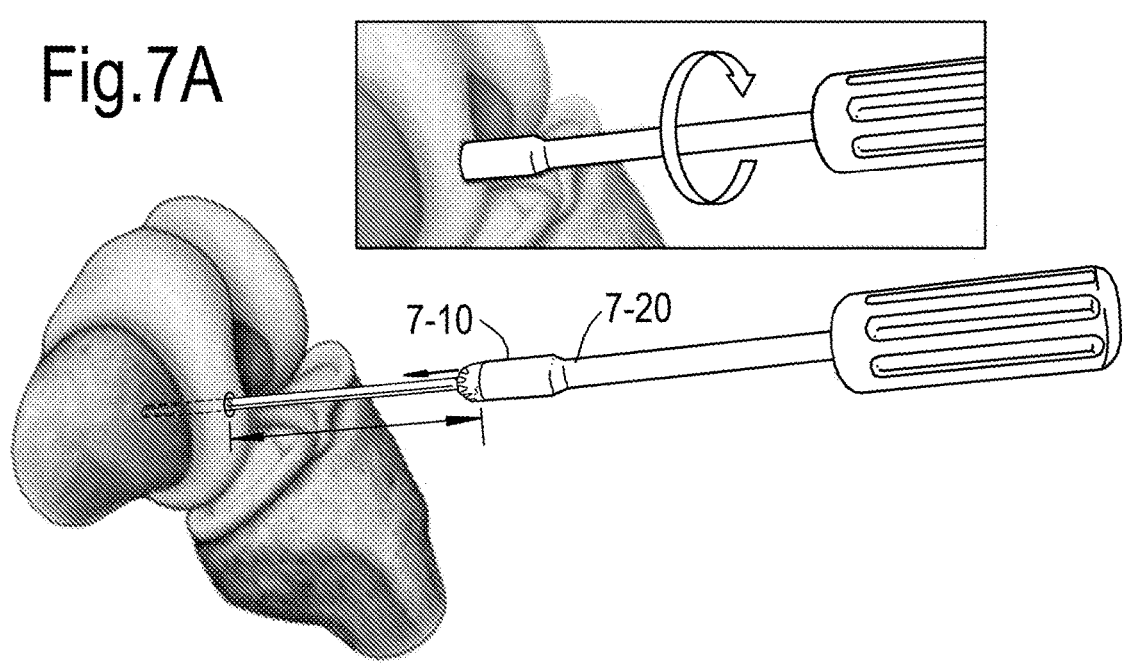
FIG. 7A-7D schematically depicts the insertion, rotation and ultimate removal of a tissue shaper and alignment tool of this invention.

FIG. 7A depicts an embodied tissue shaper and alignment tool of this invention (also depicted in FIG. 2, tool number 6). The tissue shaper and alignment tool is a cannulated tool which inserts over the K-wire, and with its implementation, for example, rotation about the indicated axis, the sides of the implantation site are smoothed, as well as prepared as a tapered site for the accommodation of the substantially conical implants of this invention.

Figure 7B:
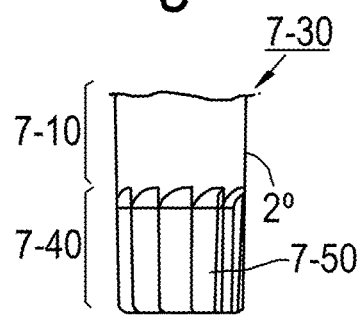

FIG. 7B shows the first shaping region 7-10 located proximal to said joint region 7-20, which first shaping region is substantially smooth. The second shaping region 7-40 is also shown, located distal to said joint region, which second shaping region comprises a series of laterally extending protrusions 7-50, and has tapered sides at an angle of two degrees from a longitudinal axis of said tool.

Following removal of the tissue shaper (FIG. 7D), the site is ready for insertion of the solid substrates of this invention.

FIG. 8, panels A-D show selection of an implant of this invention, and manual fitting and advancement of same within a desired implantation site. It is also possible that the K-wire is maintained in the defect site that the implant is cannulated and manually fed over the K-wire and then advanced into place, as described.

Figure 9A:
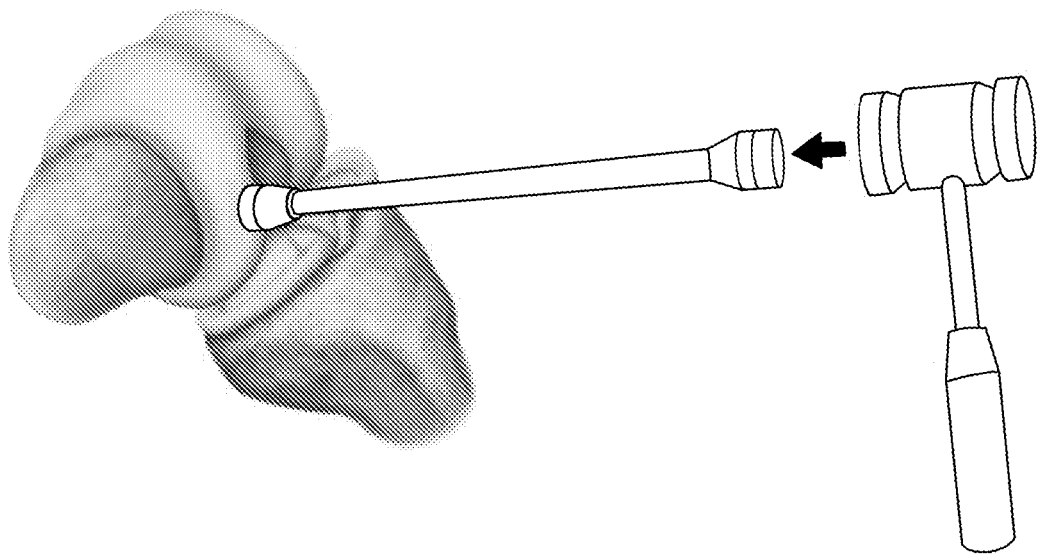
FIG. 9A-9B schematically depict the use of one embodiment of a tamper to fully advance the implant as herein described within the desired implantation site.
Figure 9B:
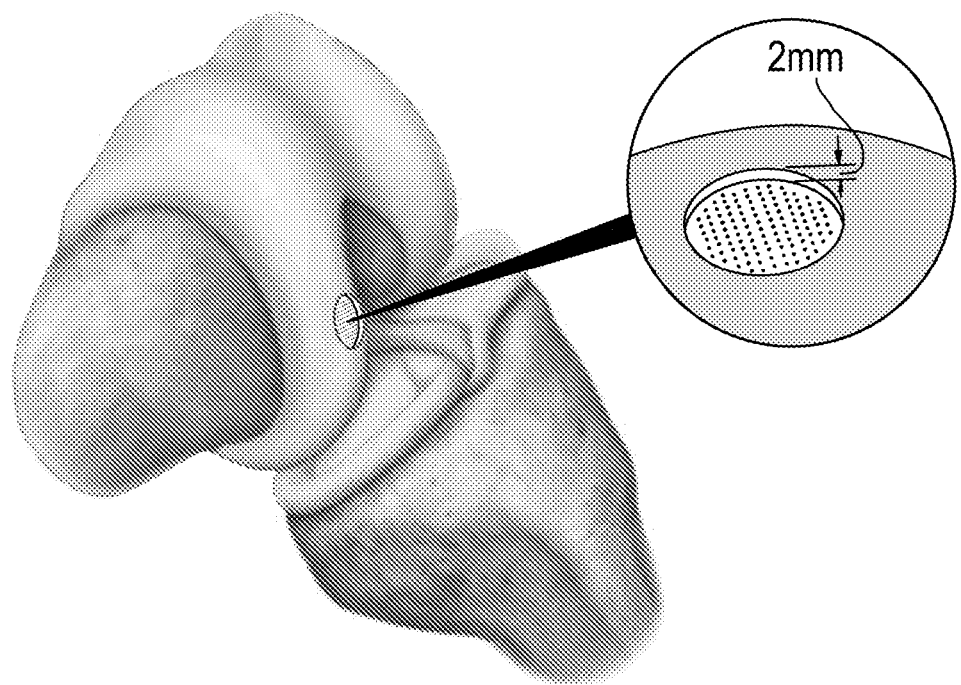

FIG. 9A shows final advancement of the implant with the use of a tamper (also depicted in FIG. 2, tool number 7), inserting the implant so that it is fit just below the lip of the implantation site, as shown in the Figure, for example, being 2 mm below the surface of same.

In some aspects, the optionally comprises a terminally located gripper, and a modified head, such that the tamper and implant are cannulated and can be placed over the rod like structure within the void, and force may be applied to the tamper terminus for optimum fit of the implant within the implantation site.

In some aspects, the methods will be understood to contemplate the addition of a biocompatible polymer to the solid substrates being implanted, which addition can be prior to the implantation or such addition may occur in situ, during the implantation procedure at a desired time. According to this aspect, hyaluronic acid is specifically contemplated as being the biocompatible polymer that may be incorporated within the substrate prior to implantation or may be supplemented in situ and applied to the implant during the implantation procedure. In some embodiments, the biocompatible polymer is added to a top surface of said solid substrate during the implantation procedure.

Example 4

Tools and Ideal Implantation Protocols for Implantation of an Optimized Coralline-Based Solid Substrate within a Condyle A substrate, for example, an optimized substrate as described in Example 2 may be implanted in a defect site, and it will be appreciated that such implants may be scaled to size, while still preserving the 2 degree optimal taper angle for the sides of the substantially conical implant.

In this example, tools and implants specifically suited for implantation within a condyle are shown, however, the skilled artisan will appreciate that shaped solid implants for insertion within osteochondral or bone and/or cartilage tissue at other sites can be readily accomplished to provide optimal fit and repair, using this example as a guide for same.

In some embodiments, the tools and procedures as described herein are appropriate for implantation of a tapered implant, and in some embodiments, the tools and procedures as described herein are appropriate for implantation of a solid substrate that is appropriately sized and of an appropriate shape for implantation in a subject, although the implant may not be tapered.

In some embodiments, the tools and procedures as described herein are appropriate for implantation within a curved tissue site.

Figure 10:
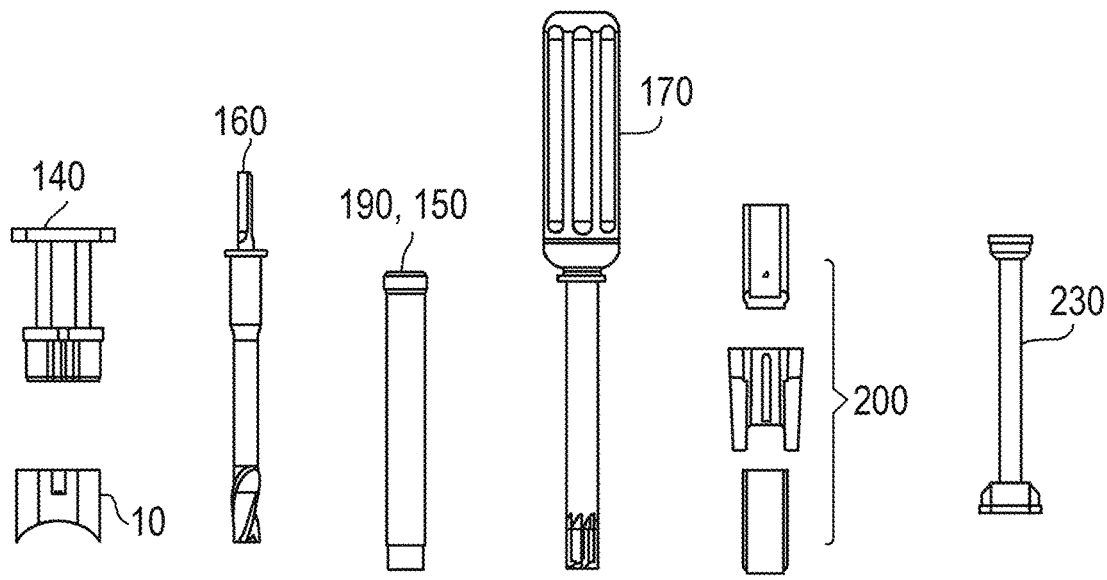
FIG. 10 schematically depicts an embodied complement of tools for use in implantation of ovoid shaped implants. From left to right is shown a "curved alignment and positioning tissue extraction base" also referred to herein as a "jig base" (tool number 10), a perpendicular implantation aligner (tool number 140), a drill bit (tool number 160) and drill bit protective sheath (tool number 150, 190), a reamer/shaper (tool number 170) and contour cutter (tool number 18-200) as well as a tamper (tool number 230) are shown. Each of these instruments is described further hereinbelow.

A putative complement of tools is presented in FIG. 10. From left to right is shown a "jig base" also referred to herein as a "curved alignment and positioning tissue extraction base" or as (tool number 11-10), a perpendicular aligner (tool number 13-140), a drill bit (tool number 14-160) and protective sheath (tool number 15-170), a reamer/shaper (tool number 15-170) and cutter/edge smoother (tool number 18-200) as well as a tamper (tool number 20-230) are shown. Each of these instruments is described further hereinbelow.

In one aspect, the tools are suited for an implantation procedure in a condyle. In some aspects, as will be appreciated, the condyle possesses a curvature, such that modified tools specifically fitted to such curvature are provided, which in turn promote better incorporation of an applied implant to such curved site.

In one aspect, the invention specifically provides such curved alignment tools. In one aspect, the invention promotes the applying of a curved alignment and positioning tissue extraction base to the curved condyle, which further provides for a stabilization of same. In some aspects, the curvature radius of the condyle is matched in terms of the choice of curved alignment and positioning tissue extraction base 11-10, having a complementary radius of curvature, as well.

FIG. 11 provides several views of a jig base (11-10). FIG. 11A shows a side view of the jig base, highlighting the curved alignment/positioning aspect of the tool, which contains a terminal modification (11-20) at the region in contact with the defect site, so that an ideal fit/positioning with respect to same is accomplished.

Figure 11J:
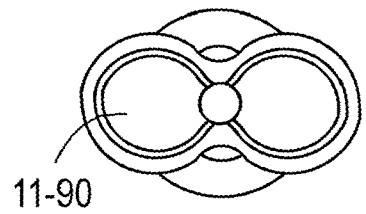

The jig base may be applied to the appropriate tissue defect site by means of a handle 11-70 (FIG. 11I), which may possess terminal modifications (11-80, 11-90) which modification part 11-90 inserts within a void or space 11-60 in the jig base, and may further contain a stopper 11-80, which ensures that the handle is only advanced to a desired depth within the jig base. FIG. 11B shows a cross section of the view in FIG. 11A. Insertion of the immobilizing structure through 11-30, for insertion within underlying tissue is shown. FIG. 11C and FIG. 11D show top and side perspective views, respectively of the jig base, identifying the regions for insert 11-60 of the terminal modification 11-90 of the handle. Also shown is the positioning of element 11-30 discussed further hereinbelow. FIG. 11J shows a bottom view of the terminal modifications of the handle, where the stopper element is evident, as well.

As will be appreciated, the jig base will be applied to a surface that may be rounded and the terminal part of the base 11-20 will be rounded to accommodate a best fit with respect to same. In some aspects, such rounding of the tissue surface to which the jig base is applied is rounded in a symmetrical fashion, and referring to FIGS. 11E-11H, in some aspects, as the surface to which the jig base may be applied is asymmetrically rounded, the jig base bottom 11-20 may be rounded in a substantially similar manner, to accommodate same. FIGS. 11E and 11G show side views whereby the base 11-20 has an angle of curvature that is asymmetrically rounded or partially rounded, as will be appreciated by the skilled artisan.

The jig base may be stably applied and affixed to the defect site, by, for example, fitting the curvature 11-20 to that of the defect site, and immobilizing the jig base to the tissue site. FIG. 11K depicts use of the handle to insert within the jig base, wherein the handle is stably inserted within the jig base.

In one aspect, the jig base will comprise lateral modifications 11-30 into which an immobilizing structure can be inserted, for example, a tissue screw or K-wire 11-100, 21-100, which insert through the jig base and reaches into underlying tissue, thereby affixing the jig base to the tissue site.

FIG. 11L shows insertion of an immobilizing structure 11-100 within the lateral modifications 11-30 of the jig base 11-10. It will be appreciated that the immobilizing structure can be a simple pointed structure, such as a K-wire, or in some aspects, the structure may have terminal modifications such as screw-like projections or laterally extending protrusions, to better grip/attach to the underlying tissue into which it is inserted.

In some aspects, the lateral modifications may be oriented in a manner such that the immobilizing structure inserts within the underlying tissue in a region that is interior to the outer defect margins, such that any additional "holes" or insertion in underlying tissue will fall in a region within which tissue will be remodeled. For example, and in some embodiments, the immobilizing structure inserts within the underlying tissue in a region over which an implant is placed, and this region is not exposed following insertion of an implant within the defect site. In some embodiments, the lateral modifications may be slanted or angled to promote specific/insertion of the immobilizing structure on an angle, as well, so that same is specifically inserted within the underlying tissue region over which the implant will be placed.

In some aspects, a specialized bit 11-110 may be used to specifically affix the immobilizing structure within the underlying tissue. (FIG. 11L). In some aspects, the specialized bit fits standard drills and other tools for insertion within tissue.

FIGS. 11M-11O depict different aspects of the specialized bit 11-110. The specialized bit 11-110 contains a centralized hollow region 11-116, sized such that an immobilizing structure inserts therethrough. The specialized bit has a proximal region 11-114 to which a standard drill may be attached and a wider base region 11-112, which is distal to same.

Figure 12A:
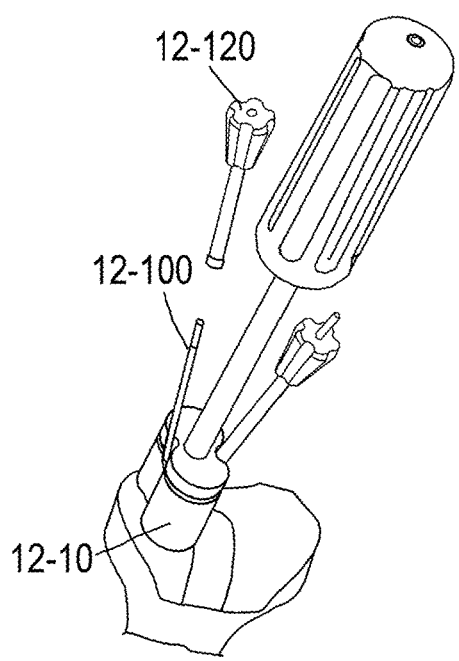
Figure 12B:
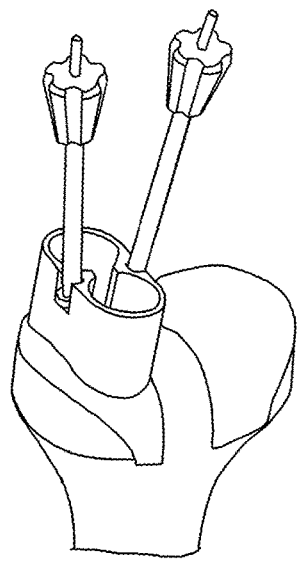
Figure 12C:
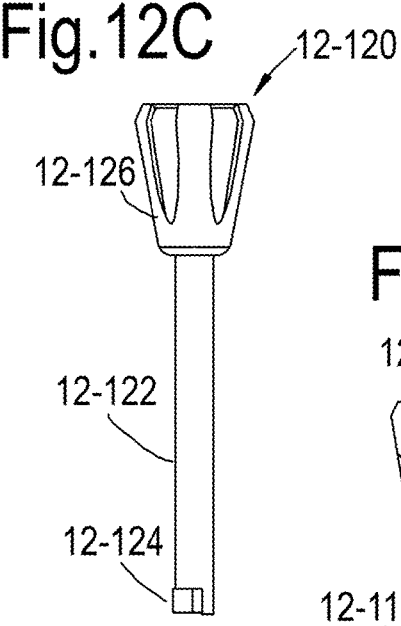
Figure 12D:
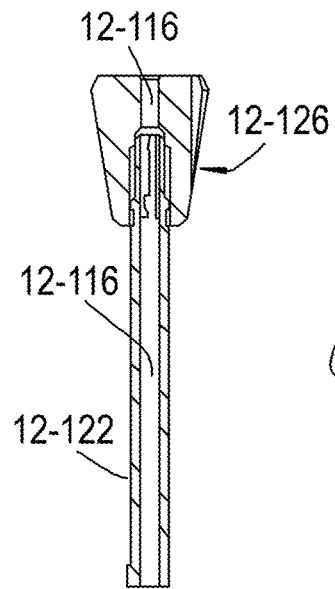
Figure 12E:
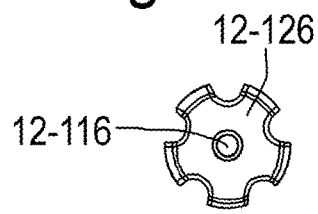
Figure 12F:
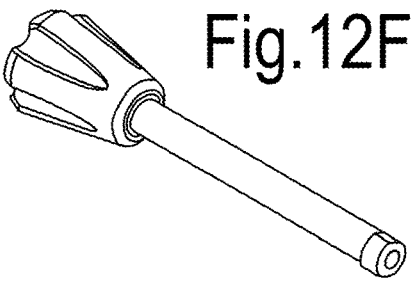

Referring now to FIGS. 12A and 12B, a "locker" device 12-120 can be utilized, which in some aspects, may fit over the immobilizing structure 12-100 to lock same to the jig base 12-10. As is seen in FIGS. 12C-12F, the locker 12-120 will comprise a central hollow 12-116, which spans the shaft 12-122 and head piece 12-126 of the locker 12-120. In one aspect, the locker 12-120 will comprise a terminal locking extension 12-124 on the shaft 12-122 that engages a complementary fastener structure, for example, a complementary slot positioned on the jig base, which facilitates locking the locker into place and preventing movement of the jig base or K-wire inserted therethrough. In some aspects, the locker head piece 12-126 may comprise ridges or other protruding structure to facilitate manual locking of same.

Referring to FIGS. 12G-12L, other aspects of the embodied lockers are shown. The locker shaft may comprise a terminal threaded region 12-130, with a fitted joint region 12-132, such that when the locker head piece 12-126 is fitted onto same, individual sections of the fitted joint region 12-132 may be brought closer together to effectively narrow the diameter of the hollow region 12-116 to more securely lock around the immobilizing structure fitted therethrough. According to this aspect, the locker head piece 12-126 will comprise a threaded region 12-128, which promotes the narrowing of the diameter of the hollow region as described.

In some aspects, the aligning stabilizer base is now substantially immobilized, with a region into which a desired implant will be inserted being internal to the boundaries of the aligning stabilizer base.

In some aspects, the region of tissue into which a desired implant will be inserted contains a defect site in underlying bone, cartilage or both.

Referring to FIG. 13A a "perpendicular aligner" (13-140) is fitted within the aligning stabilizer base 13-10. FIGS. 13B and 13D show cut away longitudinal sections of the perpendicular aligner 13-140 further depicting the presence of a hollow 13-116 spanning through the perpendicular aligner 13-140 through which immobilizing structures such as K-wires or adapted K-wire screws may be inserted. The perpendicular aligner 13-140 has a base 13-134 which specifically inserts within a jig base, and a stopper 13-136, which prevents unchecked advance of the perpendicular aligner 13-140 within the jig base. A shaft or shafts 13-138 connect the perpendicular aligner base with the top handle 13-142 of the perpendicular aligner 13-140 provides an easy gripping surface for insertion within the jig base. The Figure depicts the perpendicular aligner providing for two shafts and thereby insertion of two immobilizing structures but the skilled artisan will readily appreciate that any series of multiples or a single aligner is contemplated and may be adapted for a particular use, e.g. depending upon the defect site being treated.

FIG. 13F depicts the threading of two immobilizing structures 13-100 through the perpendicular aligner 13-140, and insertion of same within the underlying tissue. Following same, the perpendicular aligner can be carefully removed, leaving the jig base immobilized to the site, and further containing immobilizing structures positioned in a perpendicular orientation to the long axis of the defect site, for ideal incorporation of an implant within the defect site as part of the implantation procedure.

Figure 14C:
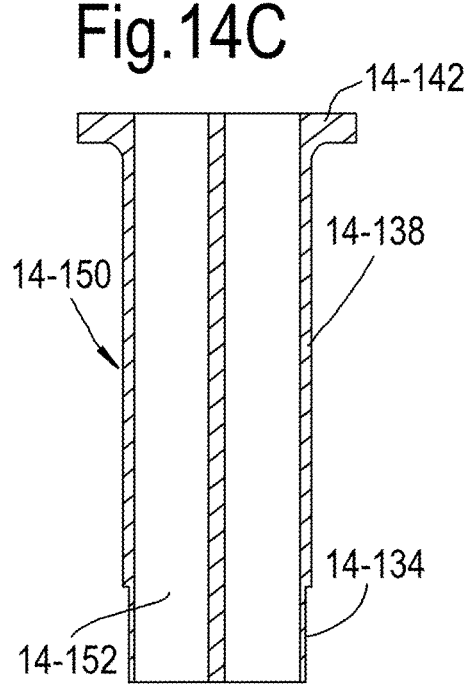
Figure 14D:
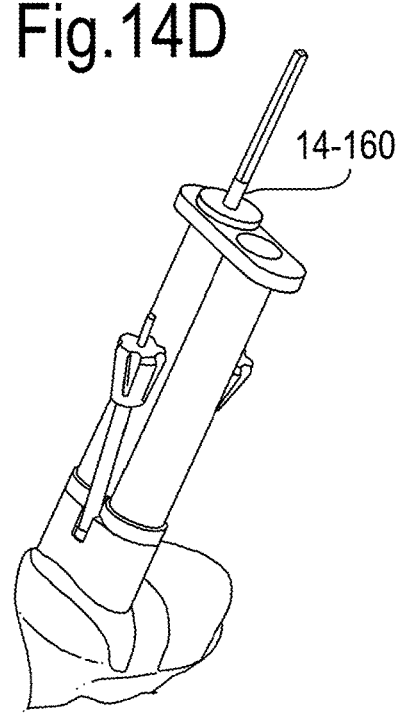
Figure 14E:
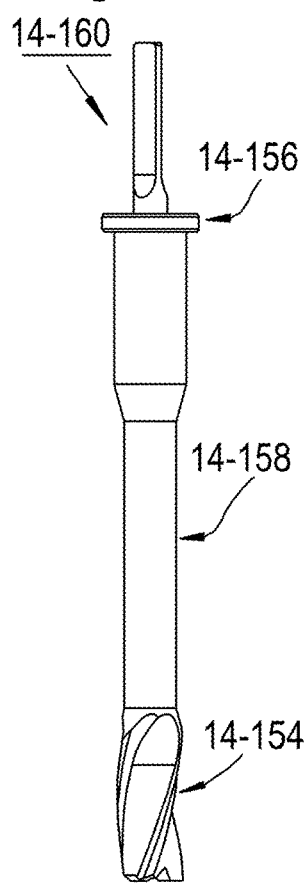
Figure 14F:
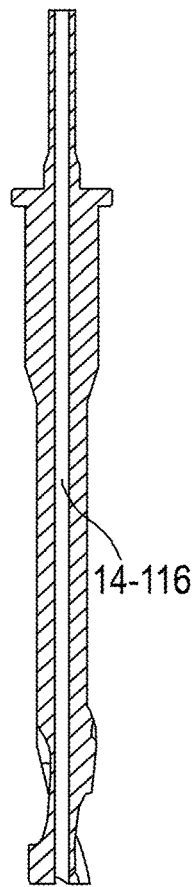
Figure 14G:
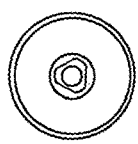
Figure 14H:
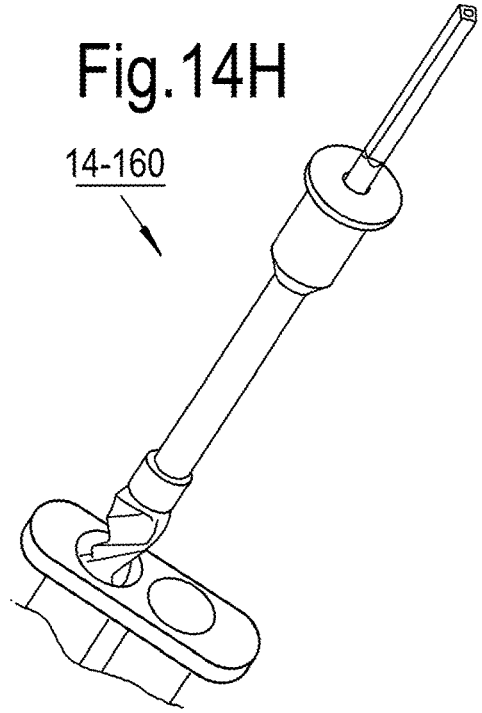

FIG. 14A and FIG. 14B depict a specialized drill protective sheath 14-150, which may contain one, two, or three, etc. barrels 14-138 through which an immobilizing structure, and drill bit may insert, as will be appropriate, depending upon the defect site being treated. FIG. 14C shows a longitudinal section through the drill protective sheath shown in FIG. 14B.

In this aspect, a drill protective sheath 14-150 with two barrels 14-138 are shown. The base 14-134 of the drill protective sheath will be so modified and sized such that it will insert within the jig base. The drill protective sheath will also further comprise a stopper structure 14-136 to prevent unchecked advancement of the drill protective sheath within the jig base. The drill protective sheath will contain hollows 14-152 spanning through each top portion 14-142, barrels 14-138 and base 14-134, so that the immobilizing structures may insert therethrough. The drill protective sheath top 14-142 may be so modified such that when a drill bit is inserted therethrough, the top provides a stopper mechanism, as well, preventing unchecked advancement of the drill and drill bit within the drill protective sheath 14-150.

The drill protective sheaths 14-150 of this invention are designed to promote insertion of the drill bit 14-160 therethrough. Referring to FIGS. 14D-14H, some embodied drill bits include a bit containing a central hollow 14-116 that spans the drill bit, so that same can insert over the immobilizing structure. In some aspects, such a drill bit fitting over the immobilizing structure ensures drilling in a particular orientation, optimized for ideal preparation of the implant site.

In some aspects, the drill bit 14-160 will comprise a stopper 14-156, which prevents continued advancement of the drill bit within the protective sheath, as it catches on the top portion 14-142 of the protective sheath. The drill bit will further comprise a shaft 14-158 and specialized terminus 14-154 for drilling into underlying tissue. In some aspects, the drill bit comprises a terminus particularly sized to be a standard fit for most drills in use.

Once drilling is complete, the drill bit may be removed. According to this aspect, a tissue shaper/reamer 15-170 may be used to shape/smooth/contour the edges of the drilled sites in the implant site in the underlying tissue. In one aspect, the tissue shaper/reamer 15-170 may comprise a stopper structure, 15-172, which, similar to the modification of the drill bit, prevents continued advancement of the tissue shaper/reamer within the protective sheath, as it catches on the top portion 14-142 of the protective sheath.

Figure 7C:
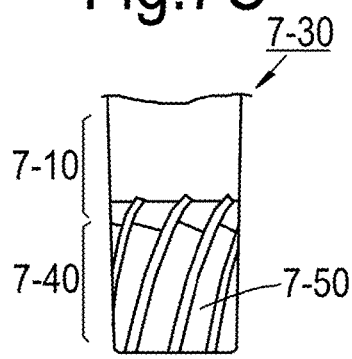
Figure 7D:
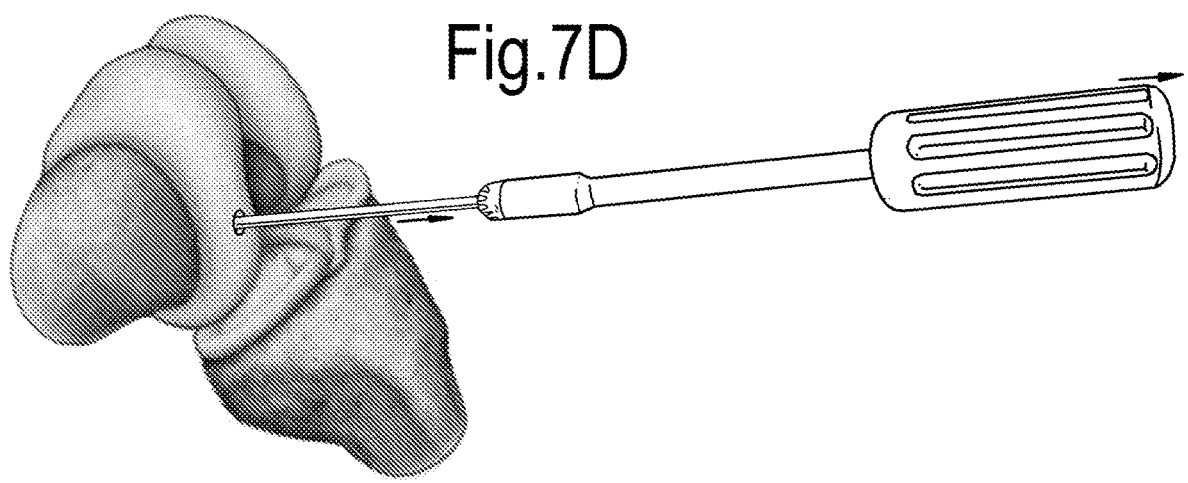

Referring to FIGS. 15C and 15D, as described for FIGS. 7B and 7C hereinabove, the shaper may comprise certain terminal modification, whereby a first shaping region 15-10 is substantially smooth and a second shaping region 15-40 comprises a series of laterally extending protrusions 15-50, and has tapered sides at an angle of two degrees from a longitudinal axis of said tool. The laterally extending protrusions may be further angled (FIG. 15D), if desired.

The shaper is depicted comprising a handle for ease of gripping same, and the skilled artisan will appreciate that various modifications of same are envisioned.

Figure 16C:
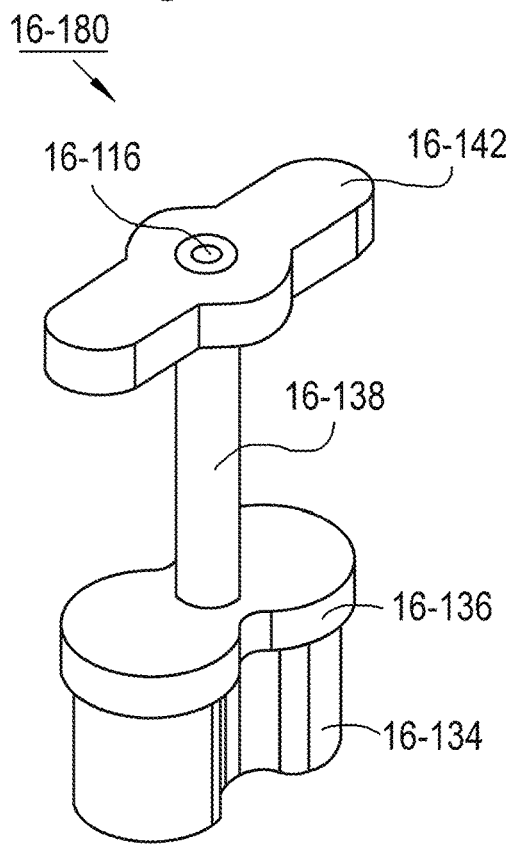
Figure 16D:
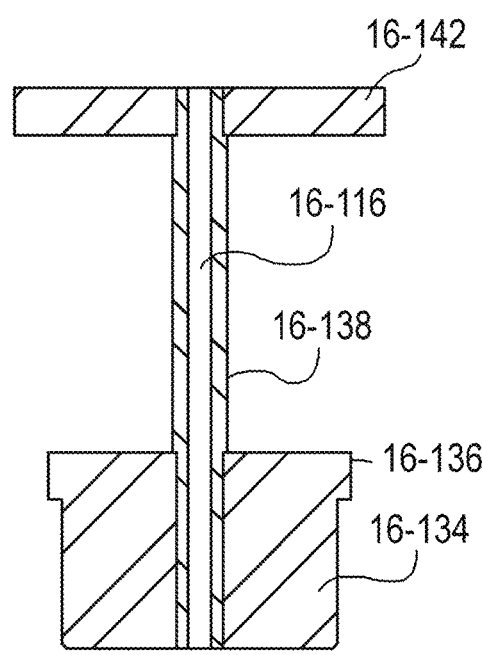
Figure 16E:
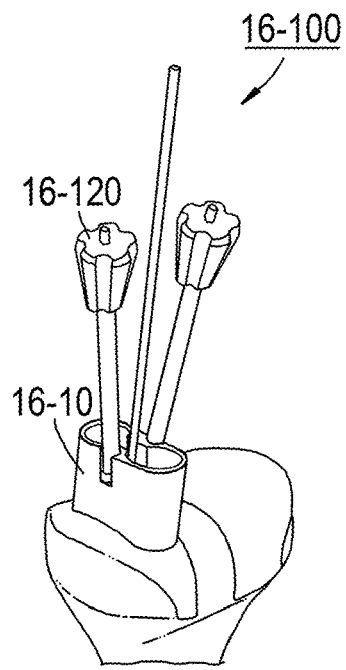
Figure 16F:
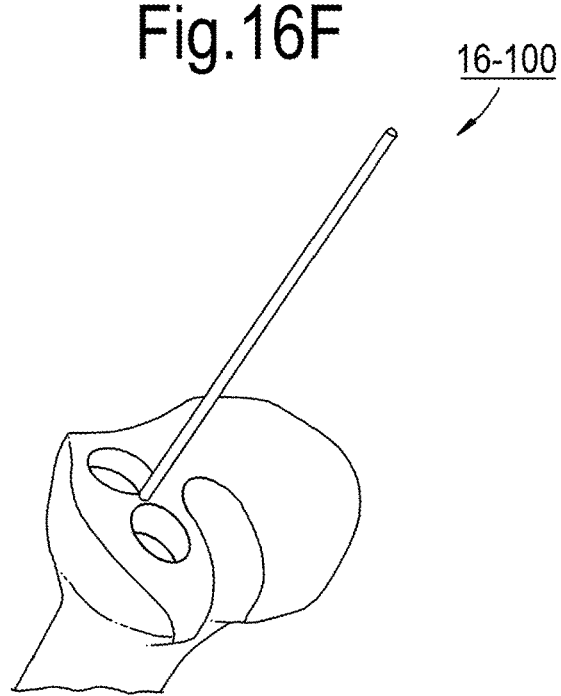

The procedure described through FIG. 15D has produced two drilled substantially smoothed circular voids in the underlying tissue into which an implant may be inserted, which can be seen in FIG. 16F. In some embodiments, it is of interest to further modify same to create a single large void into which an implant may insert, such as that depicted in FIG. 19D. Toward this end, it may be of interest to join the two voids seen in FIG. 16F, and further smooth the outer boundaries of the joined voids.

While a typical means of accomplishing such enlarging of the implant site to date is typically done "by eye" by the surgeon, using a scalpel or other means, in some aspects, this invention provides a controlled precise means to accomplish same with defined boundaries and depth.

In some aspects, the drill protective sheath 14-150 is removed and a further perpendicular aligner is inserted 16-180 within the base jig (FIG. 16A). According to this aspect, the aligner 16-180 has a central hollow 16-116 spanning the length of the aligner. The aligner will also have a base 16-134, which inserts within the jig base, and a stopper rim region 16-136, which prevents unchecked advancement of the aligner within the implant site. The aligner also has a shaft 16-138 connecting the base to the top 16-142 of the aligner 16-180. An immobilizing structure 16-100 may be inserted through the central void 16-116 in the aligner and embedded within the underlying tissue as described with respect to FIG. 13.

Following careful removal of the aligner, the immobilizing structure is placed at the midpoint between the two previously created voids in the underlying tissue, as seen in FIGS. 16E and 16F. The lockers 16-120 may then be removed and the jig base 16-10 removed, such that only the immobilizing structure remains (FIG. 16F).

Figure 17E:
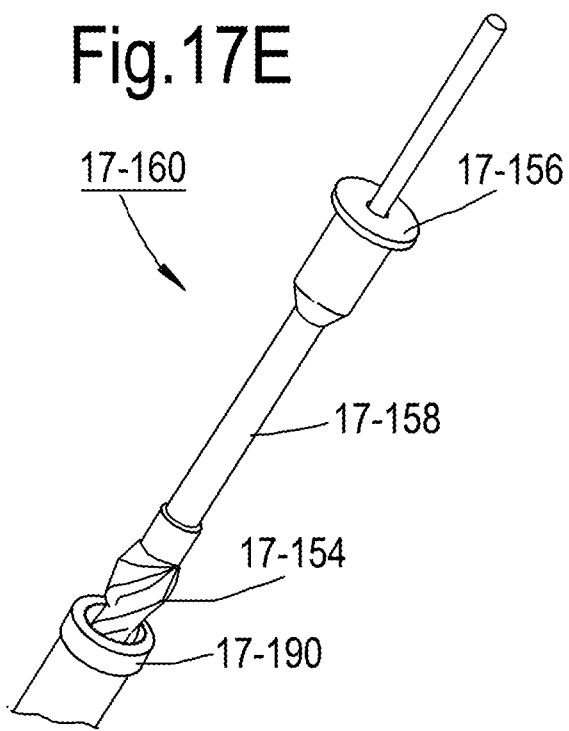
Figure 17F:
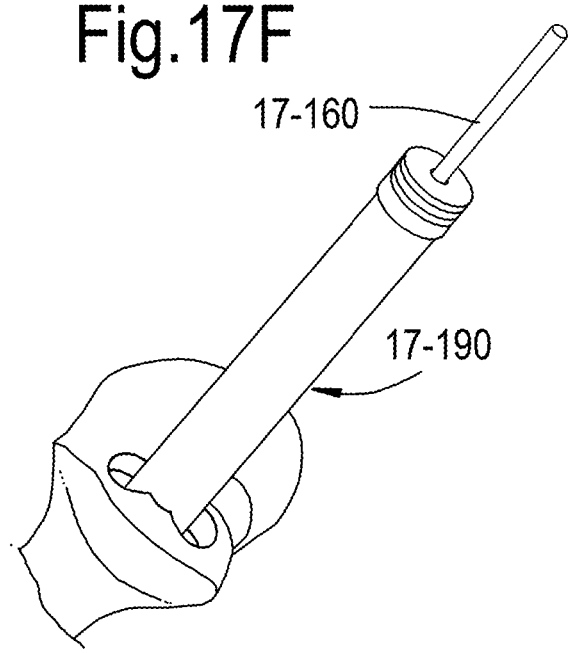
Figure 17G:
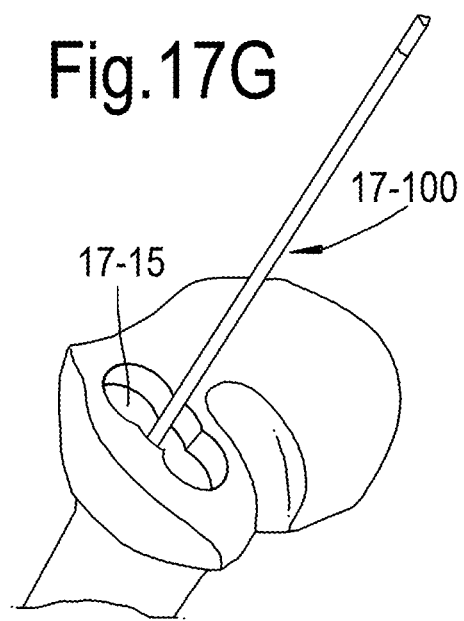

In some aspects, in order to enlarge, shape and further smooth the implant site, a drill protective sheath 17-190 as depicted in FIG. 17 is inserted. The drill protective sheath will have two or more terminal insertion anchors 17-182. The drill protective sheath will have a central hollow 17-188 within the shaft 17-184 of the drill protective sheath. The drill protective sheath 17-190 may also further comprise an upper rim 17-186, which may also serve as a stopper, as further described herein.

The drill protective sheath 17-190 is placed over the immobilizing structure, so that same is essentially centrally located within the central hollow 17-188. The drill bit 17-160 as described hereinabove, and as depicted in FIG. 17E is then placed over the immobilizing structure 17-100, and within the drill protective sheath hollow 17-188. The drill bit stopper 17-156 also prevents unchecked advancement of the bit within the protective sheath, as same catches on the upper rim 17-186 of the drill protective sheath. Once the drilling is complete, the drill bit and drill protective sheath are removed, and only the immobilizing structure 17-100 remains within the implant site 17-15. In accordance with this aspect, as will be appreciated, the profile of three circles may be seen to have been created within the implant site 17-15 in FIG. 17G. Comparing the shape/contour of the prepared implant site in FIG. 17G with that of the desired implant site contour of FIG. 19D, reveals the potential to further smooth the outer edges of the prepared site to create the desired shape seen in FIG. 19D.

Figure 18A:
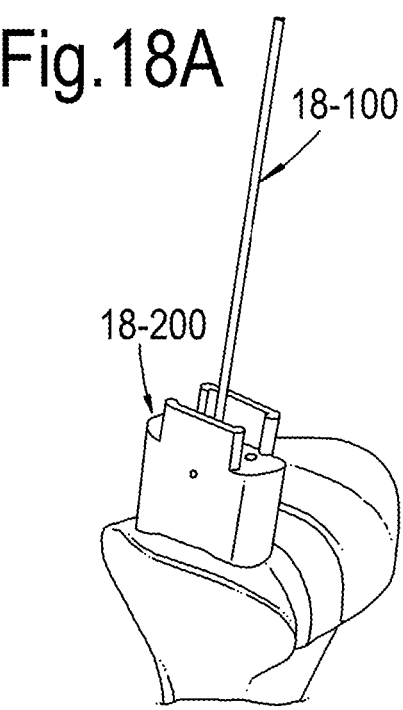
FIGS. 18A-18G schematically depict an embodied contour cutter 18-200 comprising a central hollow 18-116, through which the immobilizing structure 18-100 may insert, at least one blade structure 18-194, which in a first position is elevated above the tissue surface. Additional immobilizing structures, such as K wires 18-202, inserted through specialized structures 18-192 in the contour cutter are shown. The contour cutter will comprise rounded termini 18-198, to insert within the rounded boundaries of the prepared implant site. In order to lower the blade structure 18-194, a mallet 18-210, comprising a central hollow, is threaded over the immobilizing structure, with the long axis of the mallet head 18-212 being in a perpendicular orientation to that of the long axis of the contour cutter. Once the blade structure is fully engaged, the mallet 18-120 is carefully removed.
Figure 18B:
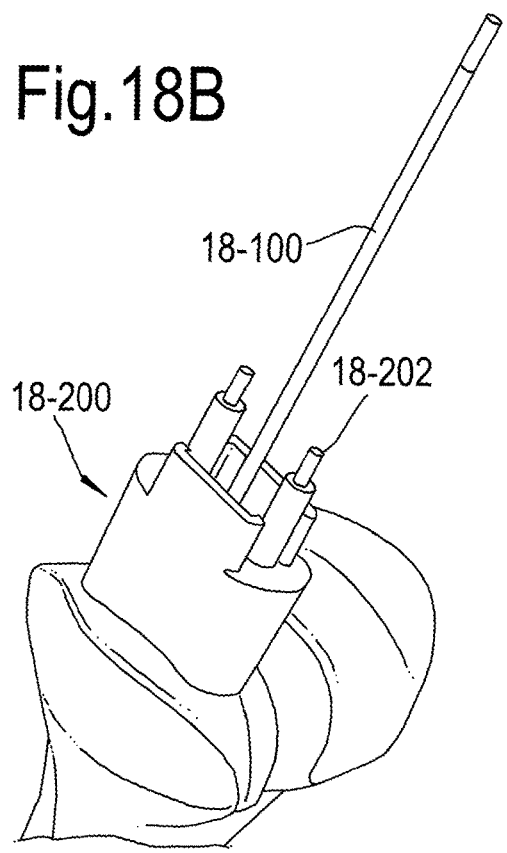
Figure 18C:
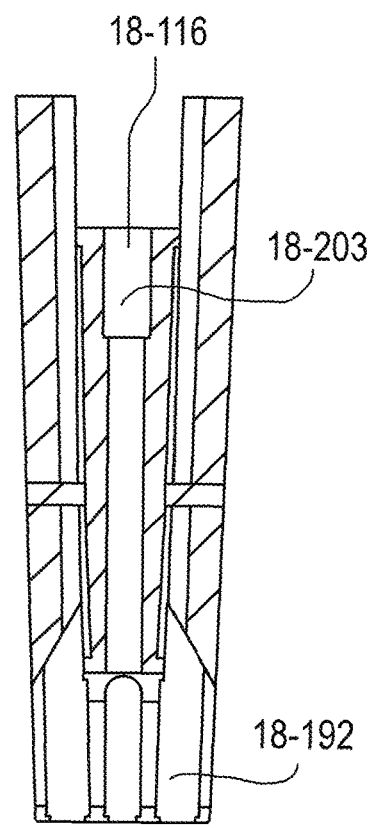
Figure 18D:
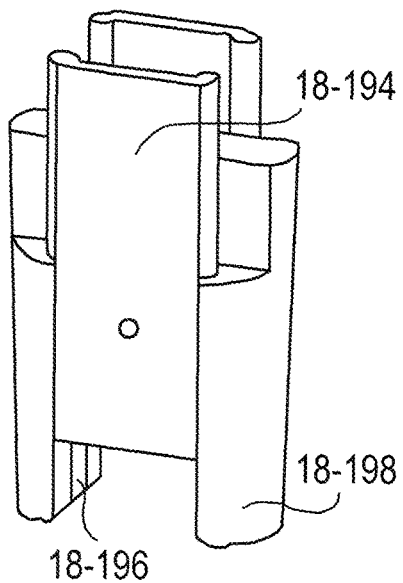
Figure 18E:
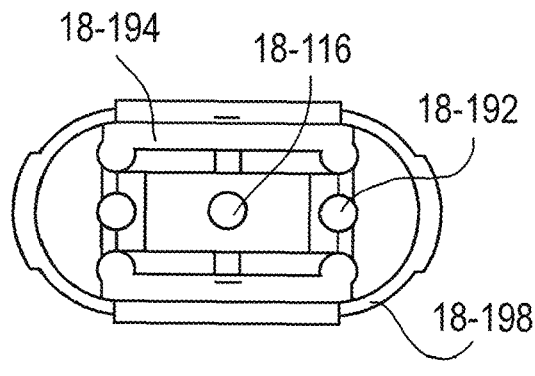
Figure 18F:
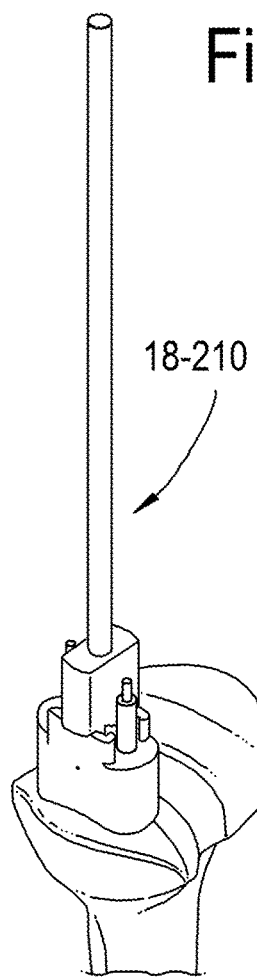
Figure 18G:
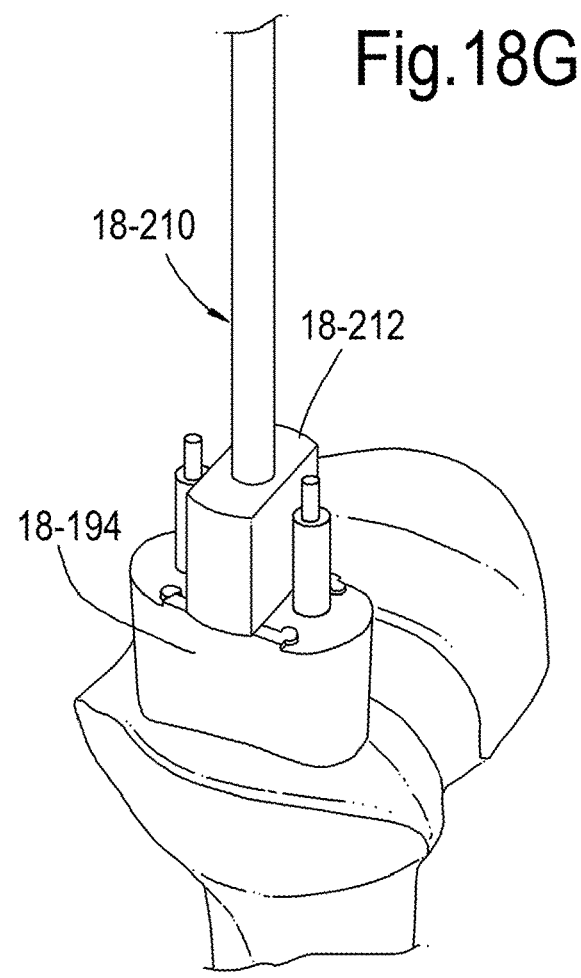

FIG. 18A depicts the "cutting jig" or "contour cutter" 18-200 placement within the boundaries of the implant site. As will be appreciated, the contour cutter comprises a central hollow 18-116, through which the immobilizing structure 18-100 may insert. Referring to FIGS. 18B-18E, the contour cutter will comprise at least one blade structure 18-194, which inserts with the cutting contour such that upon first contact with the implant site, the blade structure 18-194 is elevated. In this embodiment, the contour cutter possesses two blade structures 18-194, as shown. The blade structure/s may be subsequently lowered using a specialized tool/mallet as further described.

The contour cutter may be affixed to the implant site via the insertion of additional immobilizing structures, such as K wires 18-202, which may insert through specialized structures 18-192 in the contour cutter. The contour cutter will comprise rounded termini 18-198, to insert within the rounded boundaries of the prepared implant site.

In order to lower the blade structure 18-194, a mallet 18-210, comprising a central hollow, is threaded over the immobilizing structure, as well, with the long axis of the mallet head 18-212 being in a perpendicular orientation to that of the long axis of the contour cutter. Once the blade structure is fully engaged, the mallet 18-120 is carefully removed.

In some aspects, in order to smoothly and carefully remove the contour cutter and avoid in any way altering the now prepared implant site, a slide hammer 19-220 is fittedly affixed to the contour cutter. Referring to FIG. 19, the slide hammer 19-220 is depicted, containing a central hollow 19-116, which inserts over the immobilizing structure, as well. The slide hammer has a shaft 19-204 onto which a hammer 19-206 is slidingly attached, and further comprises a stopper 19-208.

The slide hammer 19-220 will further comprise a fitted insertion tip 19-205, which inserts in a fitted manner within a recess 18-203 in the contour cutter for ease of removal of the contour cutter. In some aspects, the press fit is sufficiently fitted to enable extraction of the contour cutter. In some aspects, the recess 18-203 is threaded, as is the insertion tip 19-205 in a complementary fashion to promote a more specific fit for the slide hammer within the contour cutter.

Once the contour cutter is removed, a smooth, large implant site 19-225 remains, and a desired implant may be manually inserted therein.

In some aspects, the inserted implant may be ideally fit within the implant site by use of a tamper 20-230 (FIG. 20A). Such tamper may have specialized terminal modifications suited for ideal implantation. For example, and in some embodiments, as the implant may be curved, the tamper may have a terminal modification to have a curved surface.

Referring to FIGS. 20C-20F, the tampers will comprise a handle region 20-232, connected via a shaft 20-234 to the tamper head region 20-236.

As the tamper engages the implant in order to facilitate insertion of same within the implant site, it is desirable that the tamper head comprise a non-stick surface, for the surface engaging the implant.

Figure 20C:
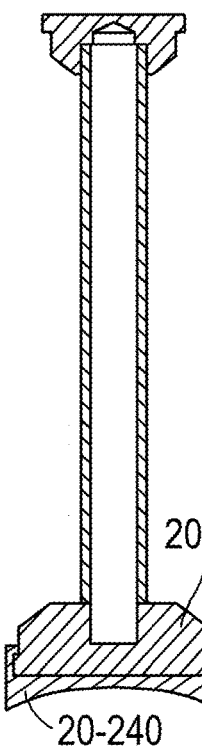
Figure 20D:
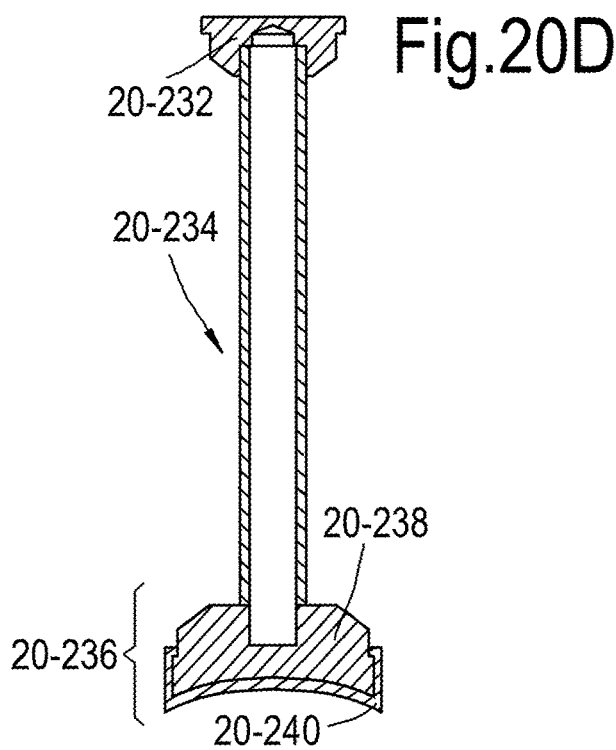
Figure 20E:
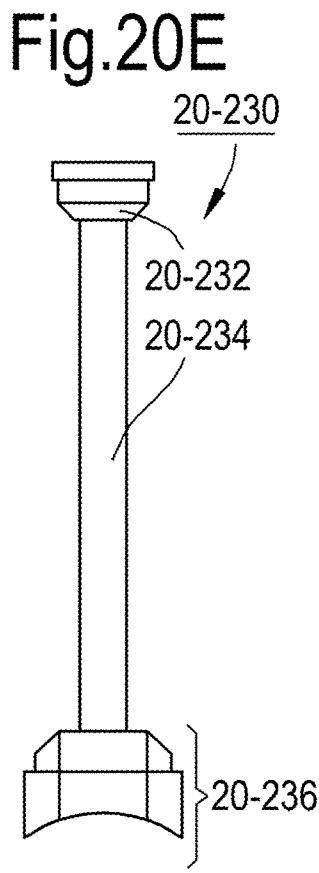
Figure 20F:
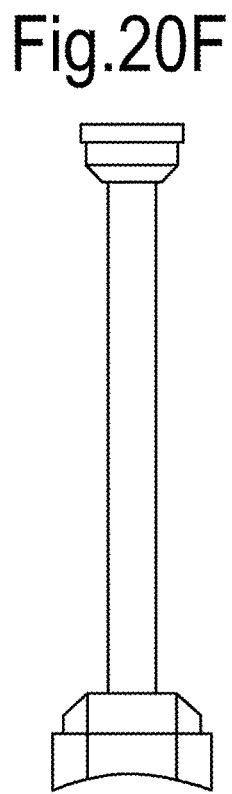
Figure 20G:
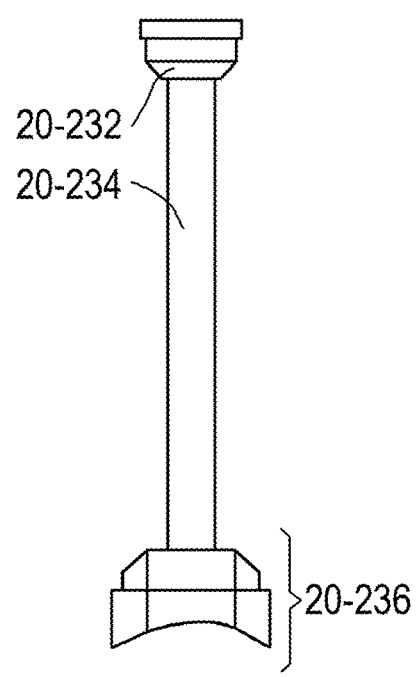

In some aspects, the tamper head region may comprise a flat terminus 20-238, which is attached to a curved non-stick component 20-240, and the angle of curvature is dictated by the curvature present in the curved non-stick component 20-240 (FIG. 20C). In some aspect, the tamper head region comprises a curved terminus 20-238, to which is attached a curved non-stick component 20-240, and the angle of curvature is dictated by the curvature present in both the head region curved terminus as well as the curvature present in the curved non-stick component 20-240 (FIG. 20D).

It will be appreciated that the invention contemplates kits comprising any appropriate arrangement of the tools as herein described.

One embodiment of a kit of tools is depicted in FIG. 21A, where the indicated tools are provided, including their designated numbering.

FIG. 21B-D depict additional immobilizing structures 21-100 that can be incorporated in the kits and for use in the methods of this invention. The immobilizing structures can be of any convenient length, and will comprise a top 21-260 portion, which optionally can be of a standard geometry to fit for example, within a standard drill or chuck. The immobilizing structure will further comprise a shaft 21-240, and will comprise an insertion point 21-250, which in some embodiments is a sharp-tipped point, or in other embodiments, is a screw-like structure or in other embodiments, is any appropriate shape and orientation for insertion within tissue.

The immobilizing structure may further comprise a terminal stopper. FIG. 21B depicts an embodied immobilizing structure containing a stopper 21-270, which when the immobilizing structure inserts within the jig base, fixes same acting, in some capacity as the lockers as herein described Example 5

Customized Tools and Implants for Ideal Implantation Protocols for Implantation of an Optimized Solid Substrate within a Condyle A substrate, for example, an optimized substrate as described in Example 2 may be implanted in a defect site, and it will be appreciated that such implants may be scaled to size. In some aspects, a 2 degree optimal taper angle for the sides of implant will be introduced. In some aspects, such implant will be further optimized in terms of overall dimension, as well as radius of curvature to approximate that of the defect site.

A plurality of images are obtained of the defect site and rendered together to produce a 3D image showing the bone and/or cartilage region. It is to be understood that the medical images are images in the transverse, coronal or sagittal planes of a patient or biological organism and the planes depend on a diagnostic task. The medical images may be any images that are capable of capturing bone regions of a patient or biological organism. The medical images can be otherwise referred to as medical scan images. They can be X-ray images, computed tomography images, magnetic resonance images or any other medical images.

The medical images may then be analyzed in a computing device and the intensity of e.g. the grey shades are computed through the grey level values that can be stored in binary or quantized forms. The values are converted to vector data by a mathematical equation, which in some aspects is a linear equation.

The vector data may be in forms of arcs and lines that are geometrically and mathematically associated. The vector data may be stored as a series of pixel pairs, for example, in a polygon (PLY) file format as it is simple, fast in saving and loading as well as easy to be implemented for a wide range of computer programmes.

In some aspects, the step of converting the segmented medical images into the 3D data is by using a Marching cube algorithm, Delaunay's triangulation algorithm or a combination thereof. Marching cube algorithm, Delaunay's triangulation algorithm or the combination thereof may in some aspects be used due to its isotropic ability to expand pixels of the vector data in a single direction. The pixels in the medical images may be interpolated to form connecting series of pixel pairs.

In some aspects, a customized implant may be prepared, by first isolating a solid substrate as herein defined characterized by having a specific fluid uptake capacity value of at least 75%, and machining of same to produce a 3D customized implant which matches and fits the defect areas of the bone and/or cartilage region, in particular in terms of the radius of curvature of the surface of the implant which serves to fill in a curved region in the implant site tissue.

In some aspects use of Computer numerical controlled (CNC) high-tech machines for tool and implant manufacture is specifically contemplated.

In some aspects, the customized implant is meant to be placed on the defect area of the bone region where repairing or re-shaping is needed. The defect area may be a missing bone, a crack or merely undesired shape. The customized implant produced is preferred to be seamlessly and smoothly compatible to the bone region.

Furthermore, as contemplated herein, a series of customizable tools may be prepared, whereby such tools, in particular, the jig base and tampers as herein described may be specifically manufactured to comprise a radius of curvature and appropriate dimensions to be customized for use with a particular patient, based on the specific criteria established via the 3D rendering aspects as described hereinabove.

Such fully customized implants and tools provide, in some aspects for a surgical procedure that in some aspects, can be shortened as the customized implant fits well to the patient's defect area and modification during surgery is therefore not needed. In some aspects, such fully customized implant and tools reduces surgical risks, as well.

In some aspects, procedures as described in PCT International Patent Application Publication Number WO 2014178706 may be adapted to suit the customized procedures described herein.

It will be understood by those skilled in the art that various changes in form and details may be made therein without departing from the spirit and scope of the invention as set forth in the appended claims. Those skilled in the art will recognize, or be able to ascertain using no more than routine experimentation, many equivalents to the specific embodiments of the invention described herein. Such equivalents are intended to be encompassed in the scope of the claims.

In one embodiment of this invention, "about" refers to a quality wherein the means to satisfy a specific need is met, e.g., the size may be largely but not wholly that which is specified but it meets the specific need of cartilage repair at a site of cartilage repair. In one embodiment, "about" refers to being closely or approximate to, but not exactly. A small margin of error is present. This margin of error would not exceed plus or minus the same integer value. For instance, about 0.1 micrometers would mean no lower than 0 but no higher than 0.2. In some embodiments, the term "about" with regard to a reference value encompasses a deviation from the amount by no more than 5%, no more than 10% or no more than 20% either above or below the indicated value.

In the claims articles such as "a", "an" and "the" mean one or more than one unless indicated to the contrary or otherwise evident from the context. Claims or descriptions that include "or" or "and/or" between members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides, in various embodiments, all variations, combinations, and permutations in which one or more limitations, elements, clauses, descriptive terms, etc., from one or more of the listed claims is introduced into another claim dependent on the same base claim unless otherwise indicated or unless it would be evident to one of ordinary skill in the art that a contradiction or inconsistency would arise. Where elements are presented as lists, e.g. in Markush group format or the like, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in haec verba herein. Certain claims are presented in dependent form for the sake of convenience, but Applicant reserves the right to rewrite any dependent claim in independent format to include the elements or limitations of the independent claim and any other claim(s) on which such claim depends, and such rewritten claim is to be considered equivalent in all respects to the dependent claim in whatever form it is in (either amended or unamended) prior to being rewritten in independent format.

What is claimed is:

1. An optimized solid substrate for promoting cell or tissue growth or restored function, which solid substrate comprises a coral or coral derivative, is characterized by a specific fluid uptake capacity value of at least 75% or is characterized by having a contact angle value of less than 60 degrees, when in contact with a fluid, and which solid substrate is further characterized by
   at least one substantially flat cross section at a terminus of said solid substrate;
   a conical or pyramidal frustum shape; and
   tapered sides at an angle of from 0.75 to about 4 degrees from a longitudinal axis along said solid substrate.

2. An optimized solid substrate for promoting cell or tissue growth or restored function, which solid substrate comprises a coral or coral derivative characterized by a specific fluid uptake capacity value of at least 75% or is characterized by having a contact angle value of less than 60 degrees, when in contact with a fluid and which solid substrate is further characterized by
  a conical or pyramidal frustum shape; and
  tapered sides at an angle of from 0.75 to about 4 degrees from a longitudinal axis along said solid substrate.

3. The solid substrate of claim 1 or 2, wherein said tapered sides are at an angle of about two degrees from a longitudinal axis along said solid substrate.

4. The solid substrate of claim 1 or 2, wherein said solid substrate is isolated from a *Porites* species, a *Goniopora*, a *Millepora* species or an *Acropora* species.

5. The solid substrate of claim 1 or 2, said solid substrate comprises a hollow or hollows along a Cartesian coordinate axis of said solid substrate.

6. The solid substrate of claim 1 or 2, wherein said solid substrate comprises a biocompatible polymer.

7. The solid substrate of claim 6, wherein said biocompatible polymer is incorporated within voids or pores in said substrate.

8. The solid substrate of claim 6, wherein said biocompatible polymer is attached to an outer surface of said substrate.

9. The solid substrate of claim 6, wherein said biocompatible polymer is present in a separate phase associated with a terminus of said solid substrate.

10. The solid substrate of claim 6, wherein said biocompatible polymer comprises a natural polymer.

11. The solid substrate of claim 10, wherein said natural polymer comprises alginate.

12. The solid substrate of claim 11, wherein said alginate comprises calcium alginate, cross linked calcium alginate or a combination thereof.

13. The solid substrate of claim 10, wherein said natural polymer comprises chitosan.

14. The solid substrate of claim 13, wherein said chitosan comprises cross linked chitosan.

15. The solid substrate of claim 10, wherein said natural polymer comprises glycosaminoglycan.

16. The solid substrate of claim 15, wherein said glycosaminoglycan is hyaluronic acid, sodium hyaluronate, cross linked hyaluronic acid, or a combination thereof.

17. The solid substrate of claim 10, wherein said natural polymer comprises a glycosaminoglycan, collagen, fibrin, elastin, silk, chitosan, alginate, and any combinations thereof.

18. The solid substrate of claim 1 or 2, wherein said solid substrate further comprises a cytokine, a growth factor, a therapeutic compound, a drug, or any combination thereof.

19. The solid substrate of claim 1 or 2, wherein said solid substrate has a height of about 5-40 mm.

20. The solid substrate of claim 1 or 2, wherein said solid substrate has a height of about 1 cm to about 5 cm.

21. The solid substrate of claim 1 or 2, which is an allograft or autograft.

22. A kit comprising at least one solid substrate of claim 1 or 2.

23. The kit of claim 22, wherein said kit further comprises a biocompatible polymer.

24. The kit of claim 23, wherein said biocompatible polymer is hyaluronic acid.

25. A method for implantation of an optimized solid substrate for promoting cell or tissue growth or restored function in a subject in need thereof, said method comprising:
  Isolating or preparing an optimized solid substrate for promoting cell or tissue growth or restored function, which solid substrate comprises a coral or coral derivative, is characterized by a specific fluid uptake capacity value of at least 75%, or is characterized by having a contact angle value of less than 60 degrees and which is further characterized by at least one substantially flat cross section at a terminus of said solid substrate and tapered sides at an angle of from 0.75 to about 4 degrees from a longitudinal axis along said solid substrate;
  establishing a specific fluid uptake capacity value of said solid substrate, which specific fluid uptake capacity value is determined by establishing a spontaneous fluid uptake value divided by a total fluid uptake value;
  selecting a solid substrate characterized by a specific fluid uptake capacity value of at least 75% or is characterized by having a contact angle value of less than 60 degrees; and
  implanting said solid substrate characterized by a specific fluid uptake capacity value of at least 75% or is characterized by having a contact angle value of less than 60 degrees within a desired site in a subject, wherein said implanting is conducted at an angle from an axis perpendicular to the surface of the tissue site being thus treated;
  wherein said solid substrate is characterized by a conical or pyramidal frustum shape.

26. A method for implantation of an optimized solid substrate for promoting cell or tissue growth or restored function in a subject in need thereof, said method comprising:
  Isolating or preparing an optimized solid substrate for promoting cell or tissue growth or restored function, which solid substrate comprises a coral or coral derivative, is characterized by a specific fluid uptake capacity value of at least 75%, or is characterized by having a contact angle value of less than 60 degrees and which is further characterized by comprising tapered sides at an angle of from 0.75 to about 4 degrees from a longitudinal axis along said solid substrate;
  establishing a specific fluid uptake capacity value of said solid substrate, which specific fluid uptake capacity value is determined by establishing a spontaneous fluid uptake value divided by a total fluid uptake value;
  selecting a solid substrate characterized by a specific fluid uptake capacity value of at least 75% or is characterized by having a contact angle value of less than 60 degrees; and
  implanting said solid substrate characterized by a specific fluid uptake capacity value of at least 75% or is characterized by having a contact angle value of less than 60 degrees within a desired site in a subject, wherein said implanting is conducted at an implant angle of from 0.75 to about 4 degrees from an axis perpendicular to the surface of the tissue site being thus treated;
  wherein said solid substrate is characterized by a conical or pyramidal frustum shape.

27. The method of claim 25 or 26, wherein said solid substrate can be used as a bone filler or bone substitute material.

28. The method of claim 25 or 26, wherein said solid substrate further comprises a bone filler or bone substitute material.

29. The method of claim 25 or 26, wherein said establishing a specific fluid uptake capacity value of said solid substrate comprises the step of contacting said solid substrate with a fluid for from 0.1-15 minutes, allowing for spontaneous fluid uptake of said fluid within said solid substrate to arrive at said spontaneous fluid uptake value.

30. The method of claim 25 or 26, wherein said establishing a specific fluid uptake capacity value of said solid substrate further comprises the step of contacting said solid substrate with a fluid and applying negative pressure to said solid substrate to promote maximal uptake of said fluid within said solid substrate to arrive at a total fluid uptake value.

31. The method of claim 30, wherein said fluid is a blood analog.

32. The method of claim 30, wherein said fluid is a biologic fluid that is autologous with respect to a cell or tissue of a subject when said solid substrate is contacted with a cell or tissue of said subject.

33. The method of claim 25 or 26, wherein said specific fluid uptake capacity value is a function of change in weight in said marine organism skeletal derivative-based solid material.

34. The method of claim 25 or 26, wherein said specific fluid uptake capacity value is a function of change in fluid volume of applied fluid to said marine organism skeletal derivative-based solid material.

35. The method of claim 25 or 26, wherein said method further comprises the step of contacting said solid substrate with cells or tissue.

36. The method of claim 35, wherein said contacting promotes adhesion, proliferation or differentiation, or a combination thereof, of said cells or cells within said tissue.

37. The method of claim 25 or 26, wherein said solid substrate is isolated from a *Porites* species, *Goniopora*, *Millepora* species or an *Acropora* species.

38. The method of claim 25 or 26, wherein said solid substrate comprises a hollow or hollows along a Cartesian coordinate axis of said coralline-based solid material.

39. The method of claim 25 or 26, wherein said solid substrate comprises a biocompatible polymer.

40. The method of claim 39, wherein said biocompatible polymer is applied to said solid substrate in situ.

41. The method of claim 39, wherein said biocompatible polymer is incorporated within voids or pores in said substrate.

42. The method of claim 39, wherein said biocompatible polymer is added to a top surface of said solid substrate during the implantation procedure.

43. The method of claim 39, wherein said biocompatible polymer is attached to an outer surface of said substrate.

44. The method of claim 39, wherein said biocompatible polymer comprises a natural polymer comprising a glycosaminoglycan, collagen, fibrin, elastin, silk, chitosan, alginate, and any combinations thereof.

45. The method of claim 26 or 27, wherein said solid substrate further comprises a cytokine, a growth factor, a therapeutic compound, a drug, or any combination thereof.

46. The method of claim 45, wherein said substrate comprises a therapeutic compound and said therapeutic compound or drug comprises an anti-inflammatory compound, an anti-infective compound, a pro-angiogenic factor or a combination thereof.

47. The method of claim 26 or 27, wherein said solid substrate promotes cell or tissue growth or restored function in tissue damaged by trauma or disease.

48. The method of claim 47, wherein said solid substrate promotes cell or tissue growth or restored function in tissue a subject afflicted with a defect or disorder or disease of the cartilage or bone or a combination thereof.

49. The method of claim 48, wherein said cartilage defect or disorder or disease comprises a full or partial thickness articular cartilage defect; osteochondral defect; osteoarthritis, a joint defect or a defect resulting from trauma, sports, or repetitive stress.

50. The method of claim 48, wherein said defect or disorder or disease of the bone comprises a fracture, bone defect, bone edema, osteoporosis, or a defect resulting from trauma, sports, or repetitive stress.

51. The method of claim 48, wherein said method reduces the incidence or extends the time or need for joint replacement in an affected subject.

52. The method of claim 48, wherein said method serves to resurface an affected joint in a subject.

53. The method of claim 26 or 27, further comprising the step of:
inserting a rod-like structure within a target tissue implantation site in a subject, optionally with the aid of an implement orienting said rod-like structure to be in an orientation perpendicular to a plane of a surface of said target graft withdrawal or implantation site and in an orientation to be centralized within said implantation site;
drilling an area of tissue in said subject which is less than that of a desired tissue implantation site in an orientation perpendicular to a surface of said area of tissue, optionally with a drill bit adapted for application over said rod-like structure;
surgically excising tissue from an area of desired implantation, by optionally applying a surgical cutter over said rod-like structure;
shaping said area of desired implantation with the aid of a tissue shaper and alignment tool comprising:
an elongated body having a central hollow spanning the length of said body;
a shaping structure terminally joined to said elongated body by a joint region having a central hollow and further comprising:
a first shaping region located proximal to said joint region, which first shaping region is substantially smooth and has parallel-oriented sides or sides tapered at an angle with respect to a longitudinal axis of said tool; and
a second shaping region located distal to said joint region, which second shaping region comprises a series of laterally extending protrusions, and has tapered sides at an angle of two degrees from a longitudinal axis of said tool; and
optionally a gripping handle, terminally joined to said elongated body by a joint region located distal to said shaping structure;
wherein said shaping structure is sized to be of a dimension to facilitate a snug fit within the borders of a site of implantation
and applying a tissue graft or solid implant within said area of tissue, optionally by inserting a cannulated implant within said area of desired implantation, over said rod-like structure;
wherein said shaping promotes creation of a site with tapered sides at an angle of two degrees from a longitudinal axis through the site of implantation promoting ideal incorporation of said solid implant.

* * * * *